(12) United States Patent
Matschiner et al.

(10) Patent No.: US 7,892,827 B2
(45) Date of Patent: Feb. 22, 2011

(54) COMPOUND WITH AFFINITY FOR THE CYTOTOXIC T LYMPHOCYTE-ASSOCIATED ANTIGEN (CTLA-4)

(75) Inventors: Gabriele Matschiner, München (DE); Andreas Hohlbaum, Paunzhausen (DE); Steffen Schlehuber, Ruppertsberg (DE); Martin Pöhlchen, Haar (DE); Arne Skerra, Freising (DE)

(73) Assignee: Pieris AG, Freising-Weihenstephan (DE)

( * ) Notice: Subject to any disclaimer, the term of this patent is extended or adjusted under 35 U.S.C. 154(b) by 350 days.

(21) Appl. No.: 11/720,234

(22) PCT Filed: Nov. 25, 2005

(86) PCT No.: PCT/EP2005/012640

§ 371 (c)(1),
(2), (4) Date: Apr. 28, 2008

(87) PCT Pub. No.: WO2006/056464

PCT Pub. Date: Jun. 1, 2006

(65) Prior Publication Data

US 2009/0042785 A1    Feb. 12, 2009

Related U.S. Application Data

(60) Provisional application No. 60/631,227, filed on Nov. 26, 2004, provisional application No. 60/631,253, filed on Nov. 26, 2004, provisional application No. 60/631,200, filed on Nov. 26, 2004, provisional application No. 60/631,202, filed on Nov. 26, 2004, provisional application No. 60/522,970, filed on Nov. 29, 2004, provisional application No. 60/680,067, filed on May 11, 2005, provisional application No. 60/679,811, filed on May 11, 2005.

(51) Int. Cl.
*C12N 5/00* (2006.01)
*C07K 14/00* (2006.01)

(52) U.S. Cl. ............... 435/325; 530/350; 536/23.5

(58) Field of Classification Search ............... 530/350; 536/23.5; 435/325
See application file for complete search history.

(56) References Cited

U.S. PATENT DOCUMENTS 6,719,972 B1    4/2004    Gribben et al.
7,118,915 B2    10/2006   Vogt et al.
7,252,998 B2    8/2007    Skerra et al.

FOREIGN PATENT DOCUMENTS

| WO | WO 00/37504 A2 | 6/2000 |
|---|---|---|
| WO | WO 03/029462 A1 | 4/2003 |
| WO | WO 03/029463 A2 | 4/2003 |
| WO | WO 03/029471 A1 | 4/2003 |

OTHER PUBLICATIONS

Schlehuber et al. (Biophys. Chem. 2002; 96: 213-228).*
Schonfeld et al. (Proc. Natl. Acad. Sci. USA. May 19, 2009; 106: 8198-8203).*
Binder et al. (J. Mol. Biol. 2010; 400: 783-802).*
Beste et al., "Small antibody-like proteins with prescribed ligand specificities derived from the lipocalin fold," PNAS, Mar. 1999, 96:1898-1903.
Skerra et al., "'Anticalins': a new class of engineered ligand-binding proteins with antibody-like properties," Reviews in Molecular Biotechnology, 2001, 74:257-275.

* cited by examiner

*Primary Examiner*—Stephen L Rawlings
(74) *Attorney, Agent, or Firm*—Foley & Lardner LLP

(57) ABSTRACT

The present invention relates to a compound with affinity for the cytotoxic T lymphocyte-associated antigen (CTLA-4), wherein the compound exhibits a synergistic mode of action in that the compound: (a) increases T cell priming or T cell expansion or the generation of memory T cells by blocking of CTLA-4, and (b) enhances effector T cell activity in tumor tissue or lymphoid tissue by blocking of CTLA-4. The compound of the invention can be a protein, a small organic molecule, a peptide, or a nucleic acid. The invention also relates to a mutein derived from a protein selected from the group consisting of human neutrophil gelatinase-associated lipocalin (hNGAL), rat α2-microglobulin-related protein (A2m) and mouse 24p3/uterocalin (24p3), said mutein having binding specificity for the cytotoxic T lymphocyte-associated antigen (CTLA-4), wherein said mutein: (a) comprises amino acid replacements at least one of the sequence position corresponding to sequence positions 33 to 54, 66 to 83, 94 to 106, and 123 to 136 of hNGAL, and (b) binds human CTLA-4 with a $K_D$ of 50 nM or less. The invention also relates to a pharmaceutical composition comprising such a compound or mutein as well as to various pharmaceutical uses of such a compound or mutein, for example, for the prevention and/or treatment of cancer, an auto-immune disease or an infectious disease.

18 Claims, 30 Drawing Sheets

Fig. 8
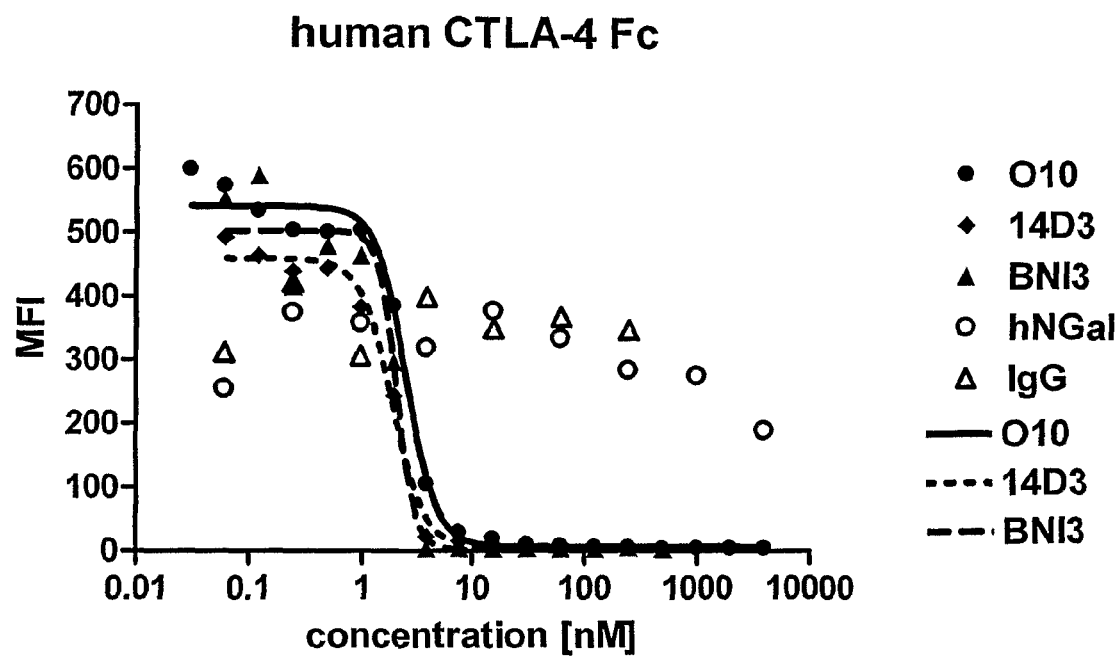
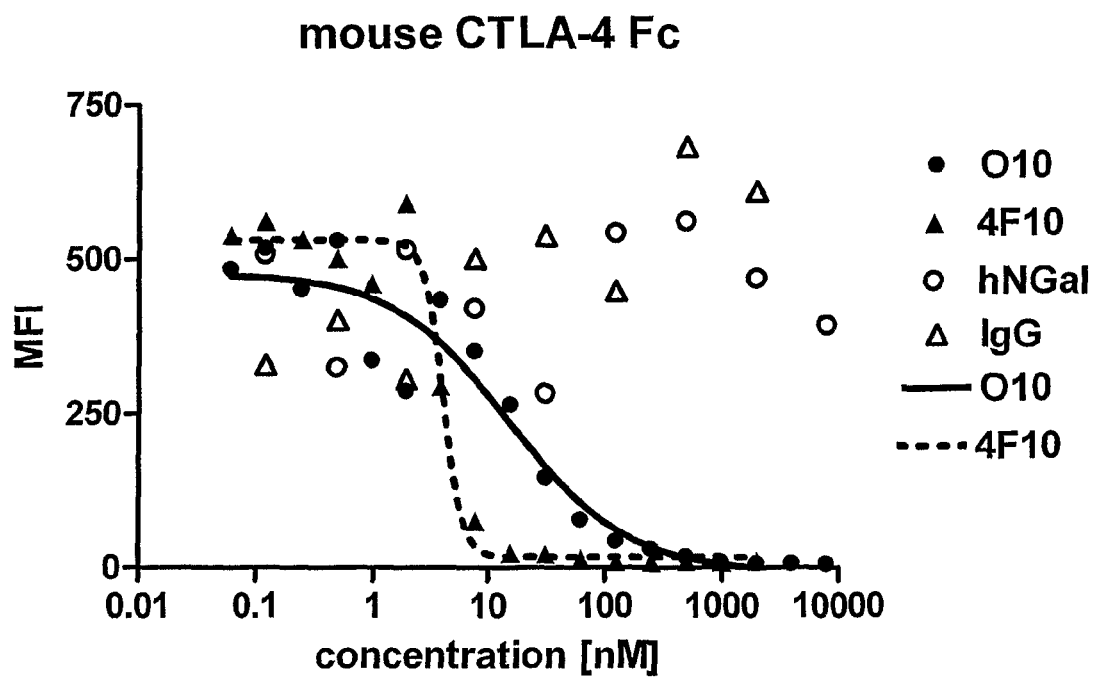

Fig 12b
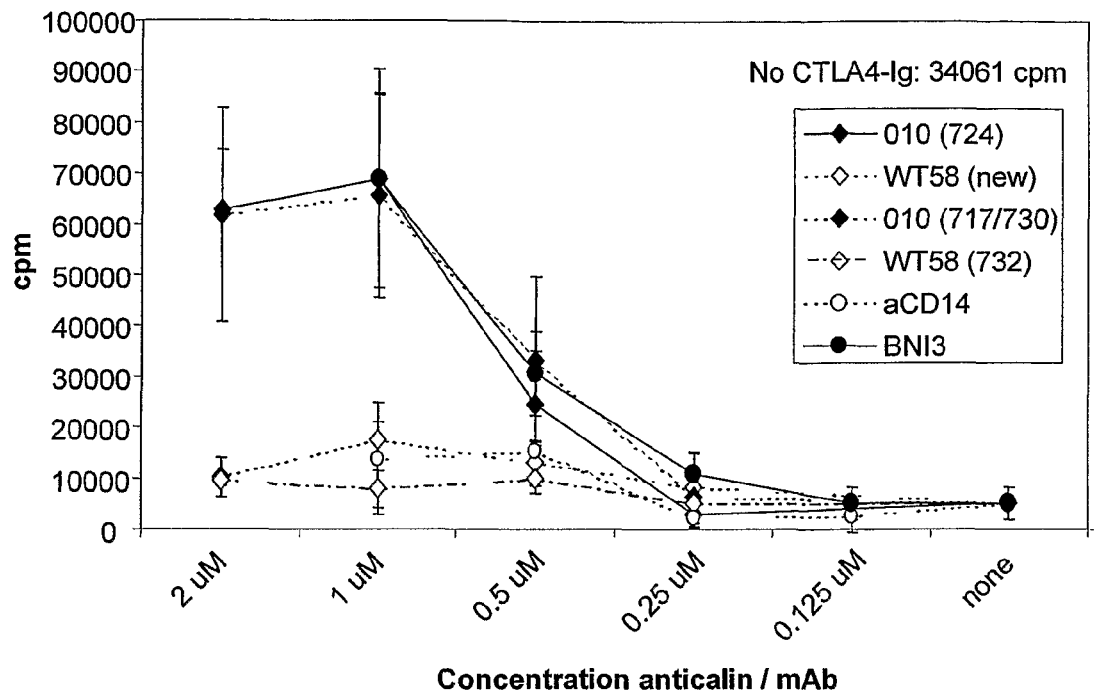
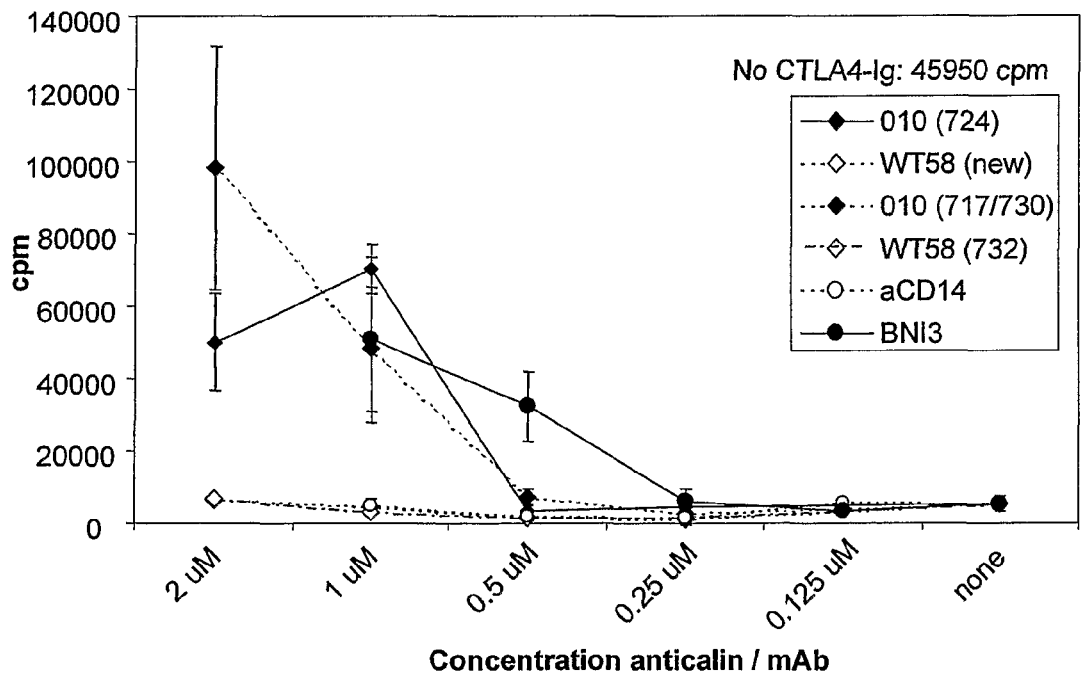

Fig. 15

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|
| hNGAL wt | Q | D | S | T | S | D | L | I | P | A | P | P | L | S | K | V | P | L | Q | Q | N | F | Q | D | N | Q | F | H | G | K | W | Y | V | V |
| S67.2-F03 | Q | D | S | T | S | D | L | I | P | A | P | P | L | S | K | V | P | L | Q | Q | N | F | Q | D | N | Q | F | H | G | K | W | Y | V | V |
| S67.3-C21 | Q | D | S | T | S | D | L | I | P | A | P | P | L | S | K | V | P | L | Q | Q | N | F | Q | D | N | Q | F | H | G | K | W | Y | V | V |
| S94.2-F05 | Q | D | S | T | S | D | L | I | P | A | P | P | L | S | K | V | P | L | Q | Q | N | F | Q | D | N | Q | F | H | G | K | W | Y | V | V |
| S94.7-Q13 | Q | D | S | T | S | D | L | I | P | A | P | P | L | S | K | V | P | L | Q | Q | N | F | Q | D | N | Q | F | H | G | K | W | Y | V | V |
| F92.1-J08 | Q | D | S | T | S | D | L | I | P | A | P | P | L | S | K | V | P | L | Q | Q | N | F | Q | D | N | Q | F | H | G | K | W | Y | V | V |
| S106.1-N15 | Q | D | S | T | S | D | L | I | P | A | P | P | L | S | K | V | P | L | Q | Q | N | F | Q | D | N | Q | F | H | G | K | W | Y | V | L |
| S107.4-C16 | Q | D | S | T | S | D | L | I | P | A | P | P | L | S | K | V | P | L | Q | Q | N | F | Q | D | N | Q | F | H | G | K | W | Y | V | V |
| S106.3-K20 | Q | D | S | T | S | D | L | I | P | A | P | P | L | S | K | V | P | L | Q | Q | N | F | Q | D | N | Q | F | H | G | K | W | Y | V | V |
| S106.3-O19 | Q | D | S | T | S | D | L | I | P | A | P | P | L | S | K | V | P | L | Q | Q | N | F | Q | D | N | Q | F | H | G | K | W | Y | V | V |
| S109.5-L04 | Q | D | S | T | S | D | L | I | P | A | P | P | L | S | K | V | P | L | Q | Q | N | F | Q | D | N | Q | F | H | G | K | W | Y | V | V |
| S109.5-L23 | Q | D | S | T | S | D | L | I | P | A | P | P | L | S | K | V | P | L | Q | Q | N | F | Q | D | N | Q | F | H | G | K | W | Y | V | V |
| S109.6-J11 | Q | D | S | T | S | D | L | I | P | A | P | P | L | S | K | V | P | L | Q | Q | N | F | Q | D | N | Q | F | H | G | K | W | Y | V | V |
| S109.4-A15 | Q | D | S | T | S | D | L | I | P | A | P | P | L | S | K | V | P | L | Q | Q | N | F | Q | D | N | Q | F | H | G | K | W | Y | V | V |
| S140.3-A23 | Q | D | S | T | S | D | L | I | P | A | P | P | L | S | K | V | P | L | Q | Q | N | F | Q | D | N | Q | F | H | G | K | W | Y | V | V |
| S140.1-F09 | Q | D | S | T | S | D | L | I | P | A | P | P | L | S | K | V | P | L | Q | Q | N | F | Q | D | N | Q | F | H | G | K | W | Y | V | V |
| S140.2-P24 | Q | D | S | T | S | D | L | I | P | A | P | P | L | S | K | V | P | L | Q | Q | N | F | Q | D | N | Q | F | H | G | K | W | Y | V | V |
| S140.1-D24 | Q | D | S | T | S | D | L | I | P | A | P | P | L | S | K | V | P | L | Q | Q | N | F | Q | D | N | Q | F | H | G | K | W | Y | V | V |
| S140.3-P07 | Q | D | S | T | S | D | L | I | P | A | P | P | L | S | K | V | P | L | Q | Q | N | F | Q | D | N | Q | F | H | G | K | W | Y | V | V |
| S140.4-O10 | Q | D | S | T | S | D | L | I | P | A | P | P | L | S | K | V | P | L | Q | Q | N | F | Q | D | N | Q | F | H | G | K | W | Y | V | V |
| S140.4-B16 | Q | D | S | T | S | D | L | I | P | A | P | P | L | S | K | V | P | L | Q | Q | N | F | Q | D | N | Q | F | H | G | K | W | Y | V | V |
| S140.2-H04 | Q | D | S | T | S | D | L | I | P | A | P | P | L | S | K | V | P | L | Q | Q | N | F | Q | D | N | Q | F | H | G | K | W | Y | V | V |

| | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 |
|---|---|---|---|---|---|---|---|---|---|---|---|---|---|---|---|---|---|---|---|---|---|---|---|---|---|---|---|---|---|---|---|---|---|---|
| hNGAL wt | G | L | A | G | N | A | I | L | R | E | D | K | D | P | Q | K | M | Y | A | T | I | Y | E | L | K | E | D | K | S | Y | N | V | T | S |
| S67.2-F03 | G | L | A | G | N | R | I | L | R | D | D | Q | H | P | M | N | M | Y | A | T | I | Y | E | L | K | E | D | K | S | Y | N | V | T | S |
| S67.3-C21 | G | L | A | G | N | Y | I | W | R | N | D | R | Y | P | M | Q* | M | Y | A | T | I | Y | E | L | K | E | D | K | S | Y | N | V | T | S |
| S94.2-F05 | G | L | A | G | N | R | I | L | R | D | D | Q | H | P | M | N | M | Y | A | T | I | Y | E | L | K | E | D | K | S | Y | N | V | T | S |
| S94.7-Q13 | G | L | A | G | N | R | I | L | R | D | D | Q | H | P | M | N | M | Y | A | T | I | Y | E | L | K | E | D | K | S | Y | N | V | T | S |
| F92.1-J08 | G | L | A | G | N | R | I | L | R | D | D | Q | H | P | M | N | M | Y | A | T | I | Y | E | L | K | E | D | K | S | Y | N | V | T | S |
| S106.1-N15 | G | L | A | G | N | R | I | L | R | D | D | Q | H | P | M | N | M | Y | A | T | I | Y | E | L | K | E | D | K | S | Y | N | V | T | S |
| S107.4-C16 | G | L | A | G | N | R | I | L | R | D | D | Q | H | P | M | N | M | Y | A | T | I | Y | E | L | K | E | D | K | S | Y | N | V | T | S |
| S106.3-K20 | G | L | A | G | N | R | I | L | R | D | D | Q | H | P | M | N | M | Y | A | T | I | Y | E | L | K | E | D | K | S | Y | N | V | T | S |
| S106.3-O19 | G | L | A | G | N | R | I | L | R | D | D | Q | H | P | M | N | M | Y | A | T | I | Y | E | L | K | E | D | K | S | Y | N | V | T | S |
| S109.5-L04 | G | L | A | G | N | R | I | L | R | D | D | R | H | P | M | N | M | Y | A | T | I | Y | E | L | K | E | D | K | S | Y | N | V | T | S |
| S109.5-L23 | G | L | A | G | N | R | I | L | R | D | D | Q | H | P | M | N | M | Y | A | T | I | Y | E | L | K | E | D | K | S | Y | D | V | T | S |
| S109.6-J11 | G | L | A | G | N | R | I | L | R | D | D | Q | H | P | M | N | M | Y | A | T | I | Y | E | L | K | E | D | K | S | Y | N | V | T | S |
| S109.4-A15 | G | L | A | G | N | R | I | L | R | D | D | Q | H | P | M | D | M | Y | A | T | I | Y | E | L | K | E | D | K | S | Y | N | V | T | S |
| S140.3-A23 | G | L | A | G | N | R | I | L | R | D | D | Q | H | P | M | N | M | Y | A | T | V | Y | E | L | K | E | D | K | S | Y | N | V | T | S |
| S140.1-F09 | G | L | A | G | N | R | I | L | R | D | D | Q | H | P | M | N | M | Y | A | T | I | Y | E | L | K | E | D | K | S | Y | N | V | T | S |
| S140.2-P24 | G | L | A | G | N | R | I | L | R | D | D | Q | H | P | M | D | M | Y | A | T | I | Y | E | L | K | E | D | K | S | Y | N | V | T | S |
| S140.1-D24 | G | L | A | G | N | R | I | L | R | D | D | Q | H | P | M | N | M | Y | A | T | I | Y | E | L | K | E | D | K | S | Y | N | V | T | S |
| S140.3-P07 | G | L | A | G | N | R | I | L | R | D | D | Q | H | P | M | N | M | Y | A | T | I | Y | E | L | K | E | D | K | S | Y | N | V | T | S |
| S140.4-O10 | G | L | A | G | N | R | I | L | R | D | D | Q | H | P | M | N | M | Y | A | T | I | Y | E | L | K | E | D | K | S | Y | N | V | T | S |
| S140.4-B16 | G | L | A | G | N | R | I | L | R | D | D | Q | H | P | M | N | M | Y | A | T | I | Y | E | L | K | E | D | K | S | Y | N | V | T | S |
| S140.2-H04 | G | L | A | G | N | R | I | L | R | D | D | Q | H | P | M | N | M | Y | A | T | I | Y | E | L | K | E | D | K | S | Y | N | V | T | S |

| | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 |
|---|---|---|---|---|---|---|---|---|---|---|---|---|---|---|---|---|---|---|---|---|---|---|---|---|---|---|---|---|---|---|---|---|---|---|
| hNGAL wt | V | L | F | R | K | K | C | D | Y | W | I | A | T | F | V | P | G | S | Q | P | G | E | F | T | L | G | N | I | K | S | Y | P | G | |
| S67.2-F03 | V | I | F | P | H | K | K | C | E | Y | T | I | A | T | F | V | P | G | S | Q | P | G | E | F | T | L | G | N | I | K | S | Y | G | D |
| S67.3-C21 | V | I | F | D | T | K | K | C | E | Y | P | I | A | T | F | V | P | G | S | Q | P | G | E | F | T | L | G | N | I | K | S | Y | R | M |
| S94.2-F05 | V | I | F | P | H | K | K | C | E | Y | T | I | A | T | F | V | P | G | S | Q | P | G | E | F | T | L | G | N | I | K | S | Y | G | D |
| S94.7-Q13 | V | I | F | P | H | K | K | C | E | Y | T | I | A | T | F | V | P | G | S | Q | P | G | E | F | T | L | G | N | I | K | S | Y | G | D |
| F92.1-J08 | V | I | F | P | H | K | K | C | E | Y | T | I | A | T | F | V | P | G | S | Q | P | G | E | F | T | L | G | N | I | K | S | Y | G | D |
| S106.1-N15 | V | I | F | P | H | K | K | C | E | Y | T | I | A | T | F | V | P | G | S | Q | P | G | E | F | T | L | G | N | I | K | S | Y | G | D |
| S107.4-C16 | V | I | F | P | H | K | K | C | E | Y | T | I | A | T | F | V | P | G | S | Q | P | G | E | F | T | L | G | N | I | K | S | Y | G | D |
| S106.3-K20 | V | I | F | P | H | K | K | C | E | Y | T | I | A | T | F | V | P | G | S | Q | P | G | E | F | T | L | G | N | I | K | S | Y | G | D |
| S106.3-O19 | V | I | F | P | H | K | K | C | E | H | T | I | A | T | F | V | P | G | S | Q | P | G | E | F | T | L | G | N | I | K | S | Y | G | D |
| S109.5-L04 | V | I | F | P | H | K | K | C | E | Y | T | I | A | T | F | V | P | G | S | Q | P | G | E | F | T | L | G | N | I | K | S | Y | G | D |
| S109.5-L23 | V | I | F | P | H | K | K | C | E | Y | T | T | A | T | F | V | P | G | S | Q | P | G | E | F | T | L | G | N | I | K | S | Y | G | G |
| S109.6-J11 | V | I | F | P | H | K | K | C | E | Y | T | F | A | T | F | V | P | G | S | Q | P | G | E | F | T | L | G | N | I | K | S | Y | G | D |
| S109.4-A15 | V | I | F | P | H | K | K | C | E | Y | T | I | A | T | F | V | P | G | S | Q | P | G | E | F | T | L | G | N | I | K | S | Y | G | D |
| S140.3-A23 | V | I | S | S | H | K | K | C | E | Y | T | I | A | T | F | V | P | G | S | Q | P | G | E | F | T | L | G | N | I | K | S | Y | G | D |
| S140.1-F09 | V | I | S | S | H | K | K | C | E | Y | T | I | A | T | F | V | P | G | S | Q | P | G | E | F | T | L | G | N | I | K | S | Y | G | D |
| S140.2-P24 | V | I | S | S | H | K | K | C | E | Y | T | I | A | T | F | V | P | G | S | Q | P | G | E | F | T | L | G | N | I | K | S | Y | G | D |
| S140.1-D24 | V | I | L | S | H | K | K | C | E | Y | T | I | A | T | F | V | P | G | S | R | P | G | E | F | T | L | G | N | I | K | S | Y | G | D |
| S140.3-P07 | V | I | F | P | H | K | K | C | E | Y | T | I | A | T | F | V | P | G | S | Q | P | G | E | F | T | L | G | N | I | K | S | Y | G | D |
| S140.4-O10 | V | I | S | S | H | K | K | C | E | Y | T | I | A | T | F | V | P | G | S | Q | P | G | E | F | T | L | G | N | I | K | S | Y | G | D |
| S140.4-B16 | V | I | F | P | H | K | K | C | E | Y | T | I | A | T | F | V | P | G | S | Q | P | G | E | F | T | L | S | D | I | K | S | Y | G | D |
| S140.2-H04 | V | I | L | S | H | K | K | C | E | Y | T | V | A | T | F | V | P | G | S | Q | P | G | E | F | T | L | G | N | I | K | S | Y | G | D |

Fig. 15 (cont.)

| | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 |
|---|---|---|---|---|---|---|---|---|---|---|---|---|---|---|---|---|---|---|---|---|---|---|---|---|---|---|---|---|---|---|---|---|---|---|
| hNGAL wt | L | T | S | Y | L | V | R | V | V | S | T | N | Y | N | Q | H | A | M | V | F | F | K | A | V | S | Q | N | R | E | Y | F | A | I | T |
| S67.2-F03 | K | T | S | Y | L | V | R | V | V | S | T | N | Y | N | Q | H | A | M | V | F | F | K | L | V | E | D | N | A | E | F | F | A | I | T |
| S67.3-C21 | D | T | S | Y | L | V | R | V | V | S | T | N | Y | N | Q | H | A | M | V | F | F | K | Q | V | N | H | N | T | E | H | F | A | I | T |
| S94.2-F05 | K | T | S | Y | L | V | R | V | V | S | T | N | Y | N | Q | Y | A | M | V | F | F | K | L | A | E | D | N | A | E | F | F | A | V | T |
| S94.7-Q13 | K | T | S | Y | L | V | R | V | V | S | T | N | Y | N | Q | H | A | T | V | F | F | K | L | A | E | D | N | A | E | F | F | A | I | T |
| F92.1-J08 | K | T | S | Y | L | V | R | V | V | S | T | N | Y | N | Q | Y | A | V | V | F | F | K | L | A | E | D | N | A | E | F | F | A | I | T |
| S106.1-N15 | K | T | S | Y | L | V | R | V | V | S | T | N | Y | N | Q | H | A | M | V | F | F | K | L | A | E | D | N | A | E | F | F | A | I | T |
| S107.4-C16 | K | T | S | Y | L | V | R | V | V | S | T | N | Y | N | Q | H | A | M | V | F | F | E | L | V | E | D | N | A | G | F | F | A | I | T |
| S106.3-K20 | K | T | S | Y | L | V | R | V | V | S | T | N | Y | N | Q | H | A | V | V | F | F | Q | L | V | E | D | N | A | G | F | F | A | I | T |
| S106.3-O19 | K | T | S | Y | L | V | R | V | V | S | T | D | Y | N | Q | H | A | M | V | F | F | E | L | V | E | D | N | A | G | F | F | A | I | T |
| S109.5-L04 | K | T | S | Y | L | V | R | V | V | S | T | N | Y | N | Q | H | A | T | V | F | F | K | L | A | E | D | N | A | E | F | F | A | I | T |
| S109.5-L23 | K | T | S | Y | L | V | R | V | V | S | T | N | Y | N | Q | H | A | T | V | F | F | K | L | A | G | D | N | A | E | F | F | A | I | T |
| S109.6-J11 | K | T | S | Y | L | V | R | V | V | S | T | N | Y | N | Q | H | A | T | V | F | F | K | L | A | E | D | N | A | E | F | F | A | V | T |
| S109.4-A15 | K | T | S | Y | L | V | R | V | V | S | T | N | Y | N | Q | H | A | T | V | F | F | K | L | A | E | D | N | A | E | F | F | A | I | T |
| S140.3-A23 | K | T | S | Y | L | V | R | V | V | S | T | N | Y | N | Q | Y | A | V | V | F | F | K | L | A | E | D | N | A | E | F | F | A | I | T |
| S140.1-F09 | K | T | S | Y | L | V | R | V | V | S | T | N | Y | N | Q | Y | A | V | V | F | F | K | L | A | E | D | N | A | E | F | F | A | I | T |
| S140.2-P24 | K | T | S | Y | L | V | R | V | V | S | T | D | Y | S | Q | Y | A | V | V | F | F | K | L | A | E | D | N | A | E | F | F | A | I | T |
| S140.1-D24 | K | T | S | Y | L | V | R | V | V | S | T | N | Y | N | Q | Y | A | V | V | F | F | K | L | A | E | D | N | A | E | F | F | A | I | T |
| S140.3-P07 | K | T | S | Y | L | V | R | V | V | S | T | D | Y | N | Q | Y | A | V | V | F | F | K | L | A | E | D | D | A | E | F | F | A | I | T |
| S140.4-O10 | K | T | S | Y | L | V | R | V | V | S | T | D | Y | N | Q | Y | A | V | V | F | F | K | L | A | E | D | N | A | E | F | F | A | I | T |
| S140.4-B16 | K | T | S | Y | L | V | R | V | V | S | T | D | Y | N | Q | Y | A | V | V | F | F | K | L | A | E | D | N | A | E | F | F | A | I | T |
| S140.2-H04 | K | T | S | Y | L | V | R | V | V | S | T | N | Y | N | Q | Y | A | V | V | F | F | K | L | A | E | D | N | A | E | F | F | A | I | T |

| | 137 | 138 | 139 | 140 | 141 | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hNGAL wt | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S67.2-F03 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S67.3-C21 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S94.2-F05 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S94.7-Q13 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| F92.1-J08 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S106.1-N15 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S107.4-C16 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S106.3-K20 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S106.3-O19 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S109.5-L04 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S109.5-L23 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S109.6-J11 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S109.4-A15 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.3-A23 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.1-F09 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.2-P24 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.1-D24 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.3-P07 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.4-O10 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.4-B16 | I | Y | G | R | T | K | E | L | A | S | E | L | K | E | N | F | I | R | F | S | K | S | L | G | L | P | E | N | H | I | V | F | P | V | P | I | D | Q | C | I | D | G |
| S140.2-H04 | I | Y | G | R | T | K | E | L | A | S | E | L | K | E | N | F | I | R | F | S | K | S | L | G | L | P | E | N | H | I | V | F | P | V | P | I | D | Q | C | I | D | G |

\* This glutamine residue was encoded by an amber stop codon.

Fig 18
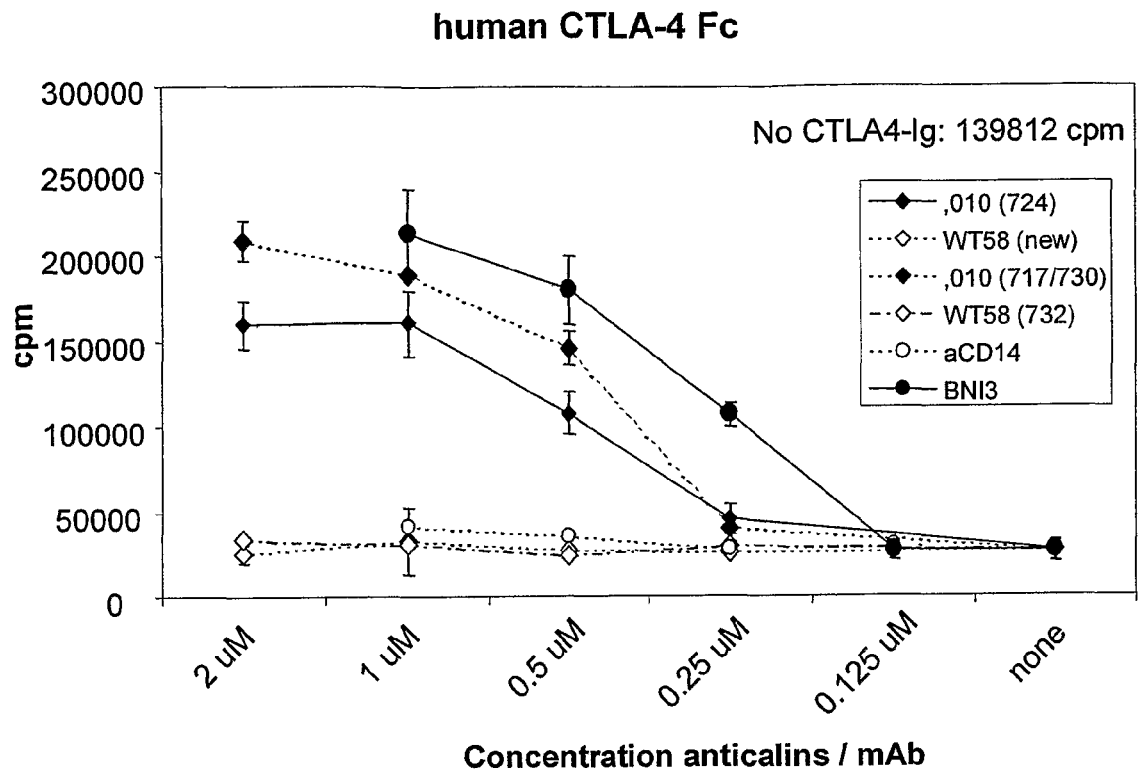
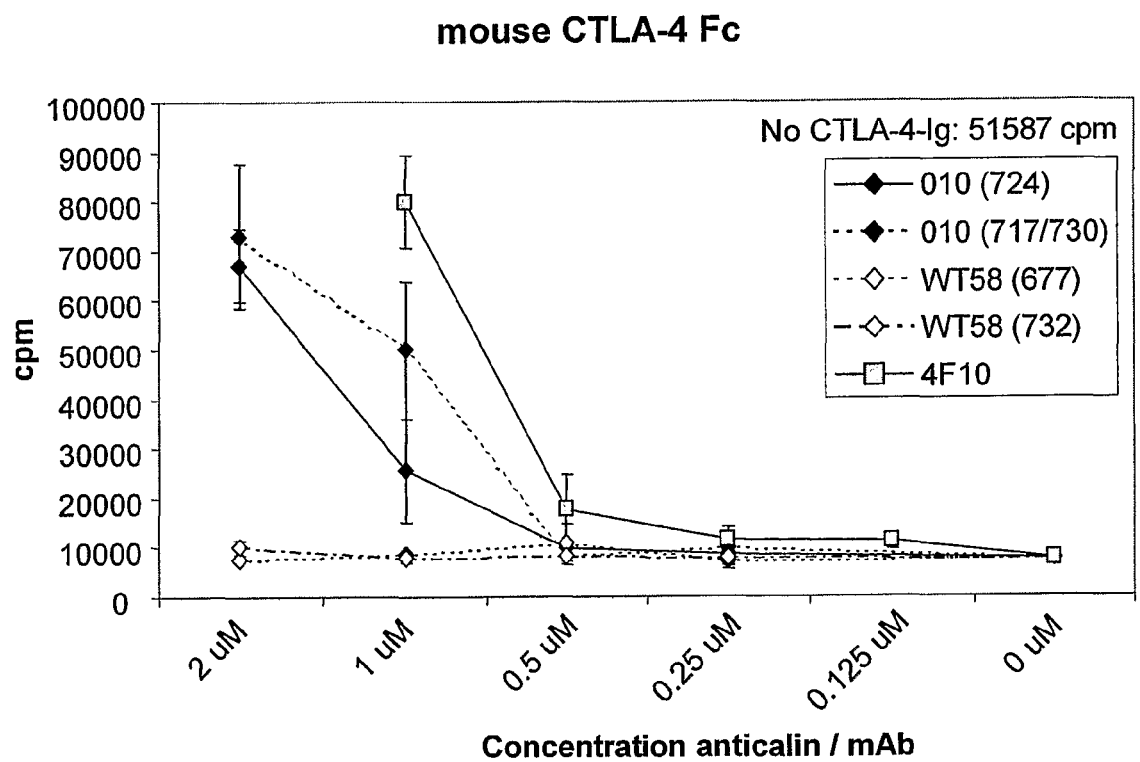

Fig.20

| Tissue | Source | Test Article [S146.4-C10 (phNGAL15)] | | Negative Control Antibody [Isotype-matched hNGALwt_58] | | Assay Control | Positive Control Antibody [Mouse anti-Human CD152 (CLTA-4), clone BN13.1] | Negative Control Antibody MsIgG2a |
|---|---|---|---|---|---|---|---|---|
| | | 40 µg/mL | 5 µg/mL | 40 µg/mL | 5 µg/mL | | 5 µg/mL | 5 µg/mL |
| CD152-expressing cells in cryosections of human tonsil (Positive Control Tissue) | HT662 | 4+ | 4+ | Neg | Neg | Neg | 4+ | Neg |
| CD152-expressing cells in cryosections of human tonsil (Positive Control Tissue) | HT343 | 4+ | 4+ | Neg | Neg | Neg | 4+ | Neg |
| CD152-non-expressing cells in human tonsil (Negative Control Tissue) | HT662 | Neg | Neg | Neg | Neg | Neg | Neg | Neg |
| Adrenal | HT089 | M | M | M | M | M | Neg | Neg |
| Adrenal | HT234 | Neg | Neg | Neg | Neg | Neg | NS | NS |
| Blood Leukocytes | HT536 | Neg | Neg | Neg | Neg | Neg | Neg | Neg |
| Blood Vessels (endothelium) Examined in all tissues | All tissues | Neg | Neg | Neg | Neg | Neg | Neg | Neg |
| Bone Marrow | HT107 | Neg | Neg | Neg | Neg | Neg | M | M |
| Bone Marrow | HT553 | NS | NS | NS | NS | NS | Neg | Neg |
| Brain – cerebrum (cortex) | HT483 | Neg | Neg | Neg | Neg | Neg | Neg | Neg |
| Brain – cerebellum | HT598 | Neg | Neg | Neg | Neg | Neg | Neg | Neg |
| Breast (mammary gland) | HT650 | Neg | Neg | Neg | Neg | Neg | Neg | Neg |
| Eye | HT318 | Neg | Neg | Neg | Neg | Neg | Neg | Neg |
| Gastrointestinal Tract – colon (large intestine) | HT484 | Neg | Neg | Neg | Neg | Neg | Neg | Neg |
| Gastrointestinal Tract – (esophagus) | HT358 | Neg | Neg | Neg | Neg | Neg | Neg | Neg |
| Gastrointestinal Tract – small intestine | HT035 | Neg | Neg | Neg | Neg | Neg | Neg | Neg |
| Gastrointestinal Tract – small intestine | HT460 | Neg | Neg | Neg | Neg | Neg | Neg | Neg |

Legend: ± = equivocal, 1+ = weak, 2+ = moderate, 3+ = strong, 4+ = intense, Neg = Negative, M = Missing, NS = not stained

Fig.20 (cont.)

| Tissue | Source | Test Article [S140.4-O10 (phNGAL15)] | | Negative Control Antibody [Isotype-matched hNGALwt_58] | | Assay Control | Positive Control Antibody [Mouse anti-Human CD152 (CLTA-4), clone BN13.1] | Negative Control Antibody MsIgG2a |
|---|---|---|---|---|---|---|---|---|
| | | 40 µg/mL | 5 µg/mL | 40 µg/mL | 5 µg/mL | | 5 µg/mL | 5 µg/mL |
| Gastrointestinal Tract – (stomach) | HT121 | Neg | Neg | Neg | Neg | Neg | Neg | Neg |
| Heart | HT265 | Neg | Neg | Neg | Neg | Neg | Neg | Neg |
| Kidney | HT266 | Neg | Neg | Neg | Neg | Neg | Neg | Neg |
| Kidney Mononuclear cells, interstitial, inflammatory (membrane, rare) | HT268 | 2-3+ (very rare) | Neg | Neg | Neg | Neg | 4+ | Neg |
| Other elements | | Neg | Neg | Neg | Neg | Neg | Neg | Neg |
| Liver | HT264 | Neg | Neg | Neg | Neg | Neg | Neg | Neg |
| Lung | HT267 | Neg | Neg | Neg | Neg | Neg | Neg | Neg |
| Lymph Node | HT892-1 | Neg | Neg | Neg | Neg | Neg | Neg | Neg |
| Ovary | HT661 | Neg | Neg | Neg | Neg | Neg | Neg | Neg |
| Fallopian Tube (oviduct) | HT484 | Neg | Neg | Neg | Neg | Neg | Neg | Neg |
| Pancreas | HT121 | Neg | Neg | Neg | Neg | Neg | Neg | Neg |
| Parathyroid | HT493 | Neg | Neg | Neg | Neg | Neg | Neg | Neg |
| Peripheral Nerve | HT185 | Neg | Neg | Neg | Neg | Neg | Neg | Neg |
| Pituitary | HT698 | Neg | Neg | Neg | Neg | Neg | Neg | Neg |
| Placenta | HT651 | Neg | Neg | Neg | Neg | Neg | Neg | Neg |
| Prostate | HT578 | Neg | Neg | Neg | Neg | Neg | Neg | Neg |
| Salivary Gland | HT108 | Neg | Neg | Neg | Neg | Neg | Neg | Neg |
| Skin | HT545 | Neg | Neg | Neg | Neg | Neg | Neg | Neg |
| Spinal Cord | HT435 | Neg | Neg | Neg | Neg | Neg | Neg | Neg |
| Spleen Mononuclear cells, white pulp (membrane, frequent) | HT337 | 4+ | 4+ | Neg | Neg | Neg | 4+ | Neg |
| Other elements | | Neg | Neg | Neg | Neg | Neg | Neg | Neg |

Legend: ± = equivocal, 1+ = weak, 2+ = moderate, 3+ = strong, 4+ = intense, Neg = Negative, M = Missing, NS = not stained

Fig.20 (cont.)

| Tissue | Source | Test Article [S146.4-O10 (phNGAL15)] | | Negative Control Antibody [Isotype-matched hNGALwt_58] | | Assay Control | Positive Control Antibody [Mouse anti-Human CD152 (CLTA-4), clone BN13.1] | Negative Control Antibody MsIgG2a |
|---|---|---|---|---|---|---|---|---|
| | | 40 μg/mL | 5 μg/mL | 40 μg/mL | 5 μg/mL | | 5 μg/mL | 5 μg/mL |
| Striated (Skeletal) Muscle | HT266 | Neg | Neg | Neg | Neg | Neg | Neg | Neg |
| Testis | HT519 | Neg | Neg | Neg | Neg | Neg | Neg | Neg |
| Thymus | HT873 | Neg | Neg | Neg | Neg | Neg | Neg | Neg |
| Thyroid | HT365 | Neg | Neg | Neg | Neg | Neg | Neg | Neg |
| Tonsil Mononuclear cells, follicular>>interfollicular (membrane) Other elements | HT664 | 4+ (very rare) Neg | 4+ (very rare) Neg | Neg Neg | Neg Neg | Neg Neg | 4+ (occas) Neg | Neg Neg |
| Ureter | HT532 | Neg | Neg | Neg | Neg | Neg | Neg | Neg |
| Urinary Bladder | HT558 | Neg | Neg | Neg | Neg | Neg | Neg | Neg |
| Uterus – body (endometrium) | HT881 | Neg | Neg | Neg | Neg | Neg | Neg | Neg |
| Uterus - cervix | HT473 | M | M | M | M | M | Neg | Neg |
| Uterus - cervix | HT474 | Neg | Neg | Neg | Neg | Neg | NS | NS |

Legend: ± = equivocal, 1+ = weak, 2+ = moderate, 3+ = strong, 4+ = intense, Neg = Negative, M = Missing, NS = not stained

COMPOUND WITH AFFINITY FOR THE CYTOTOXIC T LYMPHOCYTE-ASSOCIATED ANTIGEN (CTLA-4)

This application claims the benefit of priority of U.S. provisional application No. 60/631,253 filed Nov. 26, 2004, U.S. provisional application No. 60/631,200 filed Nov. 26, 2004, U.S. provisional application No. 60/631,202 filed Nov. 26, 2004, U.S. provisional application No. 60/631,227 filed Nov. 26, 2004, U.S. provisional application No. 60/522,970 filed Nov. 29, 2004, U.S. provisional application No. 60/680,067 filed May 11, 2005, and U.S. provisional application No. 60/679,811 filed May 11, 2005, the contents of each being hereby incorporated by reference in its entirety for all purposes.

The present invention relates to a compound with affinity for the cytotoxic T lymphocyte associated antigen (CTLA-4), wherein the compound exhibits a synergistic mode of action in that the compound: (a) increases T cell priming or T cell expansion or the generation of memory T cells by blocking of CTLA-4, and (b) enhances effector T cell activity in tumor tissue or lymphoid tissue by blocking of CTLA-4. The compound of the invention can be a protein, a small organic molecule, a peptide, or a nucleic acid. The invention also relates to a pharmaceutical composition comprising such a compound as well as to various pharmaceutical uses of such a compound, for example, for the prevention and/or treatment of cancer, an auto-immune disease or an infectious disease.

The interaction of antigen presented in the context of MHC class II to the T Cell Antigen Receptor Complex (TCR) provides the primary signal to the Helper T Cell to initiate clonal proliferation. Optimal T cell activation, however, requires a co-stimulatory signal in addition to the engagement of the TCR. Although several co-stimulatory molecules have been implicated in initiating the "second signal", it has become apparent that one of the major signals is provided by the interaction of CD28 with B7 molecules (CD80 and CD86) presented on the surface of the antigen presenting cell.

Cell surface CD28 is a 201 amino acid glycoprotein member of the Ig-superfamily of proteins (Aruffo and Seed., Proc. Natl. Acad. Sci. U.S.A. 84:8573 (1987)). It is found naturally as a homodimer and expressed constitutively on the surface of 80% of human T cells (all CD4.sup.+ cells and on about 50% of the CD8.sup.+ cells) and on virtually all murine T cells (Linsley and Ledbetter, Ann. Rev. Immunol. 11: 191-212, (1993)). Engagement of CD28 by its natural ligand B7-1 or B7-2 (CD80, CD86) results in a second signal to the T cell and an increase of IL-2 production along with down-regulation of the CD28 with respect to mRNA levels and cell surface expression.

The second signal is believed to be crucial for the commitment of antigen specific T cell to proliferate. Interference with this second signal in the presence of the first signal (TCR signal) results in antigen specific T cell anergy (unresponsiveness) (Linsley et al., J. Exp. Med. 174:561-569 (1991), Linsley et al., Science 257:792-795 1992). During the period that CD28 is down-modulated, a closely related glycoprotein, CTLA-4, is concomitantly up-regulated (Freeman et al., 1992). It is generally thought that CD28 delivers the positive costimulatory signal for growth and differentiation, while CTLA-4 is responsible for a subsequent negative signal of the cellular activation events (for a review see Lenschow et al., Annu. Rev. Immunol. 14, 233-258 (1996)). Both CD28 and CTLA-4 bind to the B7 family of proteins, most notably B7-2 and B7-1. With regard to B7-1, it is known that CTLA-4 binds with a 20-100 fold higher affinity than CD28 (Linsley et al., J. Exp. Med. 174:561-569, (1991)). Freshly isolated human and murine B cells express low levels of B7-2 but not B7-1, however the levels of both B7 molecules are up-regulated upon activation. Non-activated T cells express CD28 but not CTLA-4. Rapid up-regulation of CTLA-4 mRNA in T cells can be detected within 1 hour of TCR engagement with a peak around 24 hours (Lindsten T et al J Immunol. (1993) 151(7): 3489-99) whereas CTLA-4 protein expression on the cell surface cannot readily be detected until 24-48 hours after activation (Walunas T L et al., Immunity (1994) 1(5):405-13). In addition, cell surface CTLA-4 expression is tightly regulated through intracellular localization, rapid endocytosis into endosomal compartments and a short protein half live (Schneider H et al J Immunol. (1999) 163(4):1868-79). Re-localization from intracellular vesicles to the immunologic synapse has been observed in vitro and correlated with the strength of the TCR stimulation (Egen J G and Allison J P Immunity (2002) 16(1):23-35). Regulatory T cells, a distinct cell population that contribute to controlling effector T cells in trans, constitutively express CTLA-4 (Takahashi T et al J. Exp. Med. 2000 192(2):303-10, Read S et al J. Exp. Med. 2000 192(2):295-302)

CTLA-4 deficient mice develop a massive and lethal lymphoproliferative disease that is more severe than similar phenotypes observed in lpr mice, gld mice, mice with a T cell specific defect in TGFβ signal transduction or targeted deletion of the inhibitory molecule PD-1 (Chambers C A et al Annu. Rev. Immunol. 2001; 19:565-94). Absence of CTLA-4 results in an activated phenotype of peripheral T cells (Waterhouse P et al Science (1995) 10; 270(5238):985-8, Tivol E A et al Immunity (1995) 3(5):541-7) whereas thymocyte development appears to be normal (Chambers C A et al Proc. Natl. Acad. Sci. USA. (1997) 94(17):9296-301). From these observations it was concluded that CTLA-4 is necessary to regulate peripheral T cell tolerance and homeostasis of CD4$^+$ and CD8$^+$ T cells as polyclonal expansion of both populations occurs. The absence of CTLA-4 is most evident during the secondary responses in CTLA-4$^{-/-}$ TCR-transgenic models (Chambers C A et al Proc. Natl. Acad. Sci. USA. (1999) 96(15): 8603-8).

Several molecular mechanisms by which CTLA-4 inhibition occurs have been proposed including direct effects on phosphorylation levels, indirect effects due to competition with CD28 for ligand, sequestration of signalling molecules or disruption of signalling complexes (Chambers C A et al Annu Rev Immunol. 2001; 19:565-94, Egen J G et al Nat Immunol. (2002) 3(7):611-8, Chikuma S and Bluestone J A. Mol Interv. 2002 2(4):205-8). Although the identity of the phosphatases involved are still debated, decreased phosphorylation of proximal TCR signalling molecules like CD3ζ, EKR and JUN-N-terminal kinase have been observed when CTLA-4 cross-linking was used experimentally as CTLA-4 agonist. CTLA-4 might function at least in part by competing with CD28 for B7 ligands and thereby attenuating co-stimulatory signals indirectly particularly when B7 levels are low. Direct signalling through the tail of CTLA-4 appears to be necessary when B7 levels are high which is further supported by the fact that a tailless CTLA-4 mutant on the cell surface of transgenic T cells in CTLA-4–/– mice delayed but did not prevent T cell activation and lymphoproliferation. The third model proposes that CTLA-4 physically disturbs the assembly or organization of molecules in the immunologic synapse. Formation of stable CTLA-4/B7 lattices due to the possible interaction of one CTLA-4 molecule with two B7 dimers as suggested by crystal structures may disturb the organized assembly of key components involved in the generation of TCR/CD28 signals.

Based on the differential timing of CTLA-4 and CD28 cell surface expression it was initially postulated that CD28 engagement allowed initiation and CTLA-4 engagement contributed to the termination of immune responses. In the meantime, the majority of in vitro data point to an inhibitory role of CTLA-4 in the early stage of T cell activation. Two extreme situations could be envisioned where B7 levels are either low or high. When B7 levels are low and TCR signals are weak, low amounts of CTLA-4 (non detectable by cell surface FACS but RT-PCR) might be sufficient to set a threshold for T cell activation by reducing co-stimulation. Regulating the threshold of activation might play a role in maintaining peripheral tolerance of T cells with specificities for autoantigens when T cells encounter selfantigens. When B7 levels are high and TCR signals are strong the levels of CTLA-4 induced after activation (detectable by cell surface FACS) may be able to attenuate the response of activated T cells by affecting the expansion phase. The mechanisms by which CTLA-4 regulates polyclonal T cell responses are likely to be complex but appear to limit the clonal representation of T cells with high affinity TCRs.

In addition, CTLA-4 expression by regulatory T cells might contribute to their immunomodulatory activity and affect effector T cells (Thompson C and Powrie F 2004 Curr. Opin. Pharmacol. 4:408-14). For example, cutaneous T cell lymphoma (CTCL) has been identified as a disease mediated by clonal CD4 T cells exhibiting a regulatory phenotype. CTLA-4 expression by CTCL cells in fact might contribute to the immunosuppression observed in the disease (Berger C L et al 2005 Blood 105: 1640-47). CTLA-4 expression by malignant cells outside the lymphoid cell lineage has been described as well (Pistillo M P et al 2003 Blood 101: 202-209, Contardi E et al., 2005 Int J Cancer 117(4):538-50).

CTLA-4 blockade with monoclonal antibodies or antibody fragments has been shown to lead to the rejection of a number of immunogenic transplantable tumor cell lines including colorectal carcinoma, renal carcinoma, lymphoma and fibrosarcoma cell lines (see for example, U.S. Pat. No. 6,682,736, US patent application 2002/0086014 or International patent application WO 01/14424). Less immunogenic tumor cell lines required concurrent combination therapy with a tumor vaccine, low dose of chemotherapy or surgical resection. The anti-tumor response elicited by CTLA-4 blockade is directed also towards normal tissue-derived proteins as autoimmune reactions were observed in mouse tumor models (B16 melanoma, TRAMP tumor cell) and clinical trials. Recent phase I and II studies with human monoclonal antibodies are encouraging and the concurrent development of autoimmune reactions appears to be clinically manageable and might even correlate with therapeutic efficacy (Phan G Q et al., Proc. Natl. Acad. Sci USA 2003 100: 8372-77, Sanderson K et al., 2005 J. Clin. Oncol. 23: 741-50, Attia P et al., 2005 J. Clin. Oncol. 23: 6043-53). On the other hand, recent results support the notion that enhanced tumor immunity through CTLA-4 blockade does not necessarily have to be linked with increased autoimmunity (Hodi F S et al Proc. Natl. Acad. Sci USA 2003 100: 4712-17, Lute K D et al Blood. (2005) 106 (9):3127-33). In addition to the application in cancer therapy, the use of CTLA-4 binding immunoglobulins for the treatment of infectious diseases and or auto-immune diseases is subject of intensive research.

However, antibodies and fragments thereof may not be suitable for all potential applications. One limiting factor may be their rather large molecular size, which is the case not only for intact antibodies but also for their antigen-binding fragments such as Fab fragments.

For this reason, alternatives to CTLA-4 blocking antibodies have been considered soon after the therapeutic potential of these antibodies emerged. International patent application WO 90/33770 is generally directed to ligands for T cell surface molecules, especially CTLA-4, which induces antigen specific apoptosis of activated T cells. Isolated peptides containing CTLA-4 fragments, constituting the epitope for such binding, are also disclosed and claimed. U.S. Pat. No. 6,337,316 discloses peptidometics capable of inhibiting CD28 and/or CTLA-4 interaction with CD80 (B7-1) and CD86 (B7-2) and having the core amino acid sequence Leu-Met-Tyr-Pro-Pro-Tyr-Tyr (SEQ ID NO: 80).

Despite these approaches, it would still be desirable to have further alternatives to antibodies that are able to bind CTLA-4, for example for blocking the CTLA-4 interaction, and can be used in pharmaceutical applications as described above. It would also be desirable to have a compound that has an improved efficacy. Accordingly, it is an object of the present invention to provide such compounds.

In one aspect of the invention, such a compound is a compound with affinity for the cytotoxic T lymphocyte-associated antigen (CTLA-4), wherein the compound:

(a) increases T cell priming or T cell expansion or the generation of memory T cells by blocking of CTLA-4, and (b) enhances effector T cell activity in tumor tissue or lymphoid tissue by blocking of CTLA-4.

This means such a compound of the invention has a "synergistic" or dual mode of action as it acts not only by blocking CTLA-4 binding but is also able—in contrast to intact antibodies, for example, to efficiently infiltrate into/penetrate into affected tissue.

In another aspect, the compound of the invention is a compound with affinity for the cytotoxic T lymphocyte-associated antigen (CTLA-4), wherein the compound:

(a) is fused or conjugated to a toxin and (b) (upon binding to CTLA-4) leads to a depletion of activated T cells or to a depletion of tumor cells over-expressing CTLA-4 or to a depletion of regulatory T cells.

In some embodiments, the compound as described here has the effect that the T cell priming or T cell expansion or the generation of memory T cells is in lymphoid tissue. In other embodiments, the compound is also or alternatively effective in that the enhancement of effector T cell activity is in tumor tissue.

Any compound that fulfils the above criteria of a) increasing T cell priming or T cell expansion or the generation of memory T cells by blocking of CTLA-4, and (b) enhancing effector T cell activity in tumor tissue or lymphoid tissue by blocking of CTLA-4 is encompassed in the present invention. Examples of such compounds are proteins, small organic molecules, peptides, or nucleic acids. In this conjunction it should be noted that the compound of the invention may bind any CTLA-4 molecule of mammal origin, including, but not limited to, human, murine, rat, feline, canine, simian or pongidian origin. A compound of the invention may only bind CTLA-4 of one species with detectable affinity and thus can be specific, for example, for human or murine CTLA-4. Alternatively, a CTLA-4 binding compound as described herein may also show species cross-reactivity and thus bind CTLA-4 of at least two different species, for example, human and murine CTLA-4 with detectable affinity The term "organic molecule" as used in the present application preferably means an organic molecule comprising at least two carbon atoms, but not more than 7 rotatable carbon bonds having a molecular weight between 100 and 2000 Dalton, preferably 1000 Dalton and a molecule including one or two metal atoms.

In case, the compound is a nucleic acid, it can be an antisense RNA, a siRNA, a microRNA or a nucleic acid (DNA) aptamer, for example.

In case, the compound is a protein, the protein is preferably generated from a scaffold using combinatorial or evolutionary methods such as phage display which are well know to the skilled person. Thus, in exemplary embodiments, the compound is a mutein derived from a (polypeptide) scaffold, wherein the scaffold is a naturally occurring polypeptide which as such does not have any binding activity against CTLA-4 but is subjected to mutagenesis and subsequently presented to CTLA-4 in order select muteins of this polypeptide that have the desired binding activity.

Examples of useful scaffolds include those scaffolds described in US patent application 2005/0089932 or U.S. Pat. No. 6,682,736, the contents of both of which is incorporated by reference herein. Another example of suitable scaffolds are members of the lipocalin protein family as described in the international patent applications WO 99/16873, WO 00/75308, WO 03/029471, WO 03/029462, WO 03/029463, WO 2005/019254, WO 2005/019255 or WO 2005/019256, for instance. The content of these PCT applications is incorporated in their entirety by reference herein.

In accordance with the above, scaffolds besides members of the lipocalin family include, but are not limited to, a EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Diabodies" (Holliger et al. "'Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, a adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotechnol) (Nat Biotechnol. 2005 Nov. 20 edition, e-published before print); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat. Biotechnology. 2005 Nov. 20 edition, e-published before print.

As mentioned above, in certain embodiments of the invention the compound is a mutein of the member of the lipocalin protein family. In some of these embodiments, the open end of the β-barrel structure of the lipocalin fold (which encompasses the natural ligand binding site of the lipocalin family) is used to form the CTLA-4 binding site.

The term lipocalin fold is used according to the definition, e.g., by Flower, D. R. Biochem. J. 318, 1-14 3 (1996) to describe the typical three-dimensional lipocalin structure which is characterized by a conserved β-barrel made of a cylindrically closed β-sheet of eight antiparallel strands, as a central motif, wherein at the open end of the barrel the β-strands are connected in a pairwise manner by four loops so that the binding pocket is formed. Accordingly, such a mutein has a cylindrical β-pleated sheet super-secondary structural region comprising eight β-strands connected in a pair-wise manner by four loops at one end to define thereby a binding pocket. In muteins of this kind, the four loops that define the binding pocket may correspond to those segments which comprise amino acids 28-45, 58-69, 86-99, and 115-129 of the linear polypeptide sequence of the bilin-binding protein of *Pieris brassicae*, wherein at least one amino acid of each of at least three of said four loops comprising said amino acids 28-45, 58-69, 86-99, and 115-129 has been mutated, and wherein said mutein is effective to bind CTLA-4 with determinable affinity. If, for example, human apolipoprotein D is selected as scaffold, these four peptide loops may include the amino acid positions 28 to 44, 59 to 70, 85 to 98 and 113 to 127 of the wildtype sequence of human apolipoprotein D. Thus, CTLA-4 binding muteins of the invention belong to the class of lipocalin muteins which are also known under their trade name Anticalins®, which exhibit, like antibodies, specific binding characteristics for a given ligand and that are obtainable starting from polypeptides of the lipocalin family which are mutated in those four segments that form the conventional binding site of the lipocalins cf. German Offenlegungsschrift DE 197 42 706, the international patent publication WO 99/16873, Beste et al., Proc. Natl. Acad. Sci. USA, 96 (1999) 1898-1903, or Skerra, Reviews in Molecular Biotechnology 74, (2001), 257-275).

In other embodiments, for example, when human tear lipocalin, Von Ebners gland protein 2 or the Major allergen Can f1 precursor of dog (ALL 1) is used for the generation of CTLA-4 binding muteins, the end of the β-barrel structure that is located opposite of the natural lipocalin binding pocket, is employed for mutagenesis of the scaffold. In such a mutein, the binding site is formed by the N-terminal peptide stretch as well as the three peptide loops BC, DE, and FG as defined by Flower, D. R. *Biochem. J.* 318, 1-14 3 (1996) or international patent application WO 2005/019256. In exemplary embodiments of these muteins, the four loops are formed by the sequence positions 7-14, 43-49, 70-77, and 87-97 of the linear polypeptide sequence of human tear lipocalin (see international patent applications WO 2005/019255 or WO 2005/019256 in this regard). In preferred embodiments of muteins using this binding site, the CTLA-4 binding mutein is subjected to mutagenesis (or comprises after mutagenesis mutations) at any two or more of the sequence positions that correspond to sequence positions 8, 9, 10, 11, 12, 13, 43, 45, 47, 70, 72, 74, 75, 90, 92, 94, and 97 of the linear polypeptide sequence of human tear lipocalin.

The lipocalin that is used as a scaffold can be, but is not limited to, the bilin binding protein of *Pieris brassicae*

(SWISS-PROT Data Bank Accession Number P09464), human tear lipocalin (SWISS-PROT Data Bank Accession Number M90424), human apolipoprotein D (SWISS-PROT Data Bank Accession Number P05090), the retinol binding protein (RBP) (for example of human or porcine origin, SWISS-PROT Data Bank Accession Number of the human RBP: P02753, SWISS-PROT Data Bank Accession Number of the porcine RBP P27485), human neutrophil gelatinase-associated lipocalin (hNGAL, SWISS-PROT Data Bank Accession Number P80188), rat $\alpha_2$-microglobulin-related protein (A2m, (SWISS-PROT Data Bank Accession Number P31052), and mouse 24p3/uterocalin (24p3, (SWISS-PROT Data Bank Accession Number P11672), Von Ebners gland protein 2 of *Rattus norvegicus* (VEG protein 2; SWISS-PROT Data Bank Accession Number P41244), Von Ebners gland protein 2 of *Sus scrofra* (pig) (LCN1; SWISS-PROT Data Bank Accession Number P53715), the Major allergen Can f1 precursor of dog (ALL 1, SWISS-PROT Data Bank Accession Number O18873), insecticyanin A or insecticyanin B of the tobacco hawkmoth *Manducta sexta* (SWISS-PROT Data Bank Accession Number P00305 and Q00630, respectively). The generation of CTLA-4 binding muteins of the invention can be carried out in accordance with procedures that are well known to the person skilled in the art. The generation of lipocalin muteins that are based on the above-mentioned lipocalin scaffolds and that have affinity towards a given (prescribed) target are described in detail, for example, in the above-mentioned international patent applications WO 99/16873, WO 00/75308, WO 03/029471, WO 03/029462, WO 03/029463, WO 2005/019254, WO 2005/019255 or WO 2005/019256.

If human tear lipocalin, Von Ebners gland protein 2 or the Major allergen Can f1 precursor of dog (ALL 1) are used for the generation of CTLA-4 binding muteins and it is desired to use the classical ligand binding site of the lipocalin fold for this purpose, the scaffold can be subjected to mutagenesis at least two sequence positions at any of the sequence positions 24-36, 53-66, 79-84, and 103-110 of the linear polypeptide sequence of mature wild type human tear lipocalin. In some of these embodiments, the CTLA-binding mutein is subject to mutagenesis or comprises amino acid mutations at any two or more of the sequence positions that correspond to sequence positions 25, 26, 27, 28, 29, 30, 31, 32, 33, 56, 57, 58, 83, 105, 106, 108 and 109 of the linear polypeptide sequence of human tear lipocalin.

In a further embodiment a mutein of the invention is derived from a protein selected from the group consisting of human neutrophil gelatinase-associated lipocalin (hNGAL), rat $\alpha_2$-microglobulin-related protein (A2m) and mouse 24p3/uterocalin (24p3), wherein said mutein has binding specificity for the cytotoxic T lymphocyte-associated antigen (CTLA-4) and, wherein said mutein:

(a) comprises amino acid replacements at least one of the sequence position corresponding to sequence positions 33 to 54, 66 to 83, 94 to 106, and 123 to 136 of wild type polypeptide sequence of mature hNGAL, and (b) binds human CTLA-4 with a $K_D$ of 50 nM or less.

Accordingly, the muteins of this embodiment of the present invention represent a specific selection of the muteins of neutrophil gelatinase-associated lipocalin (hNGAL), rat $\alpha_2$-microglobulin-related protein (A2m) and mouse 24p3/uterocalin (24p3) that are able to bind proteins and that have been generally disclosed in the international patent application WO 03/029463.

In this conjunction it is noted that the CTLA-binding muteins described herein, do not necessarily have to exercise the above-mentioned dual functionality of (a) increasing T cell priming or T cell expansion or the generation of memory T cells by blocking of CTLA-4, and (b) enhancing effector T cell activity in tumor tissue or lymphoid tissue by blocking of CTLA-4 in order to be biologically active. Rather it is sufficient that the mutein is able to bind CTLA-4 and that the desired biochemical or therapeutic effect is achieved, irrespective of the mode of action. Accordingly, the present invention encompasses all CTLA-4 lipocalin muteins that are described here, irrespective of whether or not they show the above-mentioned dual mode of action. In this conjunction it is also noted that these lipocalin muteins may either bind only CTLA-4 of one species or may exhibit cross-reactivity and thus bind CTLA-4 of at least two different species. In some embodiments a compound/mutein of the invention blocks or interferes with the interaction between CTLA-4 and at least one of its physiological ligands CD80 (B7-1) or CD86 (B7-2) or any other physiological ligand, including presently unknown physiological ligands. In these and other embodiments the mutein of the invention may bind human CTLA-4 with a $K_D$ of 25 nM or less. In addition, the mutein of the invention binds murine CTLA-4 with a $K_D$ of 200 nM or less, with a $K_D$ of 100 nM or less. Accordingly, in contrast to antibodies that have been used so far for binding CTLA-4 and thereby preferably blocking the CTLA-4 interaction with the ligands of the B7 family, muteins of the present invention possess in some embodiments cross-reactivity between human and murine CTLA-4. This provides a clear benefit in preclinal studies, in particular if the human neutrophil gelatinase associated lipocalin (hNGAL) is used for the generation of CTLA-4 binding lipocalin muteins and might allow to identify therapeutic approaches that will be most effecacious in human.

The specificity of binding can be expressed by the cross-reactivity of a lipocalin mutein of the invention as follows:

$$\text{ratio } r = \frac{K_D \text{ for the complex between mutein and human } CTLA-4}{K_D \text{ for the complex between mutein and murine } CTLA-4}$$

In some embodiments, the ratio r has a value of 20 or less, of 1 or less, or a value of 0.5 or less.

The CTLA-4 binding mutein comprises in some embodiments an amino acid replacement at one or more of the sequence positions, which correspond to the sequence positions 40 to 50, 70 to 79, 101 to 103, and 125 to 132 of the mature wild type hNGAL.

In this connection, it is noted that the amino acid positions in the proteins A2m and 24p3 which are subjected to mutagenesis in the present invention are obtained from an alignment of the amino acid sequences of hNGAL, A2m, and 24p3. In the protein A2m, which has the same number of amino acid residues (178) as hNGAL, the sequence positions which are used for the mutagenesis are identical to the positions selected in hNGAL, namely sequence positions 33 to 54, 66 to 83, 94 to 106, and 123 to 136 of hNGAL. For 24p3, the corresponding sequence positions are the sequence positions 33 to 54, 66 to 85, 96 to 108, and 125 to 138. Thus, the amino acid positions which are subjected to mutagenesis are distributed across four sequence segments corresponding to four loops in the three-dimensional structure of hNGAL, A2m, and 24p3.

The number of the segments (loops) defined above which are used for mutagenesis can vary. It is not necessary to mutate all four of these loops altogether, for example in a concerted mutagenesis. But it is also possible to subject only one, two or three of the loops to mutagenesis in order to generate a mutein having affinity to CTLA-4.

In some embodiments, the mutein comprises amino acid replacements at least any 5, 8, 12, or 16 of the sequence positions, which correspond to sequence positions 40, 42, 44, 46, 47, 49, 50, 70, 72, 73, 77, 79, 101, 102, 103, 125, 127, 128, 130, and 132 of the wild type sequence of hNGAL. In other embodiments, a mutein may comprise amino acid replacements, compared to the wild type sequence of hNGAL, A2m or 24p3, at all 20 of the above given sequence positions.

In embodiments where the CTLA-4 binding mutein is derived from hNGAL, the mutein can comprise a Ser residue at sequence position 71 of the wild type sequence of hNGAL. In addition or alternatively, such an hNGAL mutein can comprise a Ser residue at sequence position 72 of the wild type sequence of hNGAL.

The binding site of the lipocalin scaffolds used in some embodiments herein, i.e. of neutrophil gelatinase-associated lipocalin (hNGAL), rat $\alpha_2$-microglobulin-related protein (A2m) and mouse 24p3/uterocalin, (24p3) can accommodate a rather large number of amino acid substitutions, both with respect to sequence position and to the side chain at a specific position, without losing its ability of binding CTLA-4 (cf., FIG. 15 in this regard).

For instance, in hNGAL derived muteins of the invention a Ser, Leu, Val, His, Ile or Thr residue can be present at sequence position 71 of the wild type sequence of the mature hNGAL. In other CTLA-4 binding hNGAL muteins a hydrophilic amino acid, for example Thr or Ser, or a Pro residue can be present at sequence position 72 of hNGAL. Other examples of possible amino acid substitutions in the 4 loop regions that form the binding site are the replacement of the Lys residue at position 50 of hNGAL by a Glu, Gln or Asp residue, the replacement of the Lys residue at position 46 by Gln or Arg residue, replacement of Trp at position 79 by a Thr or a Pro residue, then replacement of Gly at position 102 by an Asp or a Met residue, the replacement of Ala at position 125 by a Leu or Gln residue or the replacement of Arg at position 130 by an Ala or Thr residue, to name only a few illustrative examples in case hNGAL is used as scaffold for the generation of CTLA-4 binding muteins (cf., also FIG. 15).

In some embodiments of the inventions, CTLA-4-binding hNGAL muteins comprise, compared to the sequence of the hNGAL wild type amino acid sequence, at least one, 5, 8, 10, 12, 14 or 16 amino acid replacements selected from the group consisting of (40)A→R or Y, (42)L→W, (44)E→D or N, (46)K→Q or R, (47)D→H or Y, (49)Q→M, (50)K→Q or N or D, (70)L→I, (71)F→S or L, (72)R→S or P or D, (73)K→H or T, (77)D→E, (78)Y or H, (79)W→T or P, (80)I→T or F or V, (88)Q→R, (96)N→D, (101)P→G or R, (102)G→D or M, (103)L→K or D, (124)K→E or Q, (125)A→L or Q, (126) V→A, (127)S→E or N or G, (128)Q→D or H, (129)N→D, (130)R→A or T, (131)E→G, (132)Y→F or H, and (135) I→V.

In addition to the above mutations, an hNGAL mutein described herein may further comprise one or more of the amino acid replacements selected from the group consisting of Glu28→His, Cys87→Ser, and Thr145→Ala. A further mutation that can be present in an hNGAL mutein is having an Ala residue at the sequence position corresponding to sequence position 81 and/or sequence position 125, or sequence position 134 of hNGAL.

In addition, it has been surprisingly discovered in the present invention that the sequence position 114 in hNGAL (or the corresponding position in A2m and 24p3) has an influence on the thermal stability of ligand binding muteins. Replacing the residue naturally present at position 114 of hNGAL can increase the melting temperature of the mutein significantly (cf. Example 14 and FIG. 5). In one embodiment of CTLA-4 binding muteins derived from hNGAL, a charged amino acid is introduced at sequence position 114 of the hNGAL wild type sequence. The charged amino acid can be a positively or a negatively charged amino acid. In presently preferred embodiments, the charged amino acid is a negatively charged amino acid. Typically, this negatively charged amino acid is Asp or Glu. However, it is also possible to introduce an artificial amino acid that provides a negative charge, for example.

In yet other embodiments, CTLA-4 binding hNGAL muteins comprise (in addition or alternatively) to the above-mentioned mutations at any of positions 28, 87, 145 (which are outside the 4 loops that are selected for mutagenesis) an amino acid replacement, compared to the sequence of the hNGAL wild type amino acid, at least one of the sequence position that correspond to sequence positions (55), (65), (88), (114), (116), (118), (120) of the wild type sequence of hNGAL. For example, compared to the sequence of the hNGAL wild type amino acid sequence, a hNGAL mutein of the invention may have at least one of the amino acid substitutions selected from I(55)>V, N(65)>D, Q(88)>R, N(114) >D, N(116)>S, H(118)>Y, M(120)>T or V.

In some embodiments, the CTLA-4 binding hNGAL mutein has an amino acid sequence selected from the group consisting of the sequence of S67.2-F03.UT, S67.3-C21 UT, F92.1-J08 UT, S94.2-F05 UT, S94.7-Q13 UT, S106.3-019 UT, S107.4-C16 UT, S106.3-K20 UT, S106.1-N15 UT, S109.6-J11 UT, S109.4-A15 UT, S109.5-L04 UT, S109.5-L23 UT, S140.1-F09 UT, S140.1-D24 UT, S140.2-P24 UT, S140.2-H04 UT, S140.3-A23 UT, S140.3-P07 UT, S140.4-B16 UT or S140.4-O10 UT (wherein UT denominates the mature amino acid sequence that does not carry an affinity tag such as the T7 tag which can be present in the selected muteins due to the use of such tags in the selection process).

In this conjunction it is noted that the term "amino acid replacement" as used herein means that the amino acid naturally occurring at a given sequence position of, for example, hNGAL (SWISS PROT data bank accession number P80188), A2m (SWISS PROT data bank accession number P30152), 24p3 (SWISS PROT data bank accession number P11672), is substituted by at least one amino acid that is not present at this specific position in the natural (wild type) polypeptide sequence. Such mutations can be introduced easily on the DNA level using established standard methods such as oligodeoxynucleotide-directed mutagenesis (cf., for example, Sambrook, J. et al. (1989) *Molecular Cloning: A Laboratory Manual*, 2nd Ed., Cold Spring Harbor Laboratory Press, Cold Spring Harbor, N.Y.). However, the term "amino acid replacement" also includes the (additional) modification of the length of sequence segments by deletion or insertion of one or more amino acids. Thus, it is within the scope of the invention that, for example, one amino acid at a chosen sequence position is replaced/substituted by a stretch of three amino acids, leading to an insertion of two amino acid residues with respect to the length of (the respective segment) of the wild-type protein. Likewise, it is also possible that a stretch of consecutive amino acids, for example, of three or four amino acids, is replaced by a single amino acid residue.

In this regard it is noted that amino acids other than the 20 naturally occurring amino acids, such as selenocysteine or pyrolysine, can also be incorporated into a mutein of the invention, either in the positions that are mutated in the binding site to ensure binding of the prescribed ligand or at those positions that do not participate in the complex formation. It is also possible to use "artificial" codons in order to introduce other unusual amino acids, for example o-methyl-L-tyrosine or p-aminophenylalanine (Wang, L. et al. (2001) *Science* 292, 498-500; Wang, L. and Schultz, P. G. (2002) *Chem. Comm.* 1, 1-11).

The lipocalin muteins of the invention may comprise the wild-type amino acid sequence at any non-mutated position. The lipocalin muteins disclosed herein may however also contain amino acid mutations apart from the sequence positions as defined in the claims and that participate in the ligand binding. Such mutations are often tolerated or can even prove to be advantageous, for example if they contribute to an improved folding efficiency, protein stability or ligand binding affinity of the mutein (cf. also the possible variations of amino acids in the binding site explained above). As mentioned above, possible alterations of the amino acid sequence include insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan (see also Creighton, T. E. (1993) *Proteins: structures and molecular properties*. pp. 6-20, $2^{nd}$ ed., W.H. Freeman and Company, New York).

One the other hand, it is also possible to introduce non-conservative alterations in the amino acid sequence. For example, hNGAL muteins may have amino acid substitutions, which prevent dimerisation or oligomerization of hNGAL. For instance, Cys87 of hNGAL can be exchanged to Ser or Ala, whereby its covalent crosslinking with other proteins such as gelatinase B (which might occur in in vivo applications of a mutein) can be prevented and the monomeric structure of hNGAL can be stabilized. Similarly, Cys residues which may occur as a result of the mutagenesis and selection of the mutein of the invention are not always crucial for the binding of the given target and may be substituted by Ser or Ala in order to prevent covalent bond formation or oxidation of the thiol group. On the other hand, Cys residues may deliberately introduced, for example, into the β-barrel or at the N- or C-terminus of hNGAL or the other scaffolds used herein in order to provide a reactive group for site specific PEGylation of lipocalin muteins of the invention. In order to provide a reactive group for site specific modification such as PEGylation Cys87 is maintained in some embodiments of CTLA-4 binding hNGAL muteins.

Such modifications of the amino acid sequence can also be carried out (via site-directed mutagenesis of single amino acid positions, for example) in order to simplify sub-cloning of the mutein gene or its parts by incorporating cleavage sites for certain restriction enzymes. For example, the mutation Glu28 to His, and/or Thr145 to Ala can be introduced into the hNGAL gene in order to simplify the cloning of the mutated gene segment via two new BstXI restriction sites at these positions.

Furthermore, mutations can be introduced within or without the four peptide loops in order to improve certain characteristics of the mutein of the protein chosen as scaffold, for example its folding stability or folding efficiency or its resistance to proteases. As also mentioned, mutations can specifically be introduced in order to improve certain characteristics of the mutein. One such further example may be the introduction of lysine residues that allow improved PEGylation of the muteins of the invention. Artificial amino acids providing, for example, a reactive amino acid group in the side chain can also be used for this purpose. Alternatively, if coupling of PEG via existing lysine residues is not desired, other functional groups (e.g. hydroxy groups, amid groups) present in side chains of amino acids of the mutein can be converted into a reactive primary amino group by reaction of this functional group with a bifunctional reagent typically used in protein chemistry that contains one primary amino group. As mentioned above, Cys residues can also deliberately be introduced into a chosen lipocalin scaffold, for example, in order to provide a reactive group that allows for PEGylation or reaction with hydroxyethylstarch of a CTLA-4 binding mutein and so variation of the serum half time of the mutein. In case of hNGAL, it has been found in the present invention that at each of eleven sequence positions Ser 146, Val 84, Thr 141, Asn 116, Ala 145, Glu143, Ser14, Ser 158, Gln 88, Glu60, and Asn 21 a Cys residue can be introduced which then can be used for site specific PEGylation.

Accordingly, the invention is in general also directed to a mutein of hNGAL, A2m or 24p3 in which a Cys residue is introduced at least one of the sequence positions that correspond to sequence positions 14, 21, 60, 84, 88, 116, 141, 145, 143, 146 or 158 of the wild type sequence of hHNGAL (see Example 33). Even though it is sufficient to introduced only one Cys residues for subsequent modification of such a lipocalin mutein, it is also possible, for example, to mutate at least 2, 3, 4, 5, or 9 or all 11 of the residues occurring at these sequence positions in the wild typ to a Cys residue. Exemplary muteins containing artificially introduced Cys residues are the CTLA-4 binding muteins S140.4-O10_S146C, S140.4-O10_V84C, S140.4-O10_T141C, S140.4-O10_N116, S140.4-O10_A145C, S140.4-O10_E143C, S140.4-O10_S14C, S140.4-O10_S158C, S140.4-O10_Q88C, S140.4-O10_E60C, and S140.4-O10_N21C the amino acid sequence of which are given as SEQ ID NO 63, SEQ ID NO 64, SEQ ID NO 65, SEQ ID NO 66, SEQ ID NO 67, SEQ ID NO 68, SEQ ID NO 69, SEQ ID NO 70, SEQ ID NO 71, SEQ ID NO 72, and SEQ ID NO 73.

In line with the above disclosure, the invention also refers to a method of modulating or extending the half-life of hNGAL, A2m or 23p3 or a hNGAL, A2m or 23p3 mutein by coupling an half-life modifying moiety such as polyoxyethyleneglycol or hydroxyethylstarch via the thiol group of a Cys residue that has been introduced into hNGAL, A2m or 23p3 or a mutein thereof at at least one of any of the sequence positions that correspond to sequence positions 14, 21, 60, 84, 88, 116, 141, 145, 143, 146 or 158 of the wild type sequence of hHNGAL. This Cys containing mutein can either have the wild type sequence of hNGAL, A2m or 24p3 at all other sequence positions or can comprise (as the illustrative CTLA-4 binding muteins generated herein) further mutations compared to the wild type sequence.

In accordance with the above, for several applications of proteinaceous compounds such as lipocalin muteins disclosed herein it may be advantageous to use them in the form of fusion proteins or conjugates. For example, a mutein can be conjugated to a compound that includes, but is not limited to, an organic molecule, an enzyme label, a radioactive label, a fluorescent label, a chromogenic label, a luminescent label, a hapten, biotin, an affinity tag, a metal complex, a metal, colloidal gold, an anti-tumor agent or a toxin, too name only examples.

In general, it is possible to label the proteinaceous compound (also referred to herein as mutein) with any appropriate chemical substance or enzyme, which directly or indirectly generates in a chemical, enzymatic or physical reaction a detectable compound or a signal that can be used for detection. An example for a physical reaction is the emission of fluorescence after excitation with radiation or the emission of X-rays by a radioactive label; alkaline phosphatase, horseradish peroxidase or β-galactosidase are examples of enzyme labels which catalyse the formation of chromogenic (colored) compounds which can then be detected. In general all labels which are used for antibodies, except those which exclusively used with the sugar moiety in the Fc part of immunoglobulins can also be used for conjugation to the muteins of the present invention. These conjugates can be prepared by means of methods known to the person skilled in the art.

The mutein can also be conjugated to an organic molecule. As mentioned above, the term "organic molecule" as used in the present application preferably means an organic molecule comprising at least two carbon atoms, but not more than 7 rotatable carbon bonds having a molecular weight between 100 and 2000 Dalton, preferably 1000 Dalton and a molecule including one or two metal atoms.

If conjugates are used, the coupling to the conjugated molecule, which can be a proteinaceous molecule, a carbohydrate, a detectable label or an polymeric organic compound (for example, a polyoxyethyleneglycol chain or hydroxyethylstarch that may be advantageously used in certain pharmaceutical applications) can be realized by any suitable reactive group of the lipocalin mutein, for example, the terminal ε-amino group of lysine residues or purposely introduced Cys residues as disclosed above. Such conjugation partner can for example extend the serum half-life of the mutein, when used in vivo. In addition to polyalkylene glycol molecules, the conjugation partner can, for example, also be the Fc part of an immunoglobulin, or a part thereof, e.g. a CH3 domain or a CH4 domain, or a protein having affinity to serum albumin. Such a protein with affinity to serum albumin may, for example, be a bacterial serum albumin binding domain or a respective artificial antibody fragment or a lipocalin mutein. The latter two can readily be generated by evolutionary methods in order to specifically bind serum albumin (see also below). Other conjugation partners that are suitable for extending the serum half life of muteins of the invention are albumin binding peptides. Numerous examples of such albumin binding peptides exist, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395.

The conjugation of a toxin to a CTLA-4 binding proteinaceous compound of the invention such as a lipocalin mutein is particularly useful if the mutein is employed in therapeutic applications such as the treatment or prevention of an (auto)-immune disease in a mammal (see below) or any therapeutic use wherein a depletion of activated T cells, a depletion of tumor cells over-expressing CTLA-4 or a depletion of regulatory T cells is desired. Examples of suitable toxins include, but are not limited to toxins such as pertussis-toxin, diphtheria toxin, ricin, saporin, pseudomonas exotoxin, calicheamicin or a derivative thereof, a taxoid, a dolastatin analogue (e.g. auristatin E of auristatin E, monomethylauristatin E, auristatin PYE or auristatin PHE), a maytansinoid or a tubulysin, to name only a few.

Likewise, a conjugate of a CTLA-4 binding proteinaceous compound such as a lipocalin mutein with an anti-tumor agent can be advantageously used for the treatment of cancer. Examples of suitable anti-tumor agents include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Dacarbazine, Leucovorin, incristine, Vindesine, Vinorelbine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, or methoxyestradiol derivatives.

It is also possible to use a mutein of the invention together with a fusion partner. For this purpose, the mutein can be fused at its N-terminus and/or its C-terminus to a protein, a protein domain or a peptide. For example a peptide such as a signal sequence and/or an affinity tag and/or a protein is operably fused to the amino terminus or to the carboxy terminus of the mutein.

The fusion partner can be suitable to confer new characteristics on the mutein, for example enzymatic activity or affinity for other molecules such as proteins, macromolecules or low molecular weight targets. For example, fusions with enzymes which catalyse chromogenic or fluorogenic reactions (e.g. alkaline phosphatase, horseradish peroxidase, glutathione-S-transferase) or which can serve for the liberation of cytotoxic agents are possible. Further examples of fusion partners which can be advantageous in practice are binding domains such as the albumin-binding domain of protein G, protein A, peptides binding to serum albumin (e.g., the peptides described in US patent application 2003/0069395), antibody fragments (e.g., CH3, CH4 domains), oligomerizing domains, toxins or also muteins of the invention or other lipocalin muteins.

In case a lipocalin is used for the generation of the CTLA-4 binding protein, the latter case results in the formation of "duocalins", which are described for example in PCT application WO 99/16873 or Schlehuber, S. & Skerra, A. (2001) *Biol. Chem.* 382, 1335-1342). One example of such a dimeric lipocalin mutein is a CTLA-binding hNGAL mutein as described herein that is fused to a lipocalin mutein, for example a mutein of the bilin-binding protein (BBP) of *Pieris brassicae*, a mutein of the human apolipoprotein D (ApoD), a mutein of human tear lipocalin or a second hNGAL mutein. The (second) lipocalin mutein can have affinity for a small molecule anti-cancer drug (e.g. a cytostaticum) such as cisplatin, taxol, 5-Fluorouracil or doxorubicin. Such a dimeric lipocalin mutein may be used for the treatment or prevention of T cell mediated disease or tumor types expressing CTLA-4 in a mammal as explained in detail below. In another approach, the lipocalin mutein that is used as fusion or conjugation partner may bind to serum albumin, in particular human serum albumin and thus is able to extend the serum half life of a CTLA-4 binding mutein of the invention, for example. In yet another example, such a dimer is formed by two different CTLA-4 binding muteins or by two molecules of the same CTLA-4 binding molecules. Such a fusion protein comprising two CTLA-4 binding molecules (either as a homodimer in case of two molecules of the same mutein, or a heterodimer, in case two different CTLA-4 muteins are employed) can be used as agonistic polyvalent pharmaceutical reagent that inhibits, reduces or prevent activation, expansion or effector activities of CTLA-4 expressing T cell, as explained below. If a a fusion protein that comprises two or more CTLA-4 binding lipocalin muteins is used as agonistic pharmaceutical reagent, it may be useful to use a polypeptide linker that allows or facilitates to bring the two lipocalin muteins into a geometric (spatial) arrangement that is suitable for achieving the agonistic effect. The choice of the particular sequence of this linker is within the knowledge of the person of average skill in the art. Examples of possible linkers include linkers that contain Gly and Ser as amino acids. One such example are linker amino acid sequences which exclusively or mainly, for example >60%, contain Gly and Ser such as $(Gly-Gly-Gly-Ser)_n$ (SEQ ID NO: 81) with n=1 to 5.

Any lipocalin can be used as scaffold for the generation of a lipocalin mutein with prescribed affinity which is then used as fusion or conjugation partner of the CTLA-4 binding mutein in such dimeric fusion protein of the present invention. Examples of suitable scaffolds of the lipocalin family include, but are not limited to, the bilin binding protein of *Pieris brassicae* (BBP), the retinol binding protein (RBP), the human apolipoprotein D, the human tear lipocalin (TlpC) or also hNGAL, A24m or 24p3. The generation of lipocalin muteins that are based on the above-mentioned lipocalin scaffolds and that have affinity towards a given (prescribed) target are described in detail in the international patent applications WO 99/16873, WO 00/75308, WO 03/029471, WO 03/029462, WO 03/029463, WO 2005/019254, WO 2005/019255 or WO 2005/019256, for instance.

Affinity tags such as the Strep-Tag® or the Strep-Tag® II (Schmidt et al., J. Mol. Biol. 255 (1996), 753-766), the myc tag, the flag tag, the T7 tag, or oligohistidine tags (e.g., His6-tags (SEQ ID NO: 82)) or proteins such as glutathione-S-transferase which can be used for purification by affinity chromatography and/or for detection (e.g. using the specific affinity of the Strep-Tag® for streptavidin) are further examples of suitable fusion partners. Proteins with chromogenic or fluorescent properties such as the green fluorescent protein (GFP) are suitable fusion partners, too. Such optically active fusion partners (as well as signal generating compounds that are conjugated to the lipocalin) are very suitable for in vivo imaging or other diagnostic purposes in vivo or in vitro purposes.

The term fusion protein as used herein also includes muteins of the invention, for example lipocalin muteins that are equipped with a signal sequence. Signal sequences at the N-terminus of a polypeptide according to the invention can be suitable to direct the polypeptide to a specific cell compartment during the biosynthesis, for example into the periplasm of *E. coli* or to the lumen of the eukaryotic cell or into the medium surrounding the cell. In so doing, the signal sequence is cleaved by a signal peptidase. It is also possible to use other targeting or signaling sequences which are necessarily located at the N-terminus of the polypeptide and which allow the localization thereof in specific cell compartments. An exemplary signal sequence for secretion into the periplasm of *E. coli* is the OmpA-signal sequence. A large number of further signal sequences is known in the art.

The present invention also relates to nucleic acid molecules (DNA and RNA) comprising nucleotide sequences coding for a CTLA-4 binding lipocalin muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding functional CTLA-4 binding lipocalin muteins as described herein.

In one embodiment of the invention, the nucleic acid sequences encode lipocalin muteins which block the interaction between CTLA-4 and at least one of its physiological ligands CD80 (B7-1) or CD86 (B7-2). In other embodiments, nucleic acid molecules encode muteins that bind human CTLA-4 with a $K_D$ of 25 nM or less. Also comprised are nucleic acids that encode muteins that bind murine CTLA-4 with a $K_D$ of 200 nM or less, with a $K_D$ of 100 nM or less. In presently preferred embodiments the nucleic acid molecule comprises a nucleotide sequence encoding the mutein of SEQ ID NO: 37, or SEQ ID NO: 54, for example.

The invention is also directed to a nucleic acid molecule comprising a sequence encoding a mutein according to the invention or a fusion protein thereof. The invention further includes nucleic acid molecules encoding lipocalin muteins that comprise additional nucleotide mutations at sequence positions other than those mentioned above. Such mutations are often tolerated or can even prove to be advantageous, for example, if they contribute to an improved folding efficiency, protein stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing genetic information, giving rise to transcription and/or translation of an encoded protein, a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactorily functional in a particular host cell, they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecule of the invention can also be comprised in a vector or any other cloning vehicles, such as plasmids, phagemids, phages, baculoviruses, cosmids or artificial chromosomes. Apart from the regulatory sequences described above and the nucleic acid sequence encoding a lipocalin mutein of the invention, such cloning vehicles can include replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a CTLA-4 binding lipocalin mutein of the invention, and in particular a cloning vector containing the coding sequence of such a mutein, can be transfected into a host cell capable of expressing the gene. Transformation can be performed using standard techniques (Sambrook, J. et al. (1989), supra). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *E. coli* or *Bacillus subtilis*, or eukaryotic, such as *Saccharomyces cerevisiae, Pichia pastoris*, SF9 or High5 insect cells, immortalized mammalian cell lines (e.g. HeLa cells or CHO cells) or primary mammalian cells.

The invention also relates to a method for the production of a CTLA-4 binding lipocalin mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eukaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is transformed with a cloning vector comprising a nucleic acid molecule encoding such a mutein using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium. Since many lipocalins comprise intramolecular disulfide bonds, it can be preferred to direct the nascent polypeptide to a cell compartment having an oxidizing redox milieu using an appropriate signal sequence. Such an oxidizing environment is provided by the periplasm of Gram-negative bacteria such as *E. coli* or in the lumen of the endoplasmatic reticulum of eukaryotic cells and usually favors the correct formation of the disulfide bonds. It is, however, also possible to generate a mutein of the invention in the cytosol of a host cell, preferably *E. coli*. In this case, the polypeptide can, for instance, be produced in form of inclusion bodies, followed by renaturation in vitro or as soluble material. A further option is the use of specific host strains having an oxidizing intracellular milieu, which thus allow the production of the native protein in the cytosol.

However, a mutein of the invention may not necessarily be generated or produced only by use of genetic engineering. Rather, a lipocalin mutein can also be obtained by chemical synthesis such as Merrifield solid phase polypeptide synthesis. It is for example possible that first promising mutations are identified using molecular modeling and then to synthesize the wanted (designed) polypeptide in vitro and investigate the binding activity for CTLA-4. If wanted, chemical synthesis of a lipocalin mutein can also be used for large scale production of the mutein, for example, for therapeutic applications. Methods for the solid phase and/or solution phase synthesis of proteins are well known in the art (reviewed, e.g., in Lloyd-Williams, P. et al. (1997) Chemical Approaches to the Synthesis of Peptides and Proteins. CRC Press, Boca Raton, Fields, G. B., and Colowick, S. P. (1997) Solid-Phase Peptide Synthesis, Academic Press, San Diego, or Bruckdorfer, T. et al. (2004) Curr. Pharm. Biotechnol. 5, 29-43).

The invention also relates to a pharmaceutical composition comprising at least one inventive compound, for example, a CTLA-4 binding lipocalin mutein, or a fusion protein or a conjugate thereof and a pharmaceutically acceptable excipient.

The compounds according to the invention can be administered via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. A combination of intravenous and subcutaneous infusion and/or injection might be most convenient in case of compounds with a relative short serum half life. In this regard, transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of biopharmaceuticals such as the CTLA-4 binding hNGAL, A2m or 24p3 muteins described here. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In a presently preferred embodiment of the invention the pharmaceutical composition is administered parenterally, with intravenous infusion or injection being one of the most preferable application methods.

The dosage of the compound such as a small molecule or a mutein applied may vary within wide limits to achieve the desired therapeutic response for a particular patient. It will, for instance, depend on the affinity of the compound for CTLA-4 as well as the half-life of the respective complex in vivo, its biodistribution, the mode of administration, the severity of the disease/disorder being treated as well as the medical condition of the patient. For example, treatment of short-term conditions or disorders such as an inflammation or short term applications such as vaccination might be best accomplished when using a dose as high as maintainable. In this respect, the smaller size of a lipocalin mutein or other small proteins of the invention such as microbodies compared to intact antibodies or antibody fragments such as Fab fragments can be of advantage since the smaller size should lead to a better penetration of the affected area or place of action. This in turn means that the lipocalin mutein or another CTLA-4 binding protein of the invention can be applied in higher dosages and at the same time be more effective than antibody fragments.

However, if wanted, a CTLA-4-binding mutein may also be given in a sustained release formulation for example liposomal dispersions or hydrogel-based polymer microspheres like PolyActive or OctoDEX. Alternatively, the half-life of a lipocalin mutein can be extended for example, by fusion to the Fc region of an preferably human immunoglobulin, the CH4 domain of human IgE, or by conjugation to a polymer such as polyalkylene glycol (substituted or unsubstituted) or an activated derivative thereof, for example, polyethylene glycol (PEG) as described in WO 99/64016, U.S. Pat. No. 6,177, 074, U.S. Pat. No. 6,403,564 in relation to interferon, or as known for other proteins such as PEG-modified asparaginase, PEG-adenosine deaminase (PEG-ADA) or PEG-superoxide dismutase, for example (see for example, Fuertges et al. (1990) *J. Control. Release* 11, 139-148). The molecular weight of such a polymer, which can be preferably polyethylene glycol, may for example, range from about 300 to about 70,000 Dalton, including, for example, polyethylene glycol with a molecular weight of about 10,000, about 20,000, about 30,000 or about 40,000 Dalton (cf., Examples 20 and 33). As described in U.S. Pat. No. 6,500,930 or 6,620,413, for example, carbohydrate oligo- and polymers such as starch or hydroxyethyl starch (HES) can also be conjugated to a mutein of the invention for this purpose. Further suitable fusion partners for extending the half-life of a CTLA-4 binding lipocalin mutein of the invention include albumin (Osborn, B. L. et al. (2002) *J. Pharmacol. Exp. Ther.* 303, 540-548), or a albumin binding protein, for example, a bacterial albumin binding domain, such as the one of streptococcal protein G (König, T. and Skerra, A. (1998) *J. Immunol. Methods* 218, 73-83). Another possibility of a sustained or a controlled release formulation is the use of osmotic pumps such as Alzet pumps (see Example 15).

Once a suitable administration form has been found, the establishment of a therapeutically effective dosage amount of a CTLA-4 binding compound or mutein of the invention for a given individual is within the level of skill in the art.

In general, a dose of about 0.05 mg to 50 mg compound or mutein per kilogram body weight administered in an appropriate schedule may be appropriate. Presently preferred dosage levels range from 0.5 mg to 5 mg per kg body weight for a long-term regimen and from 5 mg to 25 mg per kg body weight for short-term treatments. In case of muteins such as CTLA-4 binding muteins of hNGAL or A2m as described here, the amount of 0.05 to 50 mg per kilogram relates to the unmodified lipocalin muteins. In case, the mutein is modified, for example by a PEG molecule or an albumin binding peptide, the dosage is adjusted (increased) accordingly to still administer the same amount of CTLA-4 binding mutein. The inventive compound/mutein can be applied as a single dose or may be divided into several, e.g. two to four, separate administrations. Alternatively, a CTLA-4 binding compound or mutein as described here can also be continuously infused over a certain period of time.

Accordingly, the muteins of the present invention can be formulated into compositions using pharmaceutically acceptable ingredients as well as established methods of preparation (Gennaro, A. L. and Gennaro, A. R. (2000) *Remington: The Science and Practice of Pharmacy*, 20th Ed., Lippincott Williams & Wilkins, Philadelphia, Pa.). To prepare the pharmaceutical compositions, pharmaceutically inert inorganic and/or organic excipients can be used. To prepare e.g. pills, powders, gelatin capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. For achieving a depot effect compounds/polypeptides of the invention such as hNGAL, A2m or 24p3 muteins may be incorporated into slow or sustained release or targeted delivery systems, such as liposomes and microcapsules.

The formulations can be sterilized by numerous means, including filtration through a bacteria-retaining filter, or by incorporating antiseptic agents in the form of sterile solid compositions which can be dissolved or dispersed in sterile water or other sterile medium just prior to use.

As is evident from the above disclosure, a CTLA-4 binding compound such as a mutein of the present invention or a fusion protein or conjugate thereof can also be employed in any diagnostic application in which the presence of human CTLA-4 is to be detected or in which the amount of human CTLA-4 in a sample is measured. The formation of a complex between CTLA-4 and the mutein is detected using one of the labels or fusion partner described earlier. Accordingly, a kit of the invention comprises a CTLA-4 binding compound/mutein described herein. Such a kit may optionally also comprise instructions for use as well as other reagents that can be used for the measuring the complex formation between the compound/mutein and CTLA-4.

In one embodiment, a CTLA-4 binding lipocalin mutein can be used for in vitro detection of tumor cells in a tissue sample that is obtained from a person that is suspected to have developed a tumor. For this purpose, the CTLA-binding lipocalin mutein can be conjugated or fused to any label that is commonly used in diagnostic applications, for example, a chromogenic or fluorescent label, gold particles or a streptavidin binding moiety such as biotin or a Strep-Tag® affinity peptide.

In another embodiment a CTLA-4 binding mutein of the invention is used for in vivo tumor imaging or tumor targeting. Radionuclides such as $^{18}$F, $^{64}$Cu, $^{86}$Y, $^{99}$Tc, $^{111}$In or $^{125}$I can be employed as respective label. The labeling of such a radionuclide can be carried out in accordance with established protocols well known to the person skilled in the art. If, for example, a hNGAL mutein of the invention is to be labeled with $^{125}$I for in vivo tumor imaging, labeling can occur using $^{125}$I-N-succinimidyl 3-iodobenzoate. Labeling with $^{99}$Tc can, for example, be carried out by means of Tc carbonyl complexes as described in Waibel et al, "Stable one-step technetium-99m labeling of His-tagged recombinant proteins with a novel Tc(I)-carbonyl complex", (1999) Nature Biotech. 17 (9): 897-901) and labeling with $^{18}$F or $^{64}$Cu can be carried as described by Chen et al., 2004 January-February, 15(1):41-49. MicroPET and autoradiographic imaging of breast cancer alpha v-integrin expression using 18F- and 64Cu-labeled RGD peptide. Conjugates with $^{111}$In or $^{86}$Y can for example, be obtained by diethylenetriaminepentaacetic acid chelation as described in Lövquist et al., PET Imaging of $^{86}$Y-Labeled Anti-Lewis Y Monoclonal Antibodies in a Nude Mouse Model: Comparison Between $^{86}$Y and $^{111}$In Radiolables (2001), Journal of Nuclear Medicine Vol. 42 No. 8 1281-1287. Such conjugates of CTLA-4 binding lipocalin muteins can also be used in bioavailibity distribution studies, clinical pharmacokinetic and pharmacodynamic evaluations, including target modulation as well as therapeutic agent in tumor treatment or radioimmunotherapy.

In principle, a CTLA-4 binding compound/mutein can be used in any therapeutic application in which binding of CTLA-4 to a physiological ligand, for example, B7-1 or B7-2 is involved. Examples of such therapeutic applications include, but are not limited to, the prevention and/or treatment of cancer or the prevention and/treatment of an infectious disease. In such application, an anti-CTLA-4 lipocalin mutein is administered to a mammal, for example, a human, a dog, an ape, a rat, a mouse, in an amount of that is effective in treating said cancer or that infectious disease.

The infectious diseases may be caused by exposure to a particular toxin or pathogen. Similar to its application to tumors as discussed below, CTLA-4 blockade that is mediated by a CTLA-4 binding lipocalin mutein, and surrogate therapeutic endpoint can be used alone, or as an adjuvant, in combination with vaccines, to stimulate the secondary or memory immune response to pathogens, toxins, and selfantigens. CTLA-4 blockade has been shown to be effective in the acute phase of infections of *Nippostrongylus brasiliensis* (McCoy, K. et al. (1997) 186 (2); 183-187) and *Leishmania donovani* (Murphy, M. et al. (1998) J. Immunol. 161: 4153-4160).

Examples of pathogens for which this therapeutic approach may be particularly useful include pathogens for which there is currently no effective vaccine, or pathogens for which conventional vaccines are of limited effectiveness. These include, but are not limited to HIV, Hepatitis (A, B, & C), Influenza, Herpes, Giardia, Malaria, Leishmania, *Staphylococcus aureus*, and *Pseudomonas aeruginosa*. CTLA-4 blockade is particularly useful in boosting immunity against established infections by agents such as HIV that present altered antigens over the course of the infections.

These epitopes are recognized as foreign at the time of administration of the CTLA-4 binding compound/mutein of the invention, thus provoking a strong T cell response that is not dampened by negative signals through CTLA-4.

Some examples of pathogenic viruses causing infections treatable by using CTLA-4 binding lipcalin muteins of the invention include hepatitis (A, B, or C), herpes virus (e.g., VZV, HSV-1, HAV-6, HSV-11, and CMV, Epstein Barr virus), adenovirus, influenza virus, flaviviruses, echovirus, rhinovirus, coxsackie virus, cornovirus, respiratorysyncytial virus, mumps virus, rotavirus, measles virus, rubella virus, parvovirus, vaccina virus, HTLV virus, dengue virus, papillomavirus, molluscum virus, poliovirus, rabies virus, JC virus and arboviral encephalitis virus, to name only a few.

Some examples of pathogenic bacteria causing infections treatable by CTLA-4 binding lipocalin muteins include chlamydia, rickettsial bacteria, mycobacteria, staphylococci, streptococci, pneumonococci, meningococci andconococci, *klebsiella, proteus, serratia,* pseudomonas, *legionella*, diphtheria, *salmonella*, bacilli, cholera, tetanus, botulism, anthrax, plague, leptospirosis, and Lyme disease bacteria.

Some examples of pathogenic fungi causing infections treatable by CTLA-4 binding lipocalin muteins include *Candida* (*albicans, krusei, glabrata, tropicalis*, etc.) *Cryptococcus neoformans, Aspergillus* (*fumigatus, nige*, etc.), *Gefaus Mucorales* (*Mucor, Absidia, Rhizophus*), *Sporothrix schenkii, Blastomyces dermatitidis, Paracoccidioides brasiliensis, Coccidioidesimmitis* and *Histoplasma capsulatum*.

Some examples of pathogenic parasites causing infections treatable by CTLA-4 binding muteins include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

Examples of cancers that can be treated using a CTLA-binding compound as described here include, but are not limited to, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, t-cell lymphoma, cutanous T cell lymphoma (CTCL), and combinations of said cancers.

When applied for the treatment of cancer, the CTLA-4 binding compound or mutein can be administered to a mammal in combination with another pharmaceutically active agent. Examples of such agents include, but are not limited to, a chemotherapeutic or anti-tumor agent, a cancer vaccine, an immunomodulatory agent, an anti-angiogenesis agent, an anti-vascular agent, a signal transduction inhibitor, an anti-proliferative agent, an apoptosis inducer, a chemokine, a cytokine and an inhibitor of a survival pathway.

In one presently preferred embodiment, the mutein is administered in combination with an anti-angiogenesis agent. Examples of suitable anti-angiogenesis are a MMP-2 (matrix-metalloproteinase 2) inhibitor, an MMP-9 (matrix-metalloproteinase 9) inhibitor, and a COX-II (cyclooxygenase II) inhibitor, to name only a few.

In another presently preferred embodiment, the CTLA-4 binding mutein is administered in combination with a chemotherapeutic agent. The chemotherapeutic agent may be a mitotic inhibitor, alkylating agent, anti-metabolite, intercalating antibiotic, growth factor inhibitor, cell cycle inhibitor, enzyme, topoisomerase inhibitor, biological response modifier, anti-hormone, angiogenesis inhibitor, or an anti-androgen.

In yet another presently preferred embodiment, the CTLA-4 binding mutein is administered in combination with a signal transduction inhibitor. Examples of suitable signal transduction inhibitors include, but are not limited to, an EGFR (epidermal growth factor receptor) inhibitor, VEGF (vascular endothelial growth factor) inhibitor, and an erbB2 receptor inhibitor.

In yet another presently preferred embodiment, the CTLA-4 binding mutein is administered in combination with a cytokine. Illustrative examples of suitable cytokines for use in the present invention include Interleukin-2 (IL-2), Interferon-gamma (IFN-g), granulocyte/macrophage colony-stimulating factor (GM-CSF), Interferon-12 (IL-12), Interferon-18 (IL-18), and SL cytokine precursor (FLT-3L).

It is also encompassed in the present invention to administer to a mammal an amount of a CTLA-4 binding lipocalin mutein in combination with radiation therapy. The amount of the mutein in combination with the radiation therapy is effective in inhibiting abnormal cell growth or treating the hyperproliferative disorder in the mammal.

In another therapeutic application, a CTLA-4 binding mutein is employed for the treatment or prevention of T cell mediated disease or tumor types expressing CTLA-4 in a mammal. For this purpose, a fusion or conjugate of an anti-CTLA-4 mutein as described herein with a toxin can be used. The amount of said fusion or conjugate is chosen such that it is effective in treating said T cell mediated disease or tumor.

Examples of T cell mediated diseases that can be treated in this manner include graft versus host disease, transplant rejection or auto-immune diseases such as multiple sclerosis, lupus erythematosus, myasthenia gravis, rheumatoid arthritis or diabetes mellitus. For the same purpose, polyvalent formulations of CTLA-4 binding muteins that cross-link cell surface CTLA-4 and act as a CTLA-4 agonist might be used instead of a conjugate or fusion of a anti-CTLA-4 lipocalin mutein with a toxin (see, e.g., Krummel and Allison, 1996, J. Exp. Med. 183, 2533-2540, cf. also International patent application WO 01/14424). A polyvalent formulation of CTLA-4 binding muteins that acts as an agonist can be prepared by covalently crosslinking two or more of the muteins using respective cross-linking reagents. Alternatively, CTLA-4 binding muteins can be cross-linked to each other by non-covalent interactions. For this purpose, they can for example, be conjugated to or fused to an oligomerization module such as a leucine zipper, a jun/fos oligomerisation modul or an immunoglobulin domain (like CH4 as shown). Non-covalent oligomerization and thus formation of a preparation of polyvalent CTLA-4 muteins then occurs via this oligomerization modul. In accordance with this approach, a polyvalent CTLA-4 cross-linking lipocalin mutein will transduce a negative signal similar to the signal elicited by the natural ligand and inhibit, reduce or prevent activation, expansion or effector activities of the CTLA-4 expressing T cell. Accordingly, a pharmaceutical composition wherein the at least two CTLA-4 binding muteins are (cross)-linked to each other to form a multimer, for example, a dimer, trimer or higher oligomer is also encompassed in the present invention. As mentioned above, a dimeric fusion protein in which two CTLA-4 binding molecules (which can be formed either by two different CTLA-4 binding muteins or two molecules of the same CTLA-4 binding mutein) are fused to each other can be used in such a pharmaceutical composition.

In accordance with the above, a CTLA-binding compound/mutein can be used as monotherapy or as combination therapy. Examples of combination therapy comprise a tumor vaccination approach and/or chemotherapy or therapy with a cytostatic or radiation therapy or therapy with radionuclides. Combination therapy as used herein also comprises surgical resection for the prevention or the treatment of cancer.

When used as a combination therapy for the treatment of infectious diseases, the combination therapy may comprise a vaccination approach for the prevention or the treatment of infectious diseases.

In a further embodiment, a CTLA-4 binding lipcocalin compound/mutein when fused or conjugated to a toxin, the mutein is administered to lead to a depletion of activated T cells or to a depletion of tumor cells over-expressing CTLA-4 or to a depletion of regulatory T cells. In yet another embodiment, a fusion or conjugate of a CTLA-4 binding compound with a toxin is used for the prevention and/or treatment of T cell mediated diseases, non Hodgkins peripheral T-cell lymphoma, cutanous T cell lymphoma (CTCL), or cancer.

The generation of CTLA-4 binding muteins of the present invention can be carried out using any suitable technique that is known in the art for generating lipocalin muteins with antibody-like properties, i.e. that have affinity towards a given target. Examples of such evolutionary methods are described in detail in the international patent applications WO 99/16873, WO 00/75308, WO 03/029471, WO 03/029462, WO 03/029463, WO 2005/019254, WO 2005/019255 or WO 2005/019256, for instance.

In all these case, the coding sequence for the each of the proteins used as scaffold here can serve as a starting point for mutagenesis of the peptide segments selected in the present invention. The coding sequence of hNGAL has first been described by Bundgard et al., Biochem. Biophys. Res. Commun. 202 (1994), 1468-1475. The coding sequence of A2m and 24p3, respectively has been published by Chan et al., Nucleic Acid Res. 16 (1988) 11638; and Stoesz et al., Oncogene 11 (1995), 2233-2241, for example.

For the mutagenesis of the amino acids in one or more of the four selected peptide loops, the various known methods for site-directed mutagenesis or for mutagenesis by means of the polymerase chain reaction as described in the above PCT applications are available to the person skilled in the art. The mutagenesis method can, for example, be characterized in that mixtures of synthetic oligodeoxynucleotides, which bear a degenerate base composition at the desired positions, can be used for introduction of the mutations. The use of nucleotide building blocks with reduced base pair specificity, as for example inosine, is also an option for the introduction of mutations into the chosen sequence segment or amino acid positions. The procedure for mutagenesis of target-binding sites is simplified as compared to antibodies (as the classical scaffold used in evolutionary methods for creating molecules with a desired binding specificity), since hNGAL, A2m and 24p3 only four instead of six sequence segments—corresponding to the four above cited peptide loops—have to be manipulated for this purpose. A further possibility is the so-called triplet-mutagenesis. This method uses mixtures of different nucleotide triplets each of which codes for one amino acid for the incorporation into the coding sequence.

One of the various applicable methods for the introduction of mutations in the region of the four selected peptide loops of the scaffold proteins used here (i.e. in the case of hNGAL at sequence positions 33 to 54, 66 to 83, 94 to 106 and 123 to 136) is based on the use of four oligodeoxynucleotides, each of which is partially derived from one of the four corresponding sequence segments to be mutated. In the production of these oligodeoxynucleotides, the person skilled in the art can employ mixtures of nucleic acid building blocks for the synthesis of those nucleotide triplets which correspond to the amino acid positions to be mutated, so that codons or anticodons randomly arise for all amino acids or, according to the genetic code and to the composition of this mixture, for a selection of the desired amino acids at this position.

For example, the first oligodeoxynucleotide corresponds in its sequence—apart from the mutated positions—at least partially to the coding strand for the peptide loop, which is located in the polypeptide sequence of hNGAL at the most N-terminal position. Accordingly, the second oligodeoxynucleotide corresponds at least partially to the non-coding strand for the second sequence segment following in the polypeptide sequence. The third oligodeoxynucleotide corresponds in turn at least partially to the coding strand for the corresponding third sequence segment. Finally, the fourth oligodeoxynucleotide corresponds at least partially to the non-coding strand for the fourth sequence segment. A polymerase chain reaction can be performed with the respective first and second oligodeoxynucleotide and separately if needed, with the respective third and fourth oligodeoxynucleotide by using the nucleic acid that encodes the scaffold protein and/or its complementary strand as a template.

The amplification products of both of these reactions can be combined by various known methods into a nucleic acid which comprises the sequence from the first to the fourth sequence segments and which bears the mutations at the selected amino acid positions. To this end, both of the products can for example be subjected to a new polymerase chain reaction using flanking oligodeoxynucleotides as primers as well as one or more mediator nucleic acid molecules which contribute the sequence between the second and the third sequence segment. In the choice of the number of the oligodeoxynucleotides used for the mutagenesis and their arrangement within the gene sequence of protein used, the person skilled in the art has furthermore numerous alternatives at his disposal.

The nucleic acid molecules which code for the sequence region encompassing the four peptide loops of the protein used and which contain mutations at the selected positions defined above can be connected by ligation with the missing 5'- and 3'-sequences of a nucleic acid coding for hNGAL, for example, and/or the vector, and can be cloned in a known host organism. A multitude of procedures are at one's disposal for the ligation and the cloning. For example, in the course of an amplification, synthetic nucleic acid molecules with restriction endonuclease recognition sequences, which are also present at the corresponding positions in the nucleic acid sequence for hNGAL, can be attached at both ends of the nucleic acid to be cloned so that a ligation is made possible following hydrolysis with the corresponding restriction enzyme. The missing 5'- and 3'-sequences of a nucleic acid coding for the respective lipocalin used in the present invention can also be attached to the nucleic acid molecule comprising the mutated sequence positions via PCR.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains (Low et al., J. Mol. Biol. 260 (1996), 359-368). Such methods can also be used for the further optimization of the target affinity or target specificity of a mutein which has already been produced. Mutations which possibly occur outside the segments of the sequence positions 33 to 54, 66 to 83, 94 to 106 and 123 to 136 of hNGAL, for instance, can often be tolerated or can even prove advantageous, for example if they contribute to an improved folding efficiency or folding stability of the mutein.

After having brought the coding nucleic acid sequences that were subjected to mutagenesis to expression, the clones carrying the genetic information for the plurality of respective muteins which bind CTLA-4 can be selected from the library obtained. Known expression strategies and selection strategies can be employed for the selection of these clones. Methods of this kind have also been described in the context of the production or the engineering of recombinant antibody fragments, such as the "phage display" technique (Hoess, Curr. Opin. Struct. Biol. 3 (1993), 572-579; Wells and Lowman, Curr. Opin. Struct. Biol. 2 (1992), 597-604) or "colony screening" methods (Skerra et al., Anal. Biochem. 196 (1991), 151-155) or "ribosome display" (Roberts, Curr. Opin. Chem. Biol. 3 (1999) 268-273).

An embodiment of the "phage display" technique (Hoess, supra; Wells and Lowman, supra; Kay et al., Phage Display of Peptides and Proteins—A Laboratory Manual (1996), Academic Press) is given here as an example of a selection method according to the invention for muteins with the desired binding characteristics. The various other possible embodiments of the "phage display" technique are hereby incorporated into the disclosure by reference. For the exemplary selection method, phasmids are produced which effect the expression of the mutated hNGAL structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid.

The fusion protein can contain other components such as for example an affinity tag or an epitope sequence for an antibody which allows the immobilization or the later purification of the fusion protein or its parts. Furthermore, a stop codon can be located between the region coding for hNGAL or its mutein and the gene segment for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as for example M13 or f1 (Beck and Zink, Gene 16 (1981), 35-58) or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the hNGAL mutein encoded by the respective phasmid built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient generally a bacterial strain carrying an F- or F'-plasmid. In this way a physical coupling is ensured between the packaged nucleic acid carrying the genetic information for the respective hNGAL mutein, and the encoded protein which is at least partially presented in functional form on the surface of the phagemid.

The vector phNGAL35 (FIG. 1) can for example be used in the construction of the phasmid with the sequences coding for the hNGAL muteins. The nucleic acid coding for the peptide loops can, for example, be inserted into the vector phNGAL35 via both of the BstXI-restriction sites. Recombinant phasmids are incorporated by transformation into the *E. coli* strain, for example XL1-blue (Bullock et al., BioTechniques 5 (1987), 376-379) or TG1. In this way, clones are made which can produce many different hNGAL muteins as fusion proteins.

This library, i.e. the collection of the clones obtained, is subsequently superinfected in liquid culture according to known methods with an M13-helper phage. After this infection the incubation temperature of the culture can be reduced for production of the phagemids. Preferred incubation temperatures are those in which the optimal folding of the hNGAL mutein as a component of the fusion protein with the phage coat protein or its fragment is expected. During or after the infection phase the expression of the gene for the fusion protein with the hNGAL mutein can be induced in the bacterial cells, for example by addition of anhydrotetracycline. The induction conditions are chosen such that a substantial fraction of the phagemids produced presents at least one hNGAL mutein. The phagemids are isolated after a culture incubation phase of for example 6 to 8 hours. Various methods are known for isolation of the phagemids, such as for example precipitation with polyethylene glycol.

The isolated phasmids can be subjected to a selection by incubation with the desired target, wherein the target is present in a form allowing at least a temporary immobilization of those phagemids carrying muteins with the desired binding activity as fusion proteins in their coat. Among the various embodiments known to the person skilled in the art, the target can for example be conjugated with a carrier protein such as serum albumin and be bound via this carrier protein to a protein binding surface, for example polystyrene. Microtiter plates suitable for ELISA techniques or so-called "immuno-sticks" can preferably be used for this immobilization of the target. Alternatively, conjugates of the target can also be implemented with other binding groups such as for example biotin. The target can then be immobilized on surfaces which selectively bind this group, such as for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Residual protein—or phagemid-binding sites present on the surfaces which are charged with targets can be saturated with blocking solutions known for ELISA-methods. The phagemids are for example subsequently brought in contact in a physiological buffer with the target immobilized on the surface. Unbound phagemids are removed by multiple washings. The phagemid particles remaining on the surface are subsequently eluted. For elution, the free target can be added as a solution, or target-specific phagemides can be eluted with immunoglobulins or natural ligand proteins which specifically bind to the target of interest. But the phagemids can also be eluted by addition of proteases or, for example, in the presence of acids, bases, detergents or chaotropic salts, or under moderately denaturing conditions. A preferred method is the elution using buffers of pH 2.2, wherein the eluate is subsequently neutralized.

Afterwards, E. coli cells are infected with the eluted phagemids using generally known methods. The nucleic acids can also be extracted from the eluted phagemids and be incorporated into the cells in another manner. Starting from the E. coli clones obtained in this way, phagemids are in turn generated by superinfection with M13-helper phages according to the method described above and the phagemids propagated in this way are once again subjected to a selection on the surface with the immobilized target. Multiple selection cycles are often necessary in order to obtain the phagemids with the muteins of the invention in enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA or also from the single-stranded DNA extracted from the phagemids, the nucleic acid sequences of the selected muteins of the invention can be determined by the methods common for this purpose and the amino acid sequence can be derived therefrom. The mutated region or the sequence of the entire hNGAL mutein can be subcloned in another expression vector and expressed in a suitable host organism. PhNGAL38 can for example be used as the expression vector (cf. FIG. 3) and the expression with phNGAL38 derivatives can be performed in E. coli strains, for example E. coli-TG1. The muteins of hNGAL produced by genetic engineering can be purified by various proteinchemical methods. The hNGAL muteins produced for example with phNGAL7 carry the affinity peptide Strep-Tag II (Schmidt et al., supra) at their C-terminus and can therefore preferably be purified by streptavidin affinity chromatography.

The selection can also be carried out by means of other methods. Many corresponding embodiments are known to the person skilled in the art or are described in the literature. A combination of methods can also be applied. For example, clones selected or at least enriched by "phage display" can additionally be subjected to a "colony screening". This procedure has the advantage that individual clones can directly be isolated with respect to the production of a hNGAL mutein with detectable binding affinity for a target.

In addition to the use of E. coli as host organism in the "phage display" technique or the "colony screening" method, other bacterial strains, yeast or also insect cells or mammalian cells can for example be used for this purpose. In addition to the selection of an hNGAL mutein from a primary library produced starting from a coding nucleic acid sequence for a mutein, comparable methods can also be applied in order to optimize a mutein with respect to the affinity or specificity for the desired target by repeated, optionally limited mutagenesis of its coding nucleic acid sequence.

Once a mutein with affinity to CTLA-4 has been selected, it is additionally possible to subject such a mutein to further mutagenesis in order to select variants of even higher affinity or variants with improved properties such as higher thermostability from the new library thus obtained. This further mutagenesis, which in case of achieving higher affinity can be considered as "affinity maturation" can be achieved by site specific mutation based on rational design or a random mutation. One possible approach for obtaining a higher affinity or improved properties is the use of error-prone PCR, which results in point mutations over a selected range of sequence positions of the lipocalin mutein (cf. Example 5). The error prone PCR can be carried out in accordance with any known protocol such as the one described by Zaccolo et al. (1996) J. Mol. Biol. 255, 589-603. Other methods of random mutagenesis that are suitable for these purposes include random insertion/deletion (RED) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If wanted, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained. If the thermal stability of CTLA-4 binding lipocalin muteins is to be improved, it has been found in the present application, that the use of elevated temperature in the selection procedure, for example, when allowing complex formation between the CTLA-4-specific muteins and the target used for panning/selection, yield muteins with improved (thermal) stability (higher melting temperature) but otherwise excellent binding properties (see Example 11).

The invention is further illustrated by the following non-limiting examples and the attached drawings in which:

FIG. 1 schematically depicts the phasmid vector phNGAL35;

FIG. 2 schematically depicts the phasmid vector phNGAL37;

FIG. 3 schematically depicts the expression vector phNGAL38;

FIG. 8 shows a CTLA-4-Fc competition FACS, in which lipocalin muteins of the invention were incubated with Raji cells;

FIGS. 12a and 12b depict an antigen specific T cell proliferation assay in which human peripheral blood mononuclear cells (PBMC) were isolated and cultured with different protein antigens for 6 days in the presence of CTLA-4 Fc.

Figure 14:
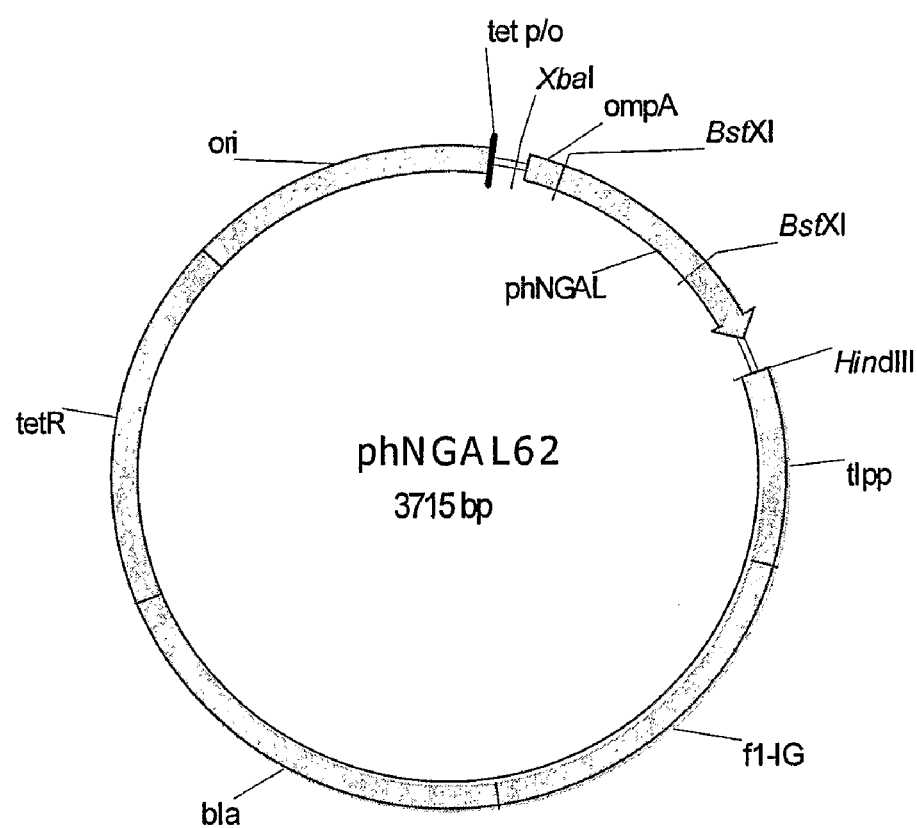

FIG. 14 schematically depicts the phasmid vector phNGAL62,

FIG. 15 shows an amino acid sequence comparison of wild type Hngal (SEQ ID NO: 79) with exemplary CTLA-4 binding lipocalin muteins (SEQ ID NOS 34-36, 38, 37, 42, 40, 41, 39, 45, 46, 43, 44, 27, 52, 25, 24, 28, 21, 22 and 26, respectively, in order of appearance) of the invention that are derived from hNGAL;

FIG. 16 shows the effect of a toxin-conjugate of the lipocalin mutein S140.4-O10 compared to a toxin-antibody-complex on the proliferation of CTLA-4 expressing CHO cells and CTLA-4 expressing A431 cells;

FIG. 17 shows a graphical representation of the mean tumor volume of four groups of 12 Balb/c mice injected with 1×10⁶ CSA1M cells s.c. and treated with several intraperitoneal injections of PBS, a mouse CTLA-4 specific monoclonal antibody 4F10 or the CTLA-4 specific lipocalin mutein S140.4-O10.

FIG. 18 depicts a mixed lymphocyte proliferation assay in which lipocalin muteins of the invention were incubated with a co-culture of purified human T cells and human JY cells for 5 days in the presence of CTLA-4 Fc.

FIG. 19 depicts a mixed lymphocyte proliferation assay in which lipocalin muteins of the invention were incubated with a co-culture of human PHA T cell blasts and human JY cells for 2 days.

FIG. 20 shows a table with results from a tissue cross-reactivity study of the lipocalin mutein S140.4-O10 binding to normal human tissues.

Figure 21:
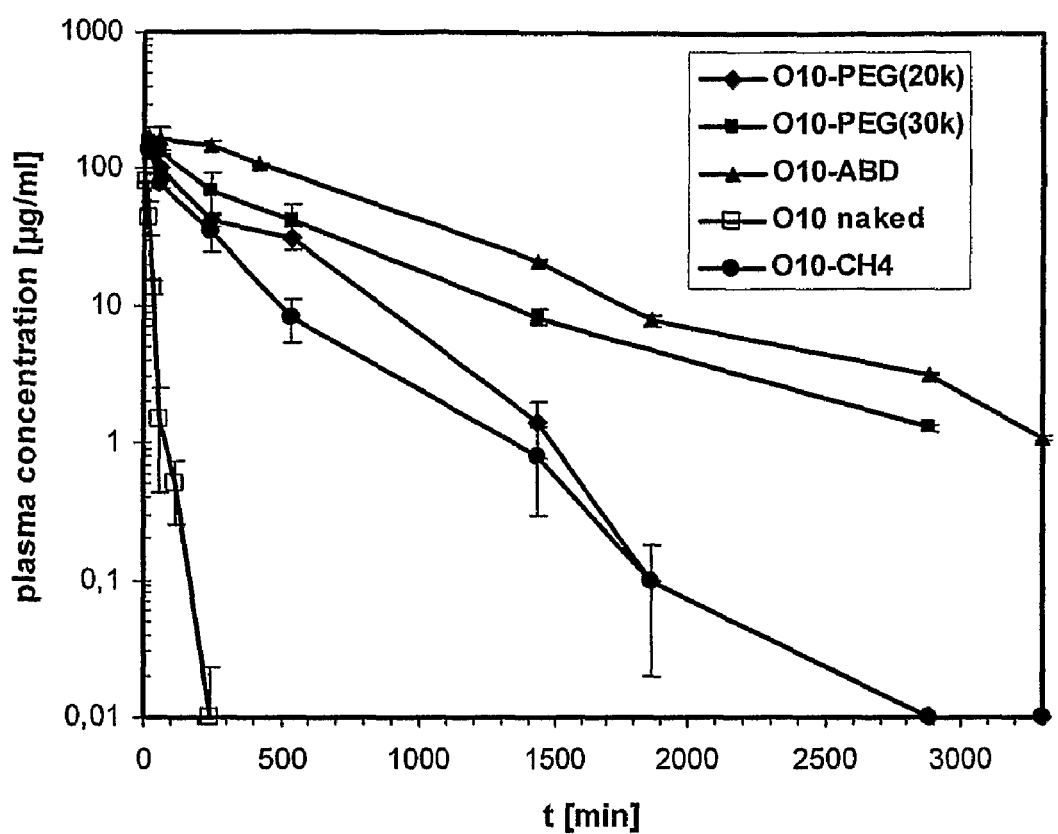

FIG. 21 is a graphical representation of the mean plasma concentration/time curve of different serum half extended formats of the CTLA-4 binding mutein S140.4-O10 compared to naked S140.4-O10 after intravenous administration in mice.

Figure 22:
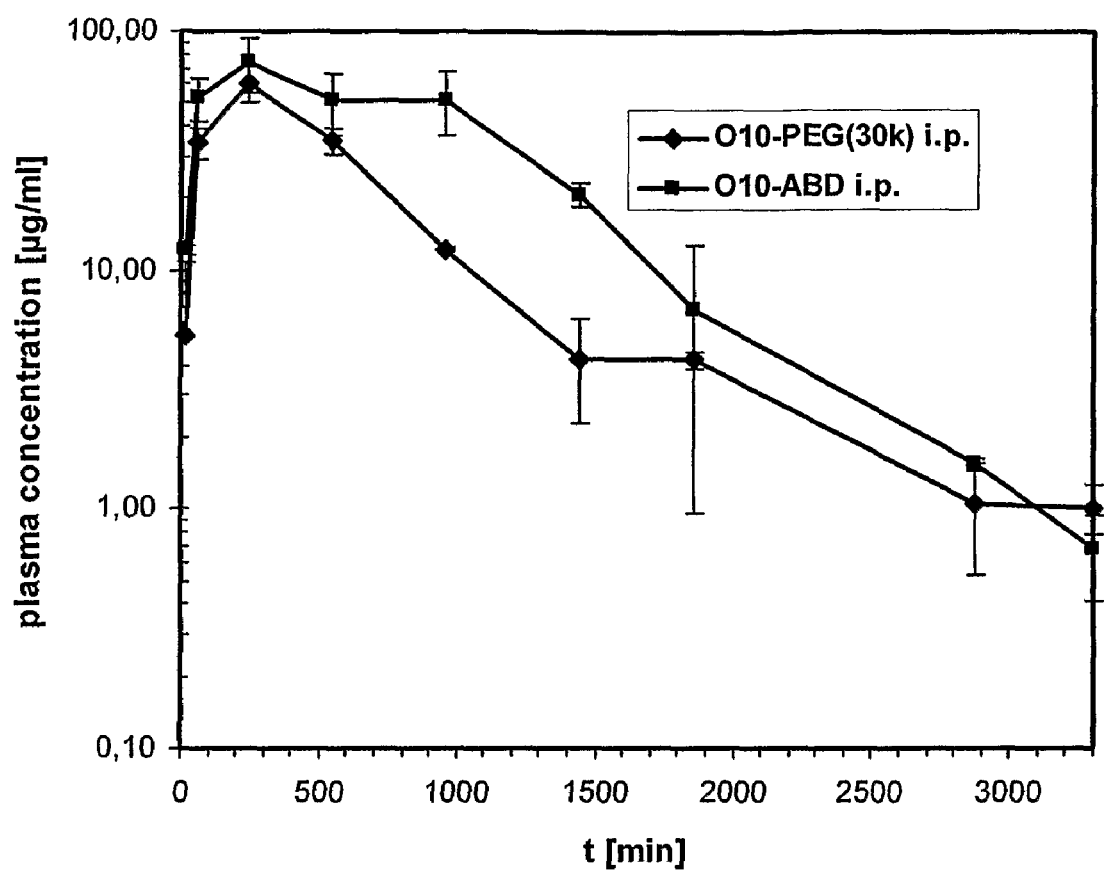

FIG. 22 is a graphical representation of the mean plasma concentration/time curve of the CTLA-4 binding mutein S140.4-O10 fused to ABD and S140.4-O10-PEG(30 k) after intraperitoneal administration in mice.

Figure 23:
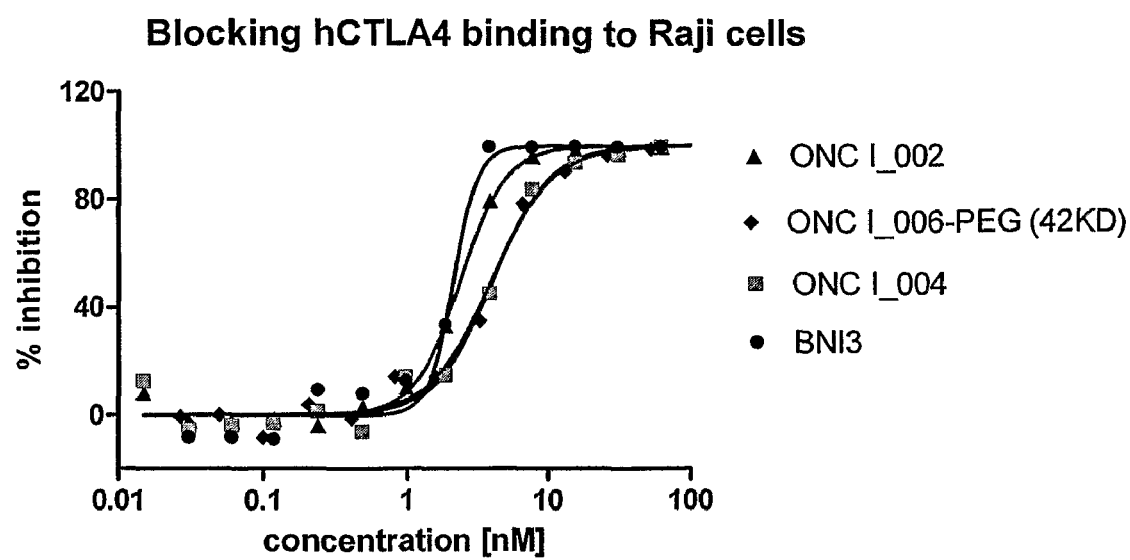
Figure 24:
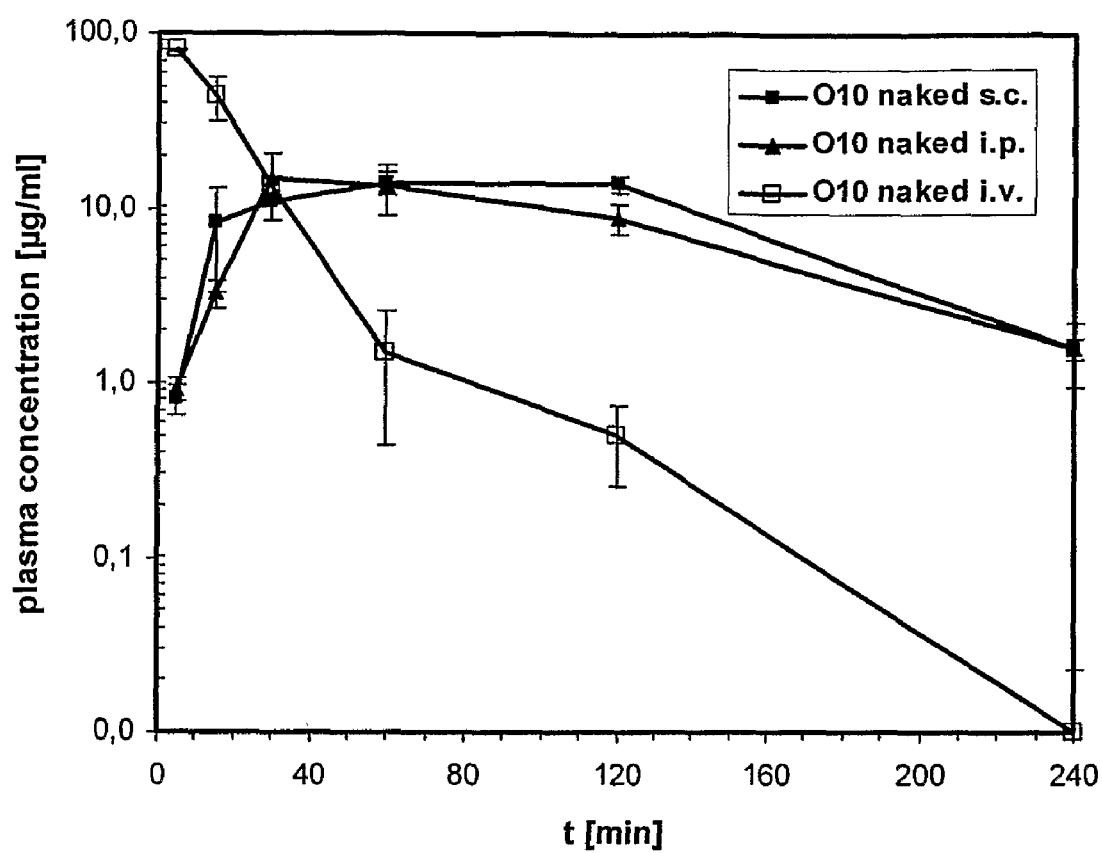

FIG. 23 shows a human CTLA-4-Fc competition FACS, in which lipocalin muteins of the invention were incubated with Raji cells;

FIG. 24 is a graphical representation of the mean plasma concentration/time curve of the CTLA-4 binding mutein S140.4-O10 after intravenous, intraperitoneal or subcutaneous administration in mice.

Figure 25:
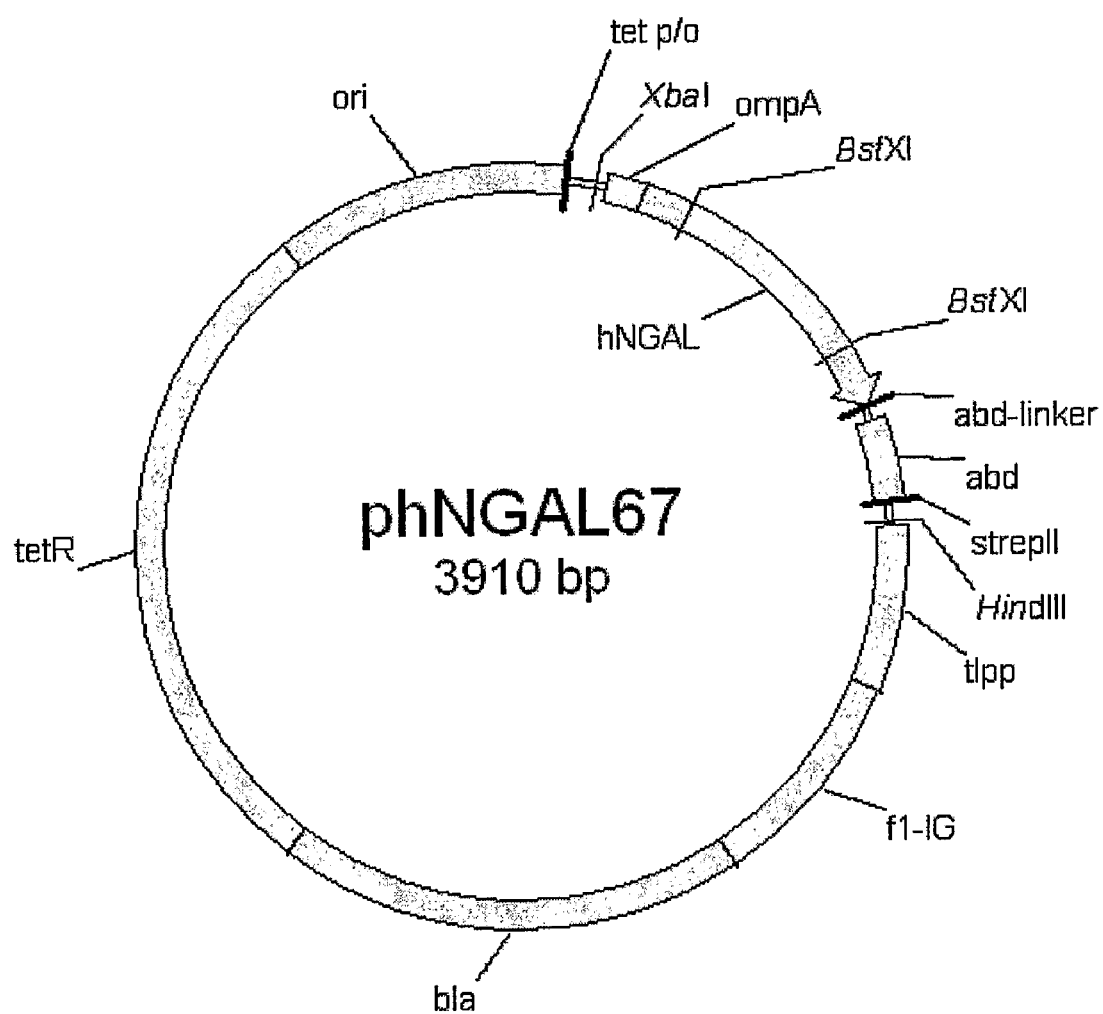

FIG. 25 schematically depicts the expression vector phNGAL67.

Figure 26:
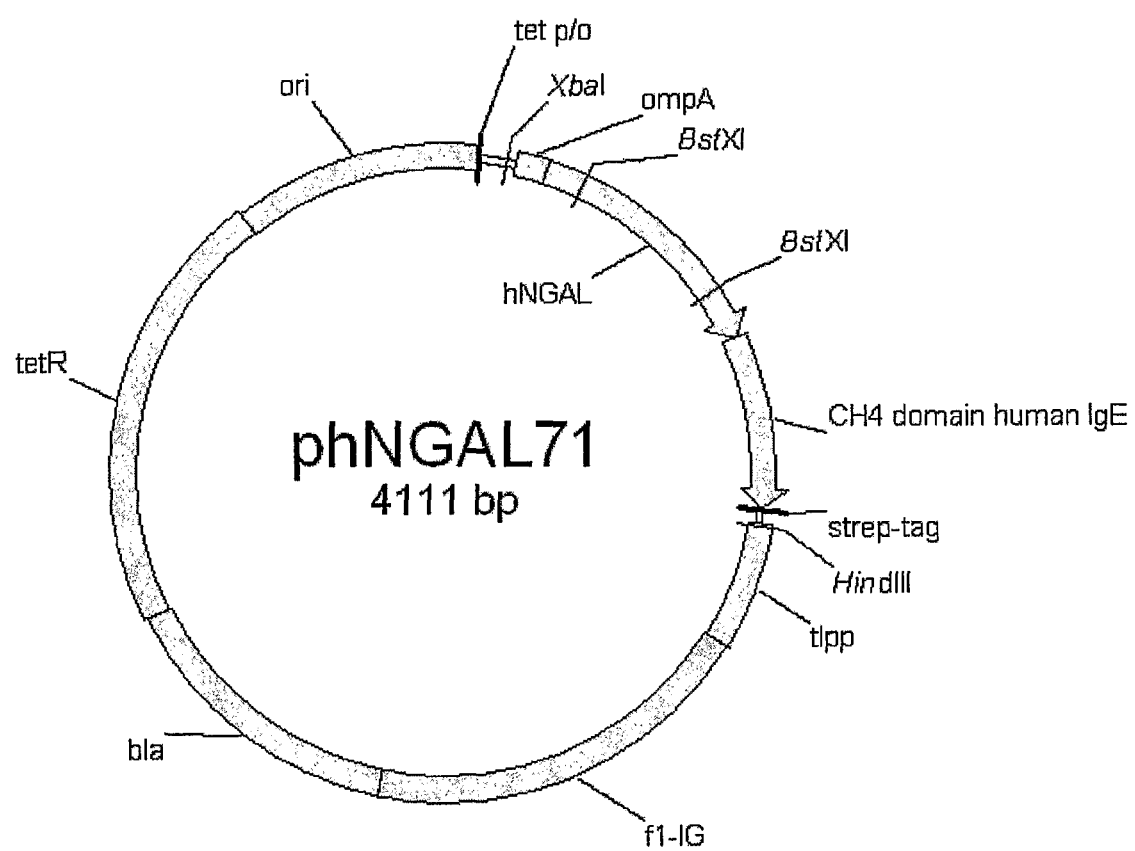

FIG. 26 schematically depicts the expression vector phNGAL71.

Figure 1:
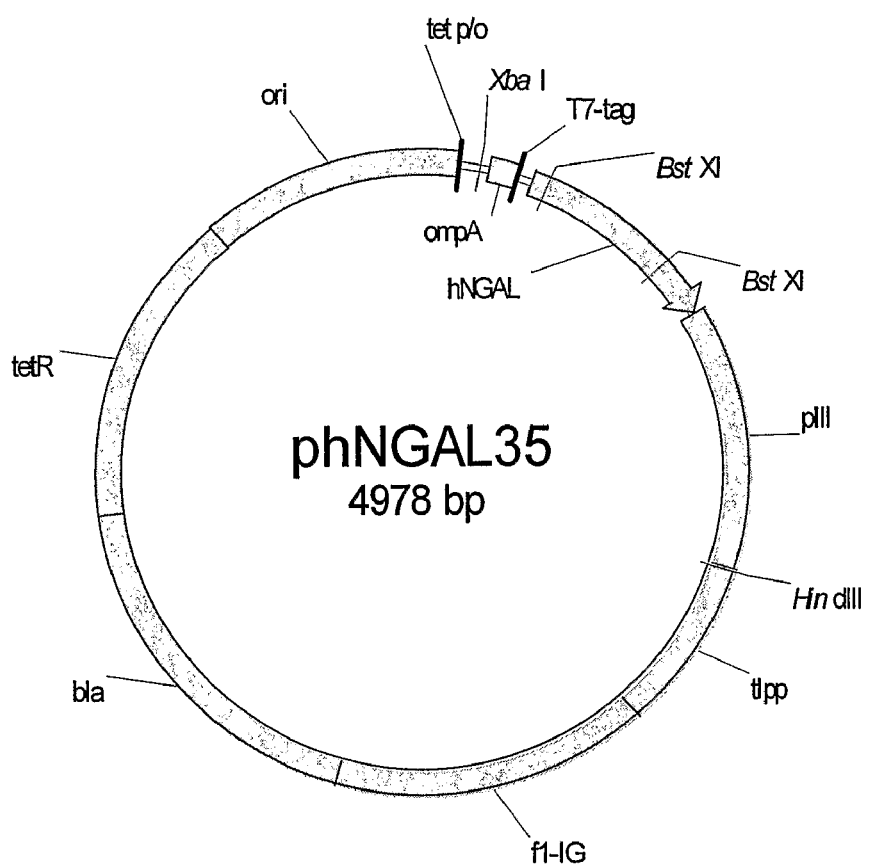

FIG. 1 shows a schematic drawing of phNGAL35. This vector codes for a fusion protein of the OmpA signal sequence, a modified hNGAL with the seven amino acid substitutions Gln28 to His, Cys87 to Ser, Leu137 to Ile, Thr145 to Ala, Arg81 to Ala, Lys125 to Ala as well as Lys134 to Ala, and the full-length M13 coat protein pIII, comprising amino acids 1 to 406 (pIII). In addition, phNGAL35 carries two silent mutations within the coding region of the OmpA signal sequence in order to remove an EcoK12 restriction site. The entire structural gene is subject to transcriptional control by the tetracycline promoter/operator (tet$^{p/o}$) and ends at the lipoprotein transcription terminator ($t_{lpp}$). Further elements of the vector comprise the origin of replication (ori), the intergenic region of the filamentous bacteriophage f1 (f1-IG), the ampicillin resistance gene (bla) coding for β-lactamase, and the tetracycline repressor gene (tetR). An amber stop codon, which is partially translated into Gln in supE amber suppressor host strains, is located between the coding region for hNGAL, fused with the OmpA signal sequence and the coding region for the pIII phage coat protein. The two BstXI restriction sites used for the cloning of the mutated gene cassette and the restriction sites flanking the structural gene are labelled. A relevant segment of the nucleic acid sequence of phNGAL35 is reproduced together with the encoded amino acid sequence in the sequence listing as SEQ ID NO:5. The segment begins with the XbaI restriction site and ends with the HindIII restriction site. The vector elements outside this region are identical with the vector pASK75, the complete nucleotide sequence of which is given in the German patent publication DE 44 17 598 A1.

Figure 2:
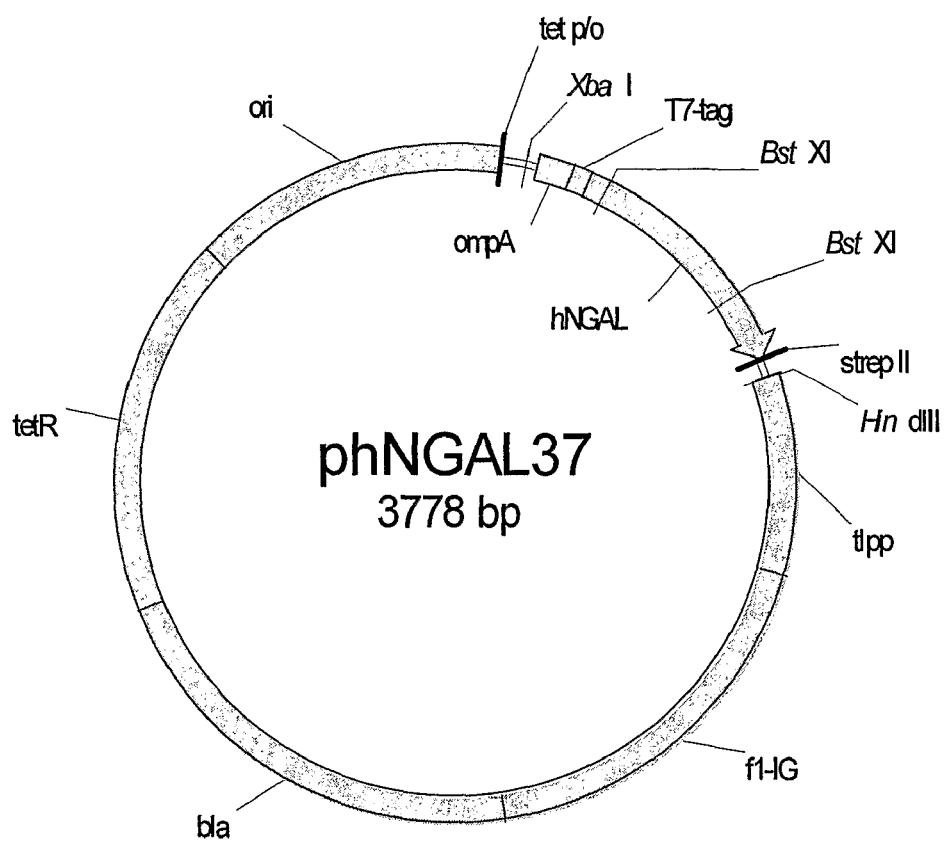

FIG. 2 shows a schematic drawing of phNGAL37. phNGAL37 codes for a fusion protein of the OmpA-signal sequence, followed by a T7-affinity-tag (T7) with a modified hNGAL according to FIG. 1 (phNGAL35) and the Strep-Tag® II affinity tag. phNGAL37 carries the same silent mutations within the coding region of the OmpA signal sequence as phNGAL35. A relevant segment of the nucleic acid sequence of phNGAL37 is reproduced together with the encoded amino acid sequence in the sequence listing as SEQ ID NO:6. The segment begins with the XbaI restriction site and ends with the HindIII restriction site. The vector elements outside this region are identical with the vector pASK75, the complete nucleotide sequence of which is given in the German patent publication DE 44 17 598 A1.

Figure 3:
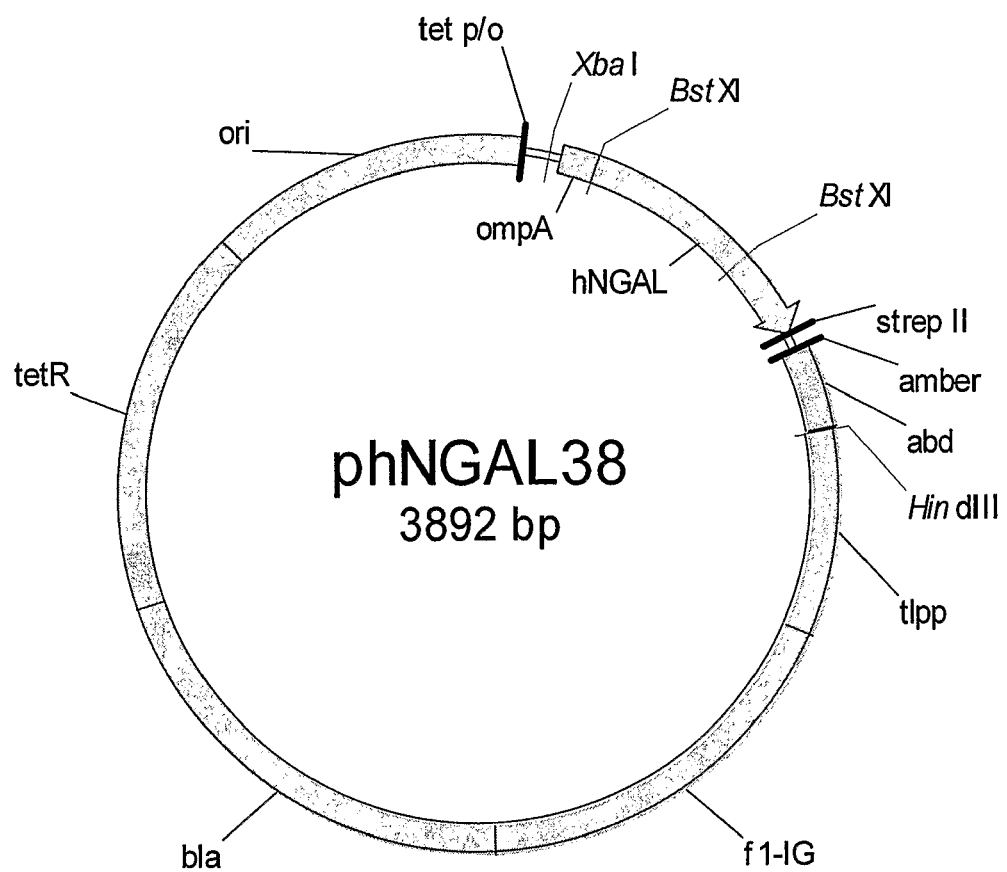

FIG. 3 shows a schematic drawing of phNGAL38. This vector codes for a fusion protein of the OmpA signal sequence, a modified hNGAL according to FIG. 1 (phNGAL35), the Strep-Tag® II and an albumin-binding domain (abd) of protein G from *Streptococcus* (Kraulis et al. (1996) *FEBS Lett.* 378, 190-194). An amber stop codon has been introduced between the Strep-Tag® II and the C-terminal albumin binding domain to allow soluble expression of the hNGAL mutein without the ABD when employing a non-suppressor *E. coli* strain. A relevant segment of the nucleic acid sequence of phNGAL38 is reproduced together with the encoded amino acid sequence in the sequence listing as SEQ ID NO: 7. The segment begins with an XbaI restriction site and ends with the HindIII restriction site. The vector elements outside this region are identical with those of the vector pASK75, the complete nucleotide sequence of which is exhibited in the German patent publication DE 44 17 598 A1.

Figure 4:
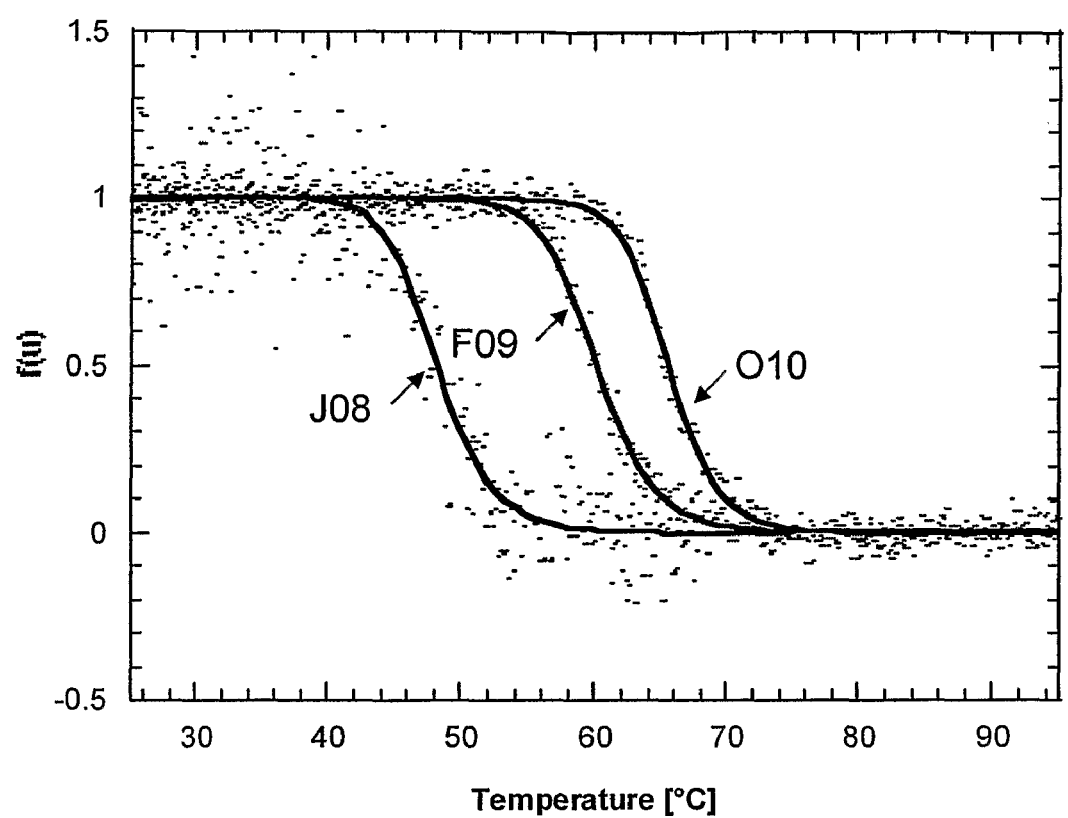
FIG. 4 depicts circular dichroism spectra of purified CTLA-4-specific lipocalin muteins of the invention used for determining the melting temperature of the lipocalin muteins.

FIG. 4 shows circular dichroism spectra of purified CTLA-4-specific lipocalin muteins J08, F09 and O10 displaying the transition from folded to unfolded state. The unfolded protein fraction f(u) was plotted as a function of temperature T to determine the melting temperature Tm of each lipocalin mutein.

Figure 5:
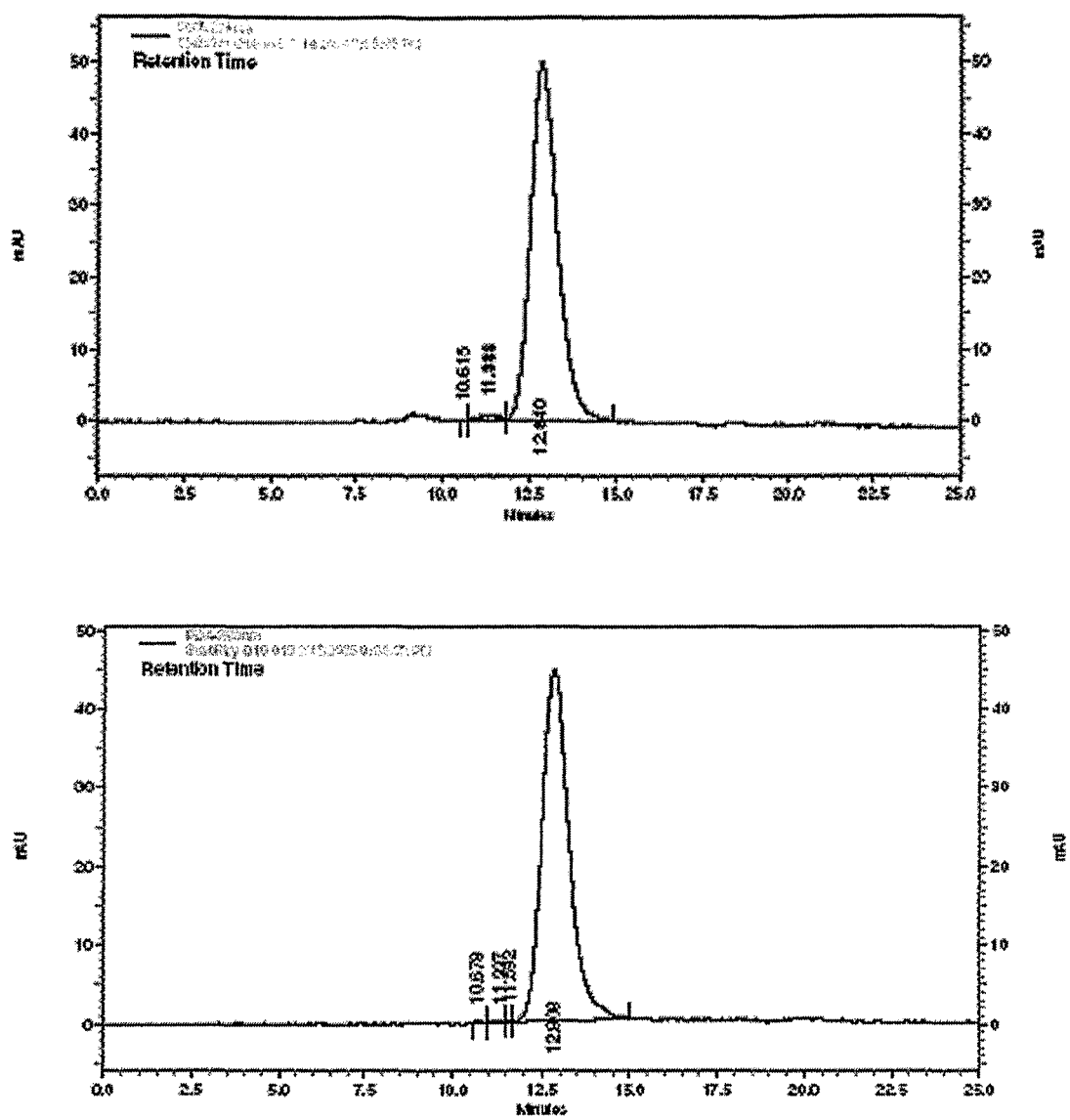
FIG. 5 depicts Size Exclusion HPLC chromatograms of the CTLA-4 binding hNGAL mutein S140.4-O10 under physiological conditions.

FIG. 5 shows the stability of the S140.4-O10 in PBS using HPLC-SEC (SEC—size exclusion chromatography)). The mutein S140.4-O10 was incubated at 10 mg/ml (upper diagram) respectively 0.5 mg/ml (lower diagram) in PBS for 7 days at 37° C. in concentrations of 10 mg/ml and 0.5 mg/ml in PBS, pH 7.4.

Figure 6:
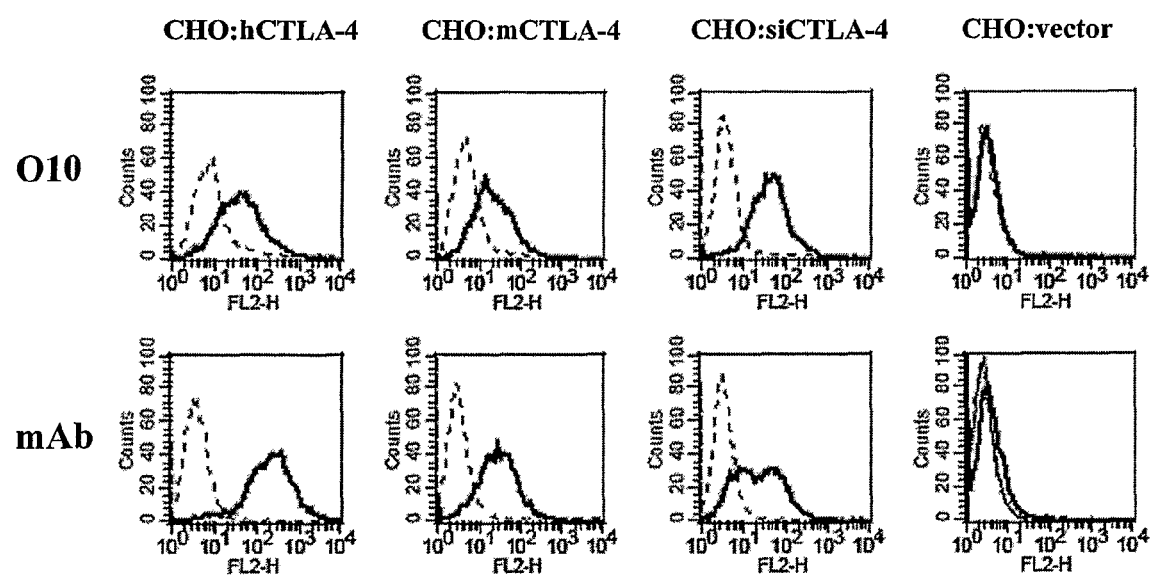
FIG. 6 depicts FACS histogram representations of stained CHO cells expressing human, murine, simian CTLA-4 or no cDNA.

FIG. 6 shows FACS histogram representations of stained CHO cells expressing human, murine, simian CTLA-4 or no cDNA. CHO cells transfected with the expression vector human CTLA-4 pcDNA3.1 ZEO(+) (CHO-hCTLA-4; first column), murine CTLA-4 pcDNA3.1 ZEO(+) (CHO: mCTLA-4; second column), cynomolgous CTLA-4 pcDNA3.1 ZEO(+) (CHO:siCTLA-4; third column), or the empty expression vector pcDNA3.1ZEO(+) (CHO:empty vector; fourth column) were incubated with the lipocalin mutein S140.4-O10 (upper row, thick line) or control antibodies (lower row, thick line). In parallel, these cell lines were incubated with the negative control Lipocalin hNGALwt-58 (upper row, dashed line) or isotype matched control antibodies (lower row, dashed line). S140.4-O10 shows same as the antibody used as positive control specific staining of the CHO cell line expressing human, mouse and cynomolgous CTLA-4, whereas no binding is observed for the vector control cells.

Figure 7A:
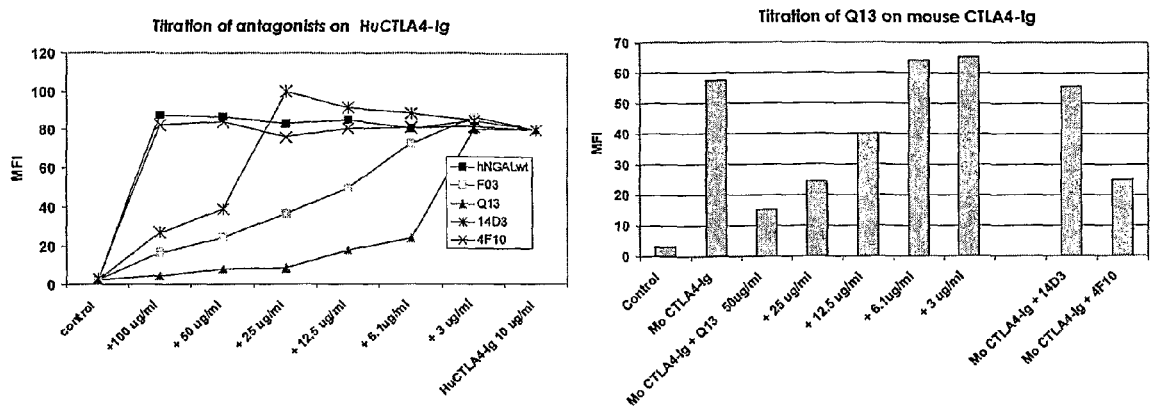
FIG. 7 shows a CTLA-4-Fc competition FACS in which lipocalin muteins of the invention were incubated with B7.2 transfected P815 cells.

FIG. 7A shows the results of the following CTLA-4-Fc competition FACS: 10 µg/ml human CTLA-4 Fc (huCTLA-4-Ig, left line graph) or 5 µg/ml mouse CTLA-4 Fc (muCTLA-4-Ig, right bar graph) were pre-incubated with 100/50/25/12/6/3/0 µg/ml of the lipocalin muteins S67.2-F03 (F03) and S94.7-Q13 (Q13) or control antibodies anti-human CTLA-4 14D13 (14D3) and anti-mouse CTLA-4 4F10 (4F10) in PBS/BSA for 1 h at RT and incubated with P815 cells, transfected with a cDNA for human B7.2 (CD86) on ice for 30 minutes. A B7.2 specific monoclonal antibody chFUN1 was used in addition to confirm B7.2 expression (data not shown). Detection of bound huCTLA-4 Fc and muCTLA-4 was performed via anti-human or anti-mouse IgG-phycoerythrin conjugate respectively. Specific B7.2 staining by CTLA-4 Fc is reported as mean fluorescence intensity (MFI).

Figure 7B:
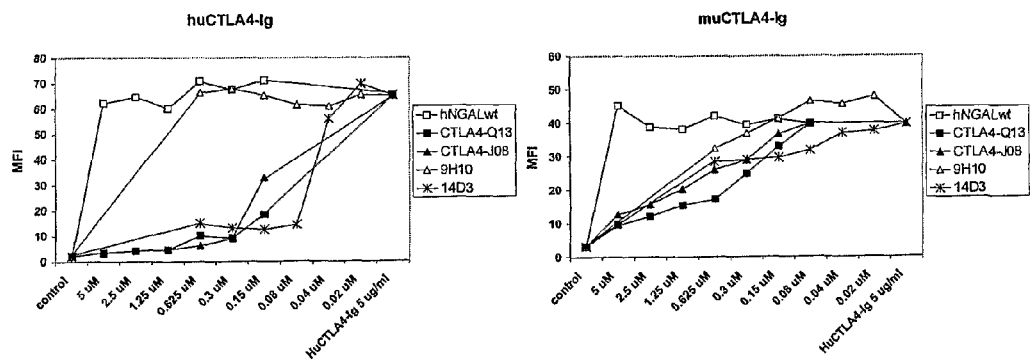

FIG. 7B shows the result of a CTLA-4 Fc competition FACS that was carried out as follows: 10 µg/ml human CTLA-4 Fc (huCTLA-4-Ig, left side) or 5 µg/ml mouse CTLA-4 Fc (muCTLA-4-Ig, right side) were pre-incubated with 100/50/25/12/6/3/0 µg/ml lipocalin muteins S94.7-Q13 (CTLA-4-Q13) and F92.1-J08 (CTLA-4-J08) or control antibodies anti-human CTLA-4 14D13 (14D3) and anti-mouse CTLA-4 4F10 (4F10) in PBS/BSA for 1 h at RT and incubated with P815 cells, transfected with a cDNA for human B7.2 (CD86) on ice for 30 minutes. A B7.2 specific monoclonal antibody chFUN1 was used in addition to confirm B7.2 expression (data not shown). Detection of bound huCTLA-4 Fc and muCTLA-4 Fc was performed via anti-human or anti-mouse IgG-phycoerythrin conjugate respectively. Specific B7.2 staining by CTLA-4 Fc is reported as mean fluorescence intensity (MFI).

FIG. 8 depicts the following CTLA-4 Fc competition FACS: 2.5 nM human CTLA-4 Fc or mouse CTLA-4 Fc were pre-incubated with the lipocalin mutein S140.4-O10 (O10) a control lipocalin hNGAL-58 (hNGal) (hNGAL wt58 is the protein shown as SEQ ID NO:74 the coding sequence of which is derived from the small BstX1 fragment from phNGAL15 and the large BstX1 fragment from phNGAL37) or human CTLA-4 specific antibodies 14D3 and BNI3 or the mouse CTLA-4 specific antibody 4F10 at the indicated final concentrations in PBS/BSA for 30 min at RT and incubated with Raji cells on ice for 30 minutes. Detection of bound human CTLA-4 Fc and mouse CTLA-4 Fc was performed via anti-human IgG-phycoerythrin or anti-mouse IgG-phycoerythrin conjugate respectively. Specific B7.1/2 staining by CTLA-4-Fc is reported as the geometric mean of the fluorescence intensity (MFI). A sigmoidal dose response model was used to fit the data with the program Prism (GraphPad) and to calculate IC50 values.

Figure 9:
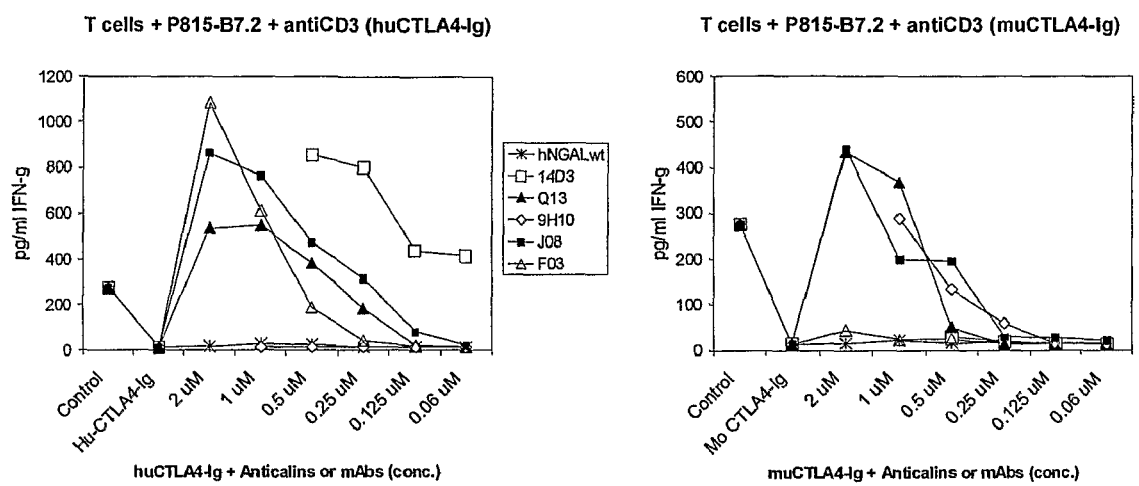
FIG. 9 depicts the results of a T cell costimulation assay in which human peripheral blood T were coincubated with $10^4$ P815 cells transfected with a cDNA for human B7.2 (CD86)+ antiCD3 1 µg/ml for 48 hours in the presence of CTLA-4 Fc.

FIG. 9 shows a T cell costimulation assay in which 105 human peripheral blood T cells (>90% pure) were co-incubated with $10^4$ P815 cells transfected with a cDNA for human B7.2 (CD86)+antiCD3 mAb 1 µg/ml for 48 hours. Human CTLA-4 Fc (huCTLA-4-Ig, 10 µg/ml) or mouse CTLA-4 Fc (muCTLA-4-Fc, 5 µg/ml) were pre-incubated with various concentrations of the lipocalin muteins S67.2-F03 (F03), F92.1-J08 (J08), S94.7-Q13 (Q13) or control antibodies 14D3 or 9H10 and added at the start of the cultures as indicated. The same legend applies for both graphs. Levels of INFγ in cell culture supernatant were determined by a commercial sandwich ELISA.

Figure 10:
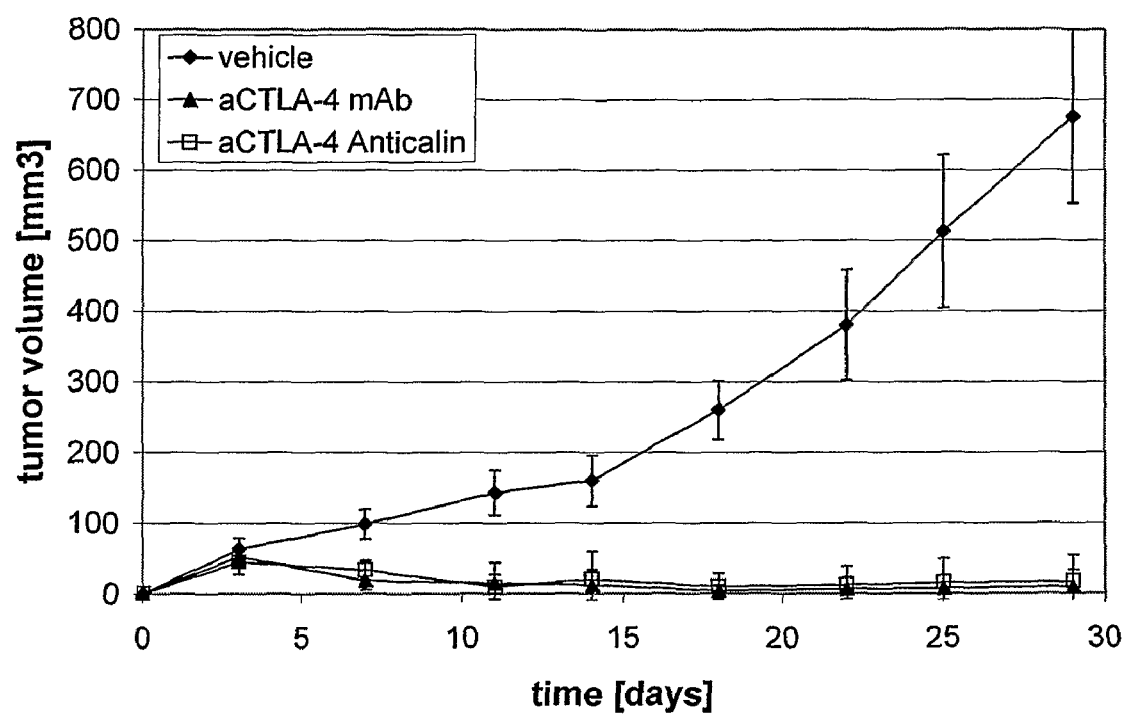
FIG. 10 shows a graphical representation of the mean tumor volume of three groups of Balb/c mice injected with 1×10⁶ CSA1M cells s.c. and treated with PBS (vehicle), the mouse CTLA-4 specific monoclonal antibody 4F10 (aCTLA-4 mAb) or the CTLA-4 specific hNGAL mutein F92.1-J08.

FIG. 10 shows a graphical representation of the mean tumor volume $(V=(W^2 \times L)/2)+/-SD$ of three groups of 12 Balb/c mice injected with $1 \times 10^6$ CSA1M cells s.c. and treated with PBS (vehicle, filled rhombes), a mouse CTLA-4 specific monoclonal antibody 4F10 (aCTLA-4 mAb, filled triangles) or the CTLA-4 specific lipocalin mutein F92.1-J08 ("aCTLA-4 Anticalin", open squares) according to the protocol described in Example 22.

Figure 11:
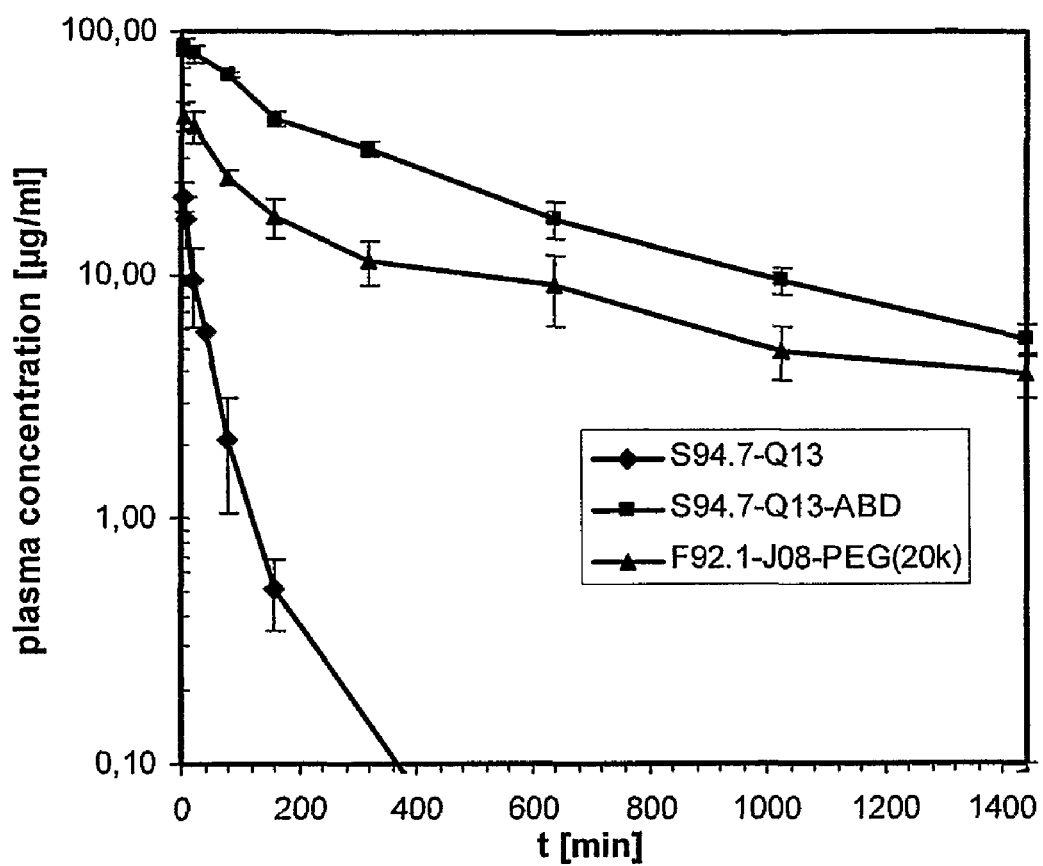
FIG. 11 is a graphical representation of the mean plasma concentration/time curve of PEGylated CTLA-4 binding mutein F92.1-J08, the CTLA-4 binding mutein S94.7-Q13 and the CTLA-4 binding mutein S94.7-Q13 being fused to an albumin binding domain—(ABD) after intravenous administration in mice.

FIG. 11 shows a graphical representation of the mean plasma concentration/time curve (arithm. means±SD) of the CTLA-4 binding mutein S94.7-Q13 (filled rhombes) and a fusion protein of the mutein S94.7-Q13 with the albumin-binding domain of protein G from Streptococcus (S94.7-Q13-ABD, filled squares) after single intravenous injection of 2.5 mg/kg. FIG. 11 also shows the mean plasma concentration of the CTLA-4 binding mutein F92.1-J08 PEGylated with linear 20 kDa-mPEG-NHS ester (F92.1-J08-PEG, filled triangles) after single intravenous injection of 2.0 mg/kg F92.1-J08-PEG to mice.

Figure 12A:
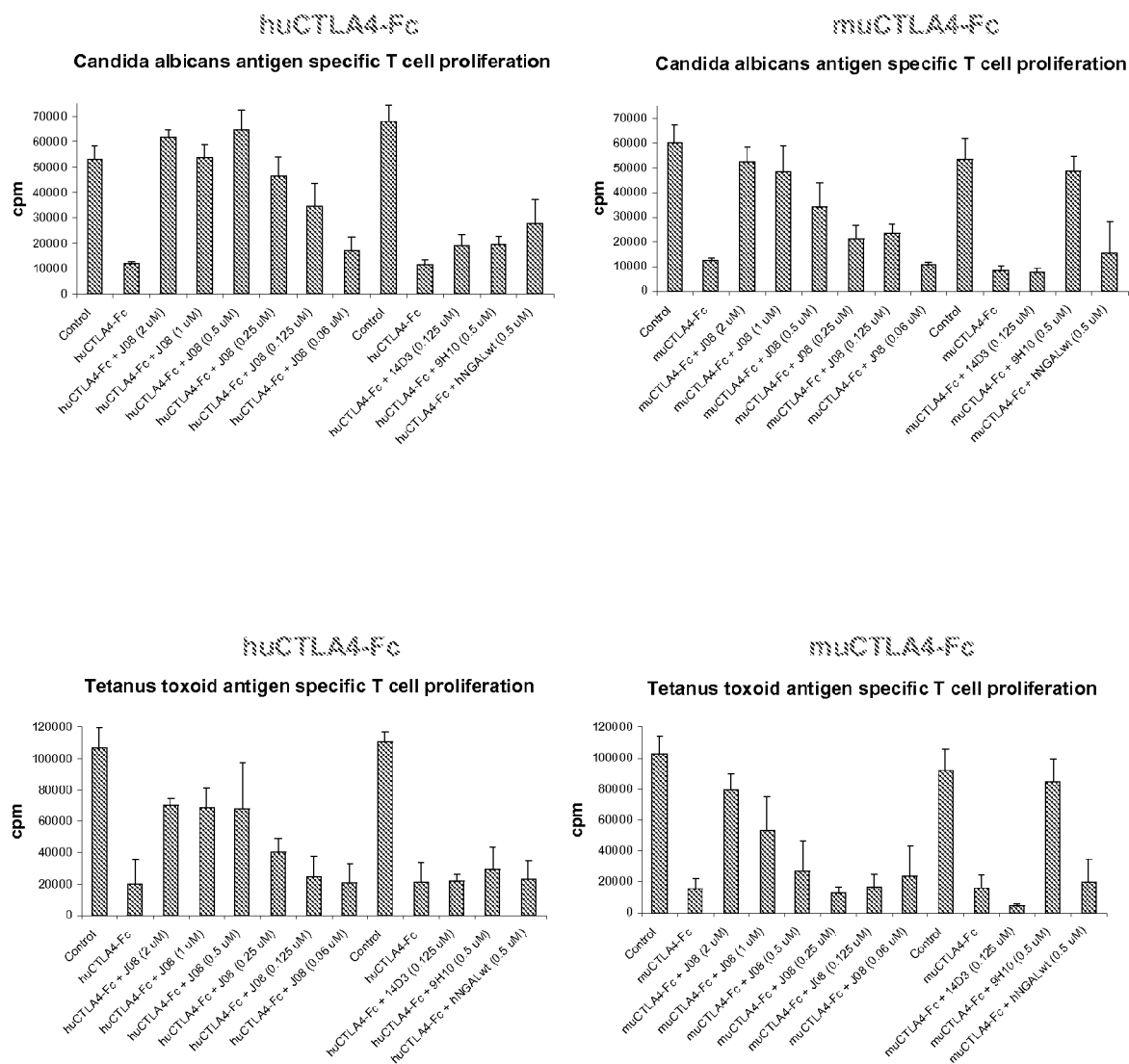

FIG. 12a shows the following antigen specific T cell proliferation assay: Human peripheral blood mononuclear cells (PBMC) were isolated and cultured with candida albicans antigen (upper row) or tetanus toxoid antigen (lower row) for 6 days. Antigen-specific T cell proliferation induced by peptide-MHC complexes presented by antigen presenting cells in the cultures were measured in a standard 3H-thymidine incorporation assay. Human CTLA-4 Fc (huCTLA-4-Fc, left column) or mouse CTLA-4 Fc (muCTLA-4-Fc) were added at the start of the culture. The lipocalin mutein F92.1-J08 and control antibodies were added to some of the cultures in the final concentrations as indicated in the graph.

FIG. 12b shows the following antigen-specific T cell proliferation assay: $2 \times 10^5$ PBMC were cultured in the presence of Tetanus toxoid (upper row) or Candida albicans (lower row)+5 µg/ml human CTLA-4 Fc+/- lipocalin muteins or mAbs as indicated. Preparations of the lipocalin mutein S140.4-O10 (O10 724, O10 717/730), the lipocalin hNGAL-58 (WT58 new, WT58 732), the human CTLA-4 specific monoclonal antibody BNI3 and a matching isotype control (aCD14) were used at the concentrations indicated. After 6 days $^3$H-thymidine was added to measure T cell proliferation. Values shown are the result of $^3$H-thymidine incorporation and are expressed as cpm. Error bars represent standard deviation of triplicate cultures.

Figure 13:
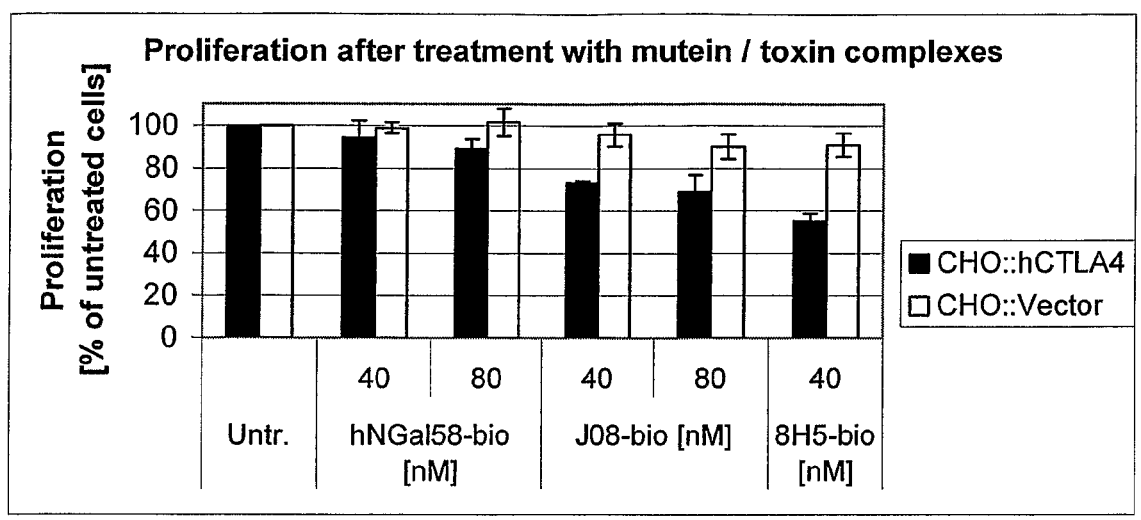
FIG. 13 shows the effect of a toxin-complex of the lipocalin mutein J08 compared to a toxin-antibody-complex on the proliferation of CTLA-4 expressing CHO cells.

FIG. 13 shows the effect of a toxin-complex of the lipocalin mutein F92.1-J08 compared to a toxin-antibody-complex on the proliferation of CTLA-4 expressing CHO cells. The figure shows a graphical representations of the mean proliferation values+/−SD of triplicate cell culture wells of hCTLA-4 transfected CHO cells (CHO::hCTLA-4) and vector control transfected CHO cells (CHO::Vector) after incubation with lipocalin mutein or antibody saporin complexes for three days in comparison to untreated (untr) cells. Cells were incubated with the biotinylated lipocalin muteinF92.1_J08 (J08-bio), hNGAL-58 (hNGal58-bio) or the monoclonal antibody 8H5 (8H5-bio) as described in example 28.

FIG. 14 depicts a schematic drawing of phNGAL62. phNGAL62 codes for a fusion protein of the OmpA-signal sequence with a modified hNGAL according to FIG. 1 (phNGAL35). phNGAL62 carries the same silent mutations within the coding region of the OmpA signal sequence as phNGAL62. A relevant segment of the nucleic acid sequence of phNGAL62 is reproduced together with the encoded amino acid sequence in the sequence listing as SEQ ID NO:55. The segment begins with the XbaI restriction site and ends with the HindIII restriction site. The vector elements outside this region are identical with the vector pASK75, the complete nucleotide sequence of which is given in the German patent publication DE 44 17 598 A1.

FIG. 15 shows a comparison of the amino acid sequence of wildtyp hGNAL (SEQ ID NO: 79) with exemplary CTLA-4 binding lipocalin muteins (SEQ ID NOS 34-36, 38, 37, 42, 40, 41, 39, 45, 46, 43, 44, 27, 52, 25, 24, 28, 21, 22 and 26, respectively, in order of appearance) of the invention that are derived from hNGAL. The sequence positions 40, 42, 44, 46, 47, 49, 50, 70, 71, 72, 77, 79, 101, 102, 103, 125, 127, 128, 130, and 132 of HNGAL which were subjected to mutagenesis for the initial generation of CTLA-4 binding lipocalin muteins are indicated in bold.

Figure 16A:
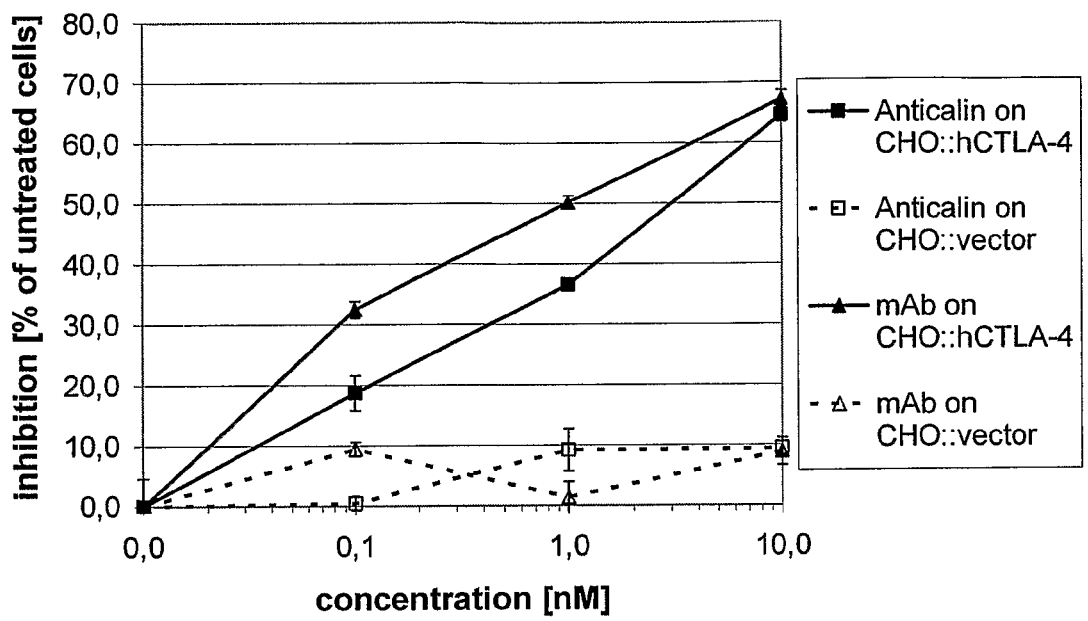

FIG. 16 shows the effect of a toxin-conjugate of the lipocalin mutein S140.4-O10 compared to a toxin-antibody-complex on the proliferation of CTLA-4 expressing CHO cells. FIG. 16a shows a graphical representations of the mean inhibition of proliferation in percent+/−SD in relation to untreated cells of triplicate cell culture wells of hCTLA-4 transfected CHO cells (CHO::hCTLA-4) and vector control transfected CHO cells (CHO::vector) after incubation with lipocalin mutein S140.4-O10-saporin (1:2 ratio) or biotinylated antibody (8H5-bio) neutravidin-saporin complexes (1:1 ratio of 8H5-bio to neutravidin-saporin) for three days. Cells were incubated with the test substances as described in Example 29.

Figure 16B:
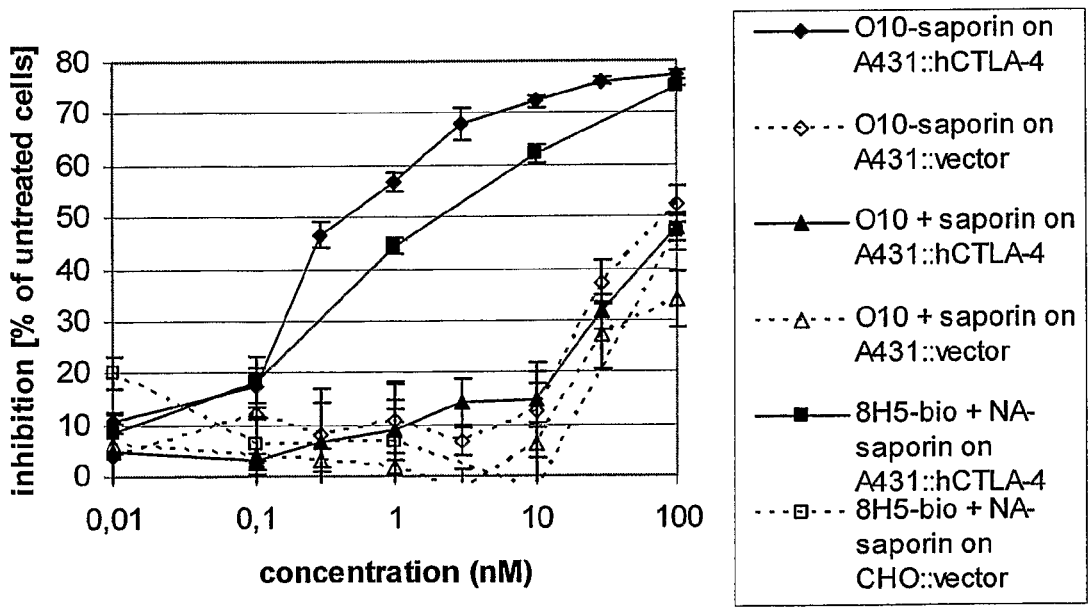

FIG. 16b shows a graphical representations of the mean inhibition of proliferation in percent+/−SD in relation to untreated cells of triplicate cell culture wells of hCTLA-4 transfected A431 cells (A431::hCTLA-4) and vector control transfected A3431 cells (A431::vector) after incubation with lipocalin mutein S140.4-O10-saporin (1:1 ratio), non-conjugated lipocalin mutein S140.4-O10 plus free saporin or biotinylated antibody (8H5-bio) neutravidin-saporin complexes (1:1 ratio of 8H5-bio to neutravidin-saporin) for three days. Cells were incubated with the test substances as described in Example 29.

Figure 17A:
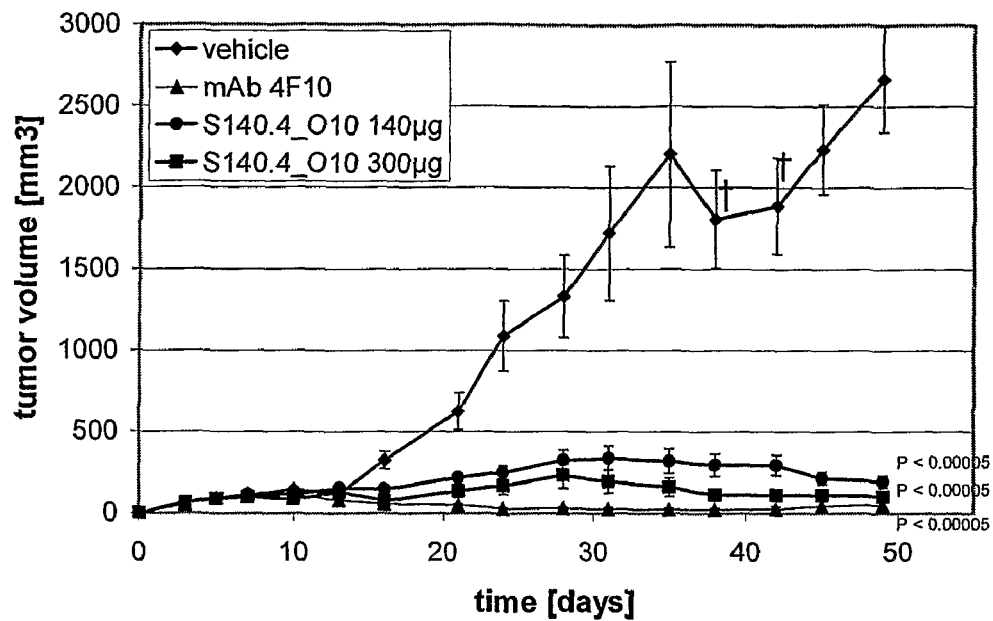

FIG. 17A shows a graphical representation of the mean tumor volume (V=(W$^2$×L)/2)+/−SEM of four groups of 12 Balb/c mice injected with 1×10$^6$ CSA1M cells s.c. and treated with several intraperitoneal injections of PBS (filled diamonds), a mouse CTLA-4 specific monoclonal antibody 4F10 (filled triangle) or the CTLA-4 specific lipocalin mutein S140.4-O10 using 140 μg (filled circle) or 300 μg (filled square) per injection according to the protocol described in Example 23. P values obtained from a student t test of pairwise comparisons between indicated groups with the PBS treated group are also included in FIG. 17A. Cross symbols in the graph indicate sacrifice of individual mice at indicated days in the PBS treated group for humane reasons due to excessive tumor growth.

Figure 17B:
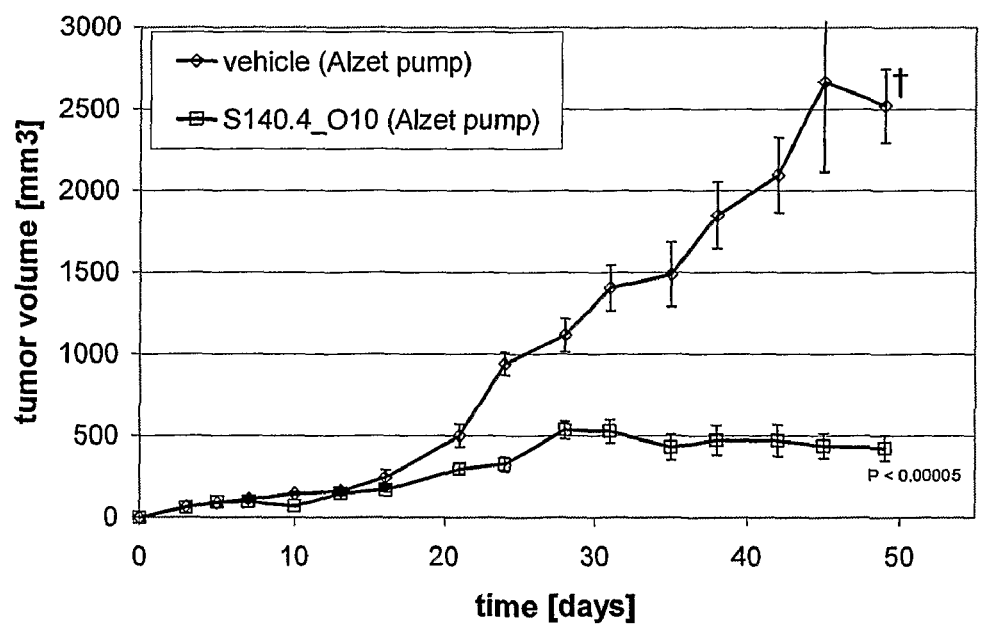

FIG. 17B shows a graphical representations of the mean tumor volume (V=(W$^2$×L)/2)+/−SEM of two groups of 12 Balb/c mice injected with 1×10$^6$ CSA1M cells s.c treated with PBS (empty diamonds) or S140.4-O10 (empty circle) loaded Alzet pumps implanted subcutaneously as described in example 23. The p value obtained from a student t test of a pair-wise comparison between S140.4-O10 treated and PBS treated group is also included in FIG. 17B. Cross symbols in the graph indicate sacrifice of individual mice at indicated days in the PBS treated group for humane reasons due to excessive tumor growth.

FIG. 18 shows the following mixed lymphocyte reaction assay: 5000 human JY cells/well were cocultured with 105 purified human T cells in the presence of 5 μg/ml human CTLA-4 Fc (top row) or mouse CTLA-4 Fc (bottom row)+/−lipocalin muteins or monoclonal antibodies in the final concentrations as indicated. Two independent batches of the mutein S140.4-O10 "O10" and hNGALwt-58 "WT58" were tested and compared to the human CTLA-4 specific monoclonal antibody BNI3 and a matched isotype control antibody (aCD14). $^3$H-thymidine was added to measure T cell proliferation after 5 days. Values shown are the result of $^3$H-thymidine incorporation and are expressed as cpm. Error bars represent standard deviation of triplicate cultures.

Figure 19A:
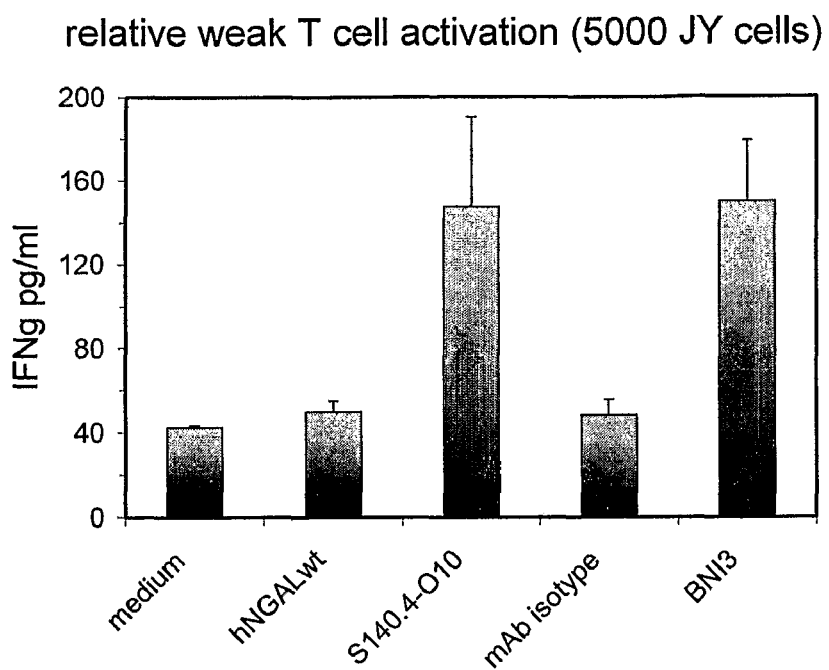
Figure 19B:
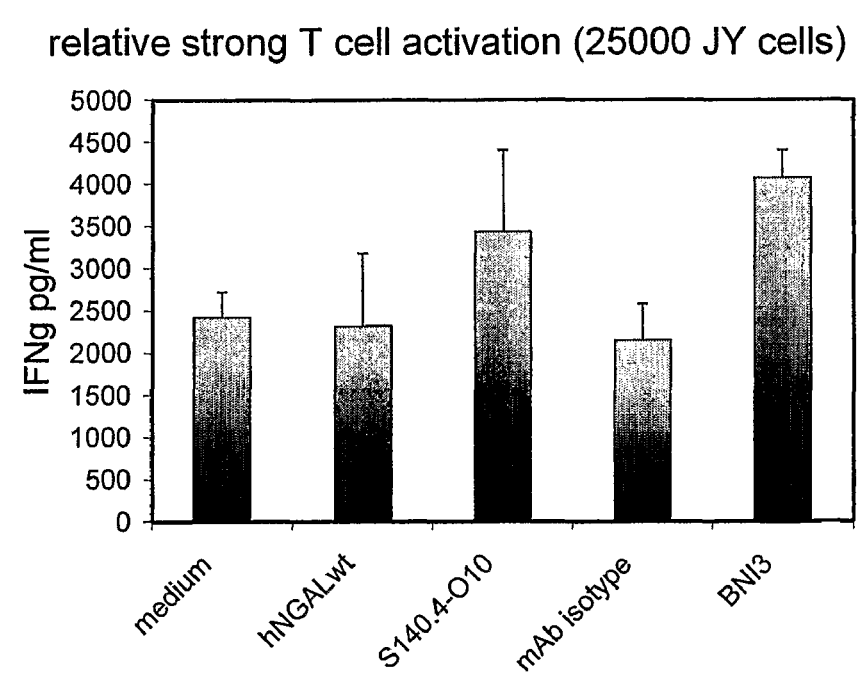

FIG. 19 shows the following mixed lymphocyte reaction assay: 5000 human JY cells/well (FIG. 19a) or 25000 human JY cells/well (FIG. 19b) were cocultured with 10$^5$ human PHA T cells blasts for 48 hours. Values shown are the result of INFγ measured in cell culture supernatants and are expressed as pg/ml. Error bars represent standard deviation of triplicate cultures. The lipocalin mutein S140.4-O10 and hNGALwt were tested and compared to the human CTLA-4 specific monoclonal antibody BNI3 or a matching isotype control antibody.

FIG. 20 shows a table with results from a tissue cross-reactivity study of the lipocalin mutein S140.4-O10 binding to normal human tissues. The test article, positive control antibody and isotype controls have been used as described in example 31 on normal human tissue sections as indicated in the table.

FIG. 21 shows a graphical representation of the mean plasma concentration/time curve (arithm. means±SD) of the CTLA-4 binding mutein S140.4-O10 (open squares), a fusion protein of the mutein with the albumin-binding domain of protein G from Streptococcus (S140.4-O10-ABD, filled triangles), and a dimerized fusion of the mutein to the Fc-portion of human IgE (filled circles) after single intravenous injection of 7.5 mg/kg to mice. FIG. 21 also shows the mean plasma concentration of the CTLA-4 binding mutein PEGylated with linear 20 kDa-PEG-maleimide (S140.4-O10-PEG (20 k), (filled rhombes) and 30 kDa-PEG-maleimide (S140.4-O10-PEG (30 k), filled squares) after single intravenous injection of 7.5 mg/kg to mice.

FIG. 22 is a graphical representation of the mean plasma concentration/time curve of the CTLA-4 binding mutein S140.4-O10 fused to ABD (filled rhombes) and the site-directly PEGylated mutein S140.4-O10-PEG(30 k) (filled squares) after single intraperitoneal injection of 7.5 mg/kg to mice in order to investigate bioavailability of serum half extended formats.

FIG. 23 depicts the following CTLA-4 Fc competition FACS: 2.5 nM human CTLA-4 Fc were pre-incubated with the lipocalin mutein S140.4-O10 (Onc I_002), S140.4-O10-20 kD PEG (Onc I_006-PEG 42 kD), S140.4-O10 fused to ABD (Onc I-004) or human CTLA-4 specific antibodies BNI3 at the indicated final concentrations in PBS/BSA for 30 min at RT and incubated with Raji cells on ice for 30 minutes. Detection of bound human CTLA-4 Fc was performed via an anti-human IgG-phycoerythrin conjugate. Geometric mean values of the fluorescence intensity (MFI) of stained cells were used to calculate % inhibition of CTLA-4 Fc binding to Raji cells.

FIG. 24 is a graphical representation of the mean plasma concentration/time curve of the CTLA-4 binding mutein S140.4-O10 after single intravenous (open squares), intraperitoneal (filled triangles) or subcutaneous (filled squares) injection of 7.5 mg/kg mutein to mice in order to investigate bioavailability.

FIG. 25 shows a schematic drawing of phNGAL67. This vector codes for a fusion protein of the OmpA signal sequence, a modified hNGAL according to FIG. 1 (phNGAL35) with the exception of the three exchanges Arg81 to Ala, Lys125 to Ala and Lys134 to Ala, and an albumin-binding domain (ABD) of protein G from *Streptococcus* (Kraulis et al. (1996) *FEBS Lett.* 378, 190-194). The abd was fused to hNGAL by the original linker region from protein G and is C-terminally flanked by the Strep-Tag® II. A relevant segment of the nucleic acid sequence of phNGAL67 is reproduced together with the encoded amino acid sequence in the sequence listing as SEQ ID NO: 60. The segment begins with an XbaI restriction site and ends with the HindIII restriction site. The vector elements outside this region are identical with those of the vector pASK75, the complete nucleotide sequence of which is exhibited in the German patent publication DE 44 17 598 A1.

FIG. 26 shows a schematic drawing of phNGAL71. This vector codes for a fusion protein of the OmpA signal sequence, a modified hNGAL according to FIG. 1 (phNGAL35) and an CH4 domain of the Fc-portion of human IgE (Borsi, L. et al. (2002) *Int. J. Cancer* 102, 75-85). The CH4 domain was directly fused to the C-terminus of hNGAL and is C-terminally flanked by the Strep-Tag® II. A relevant segment of the nucleic acid sequence of phNGAL71 is reproduced together with the encoded amino acid sequence in the sequence listing as SEQ ID NO: 57. The segment begins with an XbaI restriction site and ends with the HindIII restriction site. The vector elements outside this region are identical with those of the vector pASK75, the complete nucleotide sequence of which is exhibited in the German patent publication DE 44 17 598 A1.

EXAMPLES

Example 1

Generation of a Library with about 10 Billion Independent hNGAL Muteins

Unless otherwise indicated, established recombinant genetic methods were used, for Example as described in Sambrook et al. Molecular Cloning: A Laboratory Manual (2d ed., Cold Spring Harbor Laboratory Press, Cold Spring Harbor, N.Y. (1989))

The library for hNGAL muteins was produced as described in Example 6 of International Patent application WO 03/029463. The entire disclosure of this PCT application is incorporated by reference herein in its entirety. The deviations in library-design are described in the following: The hNGAL-scaffold was modified by exchanging the following three amino acid residues Arg81, Lys125 and Lys134 against Ala, each. The resulting phagemid vector construct phNGAL35 (FIG. 1; SEQ ID NO: 5) was used as a template for PCR in order to prepare a random library of hNGAL with enhanced diversity. The Ala mutations at position Arg81 and Lys134 are also contained in the random-primers SEQ ID NO:1 (NGAL6+) and SEQ ID NO:2 (NGAL8*) used for concerted mutagenesis of in total 20 selected amino acid positions in the four peptide loops of hNGAL, with the exception that phNGAL35 was used as template in combination with these random primers.

Example 2

Phagemid Presentation and Selection of hNGAL Muteins Against Human CTLA-4-Fc Employing Polystyrol Multiwell Plates For the selection of hNGAL muteins the phagemid library from Example 1 was employed. The selection of hNGAL muteins was performed according to Example 3 of International Patent application WO 2005/019256. The deviations from the protocol are described in the following: Prior to the incubation with the target protein, phagemids from the library were incubated in bovine serum albumine-blocked polystyrol wells 2 times for 15 minutes for the depletion of phagemids representing multi-reactive or misfolded lipocalin mutein. The human CTLA-4-Fc (Chimerigen) consists of the extracellular domain of CTLA-4 fused to a hIgG1-Fc portion and was immobilized on the polystyrol plates with a concentration of 5 μg/ml in PBS via an anti-human IgG Fc Gamma fragment-specific antibody (Jackson ImmunoResearch, 209-005-098).

Five selection rounds against hCTLA-4 were carried out in this way employing the preparation of amplified phagemids from the respective previous enrichment cycle with the exception that only about $1 \cdot 10^{11}$ phagemids were utilized beginning with the second enrichment cycle. The phagemid amplification was performed as described in Example 2 of International Patent application WO 03/029463.

Example 3

Identification of hCTLA-4-Binding hNGAL Muteins by Use of a High-Throughput ELISA Screening Method For the analytical production of the hCTLA-4-binding hNGAL muteins equipped with an N-terminal T7 detection tag (Novagen) as well as a Strep-Tag® II affinity tag and their characterization by high-throughput ELISA screening, the gene cassette containing the hNGAL muteins between the two BstXI cleavage sites was subcloned from the vector phNGAL35 (FIG. 1) into the vector phNGAL37 (FIG. 2).

For this purpose the plasmid DNA was isolated from the mixture of the *E. coli* clones obtained by infection with the phagemids from Example 2 eluted as a result of the last selection cycle, using the Plasmid Miniprep kit (Qiagen). The DNA was cut with the restriction enzyme BstXI and the smaller of the two fragments (347 bp) was purified by preparative agarose-gel electrophoresis. The DNA of the vector phNGAL37 was likewise cut with BstXI and the larger of the two fragments (3431 bp) was isolated in the same way.

For the ligation, each 50 fmol of the two DNA-fragments were mixed with 3 Weiss Units T4 DNA ligase (Promega) in a total volume of 20 µl (30 mM Tris/HCl pH 7.8, 10 mM $MgCl_2$, 10 mM DTT, 1 mM ATP), followed by incubation overnight at 16° C. *E. coli* TG1-F⁻ (*E. coli* K12 TG1, which had lost its episome) was transformed with 5 µl of this ligation mixture according to the $CaCl_2$-method (Sambrook et al. Molecular Cloning: A Laboratory Manual (2d ed., Cold Spring Harbor Laboratory Press, Cold Spring Harbor, N.Y. (1989))) and plated on LB/Amp agar plates.

Single *E. coli* colonies obtained after the transformation harbouring the respective hNGAL plasmids coding for the hNGAL muteins were picked from these agar plates into 70 µl per well 2×YT/Amp in flat bottom 384 well plates (Greiner) by means of an automated colony picker (Genetix) and grown overnight at 37° C. at 700 rpm on a benchtop shaker (Bühler) in a humidified incubator (MMM Medcenter) at 60% relative humidity (rH). The cultures were diluted 1:100 into 100 µl 2×YT/Amp in round bottom 96 well plates (Nunc) by means of a 96 pin replicating head (Genetix) and grown for about 1 h at 37° C. and 60% rH, followed by an incubation for 3 h at 22° C. and 60% rH, both at 700 rpm, until the $OD_{550}$ reached approximately 0.6. The 384 well plates were kept as "master" plates at −80° C. after adding 25 µl 60% v/v glycerol to each well.

Recombinant hNGAL muteins were produced in the 96 well plates by adding 20 µl per well of 1.2 µg/ml anhydrotetracyclin in 2×YT (obtained by diluting a 2 mg/ml stock solution 1:1667 in 2×YT; final concentration 0.2 µg/ml) to the bacterial cultures and incubation overnight at 22° C. and 700 rpm at 60% rH. Afterwards, 40 µl of lysis buffer (400 mM Na-borate, pH 8.0, 320 mM NaCl, 4 mM EDTA, 0.3% w/v lysozyme) was added to each well and the plate was incubated for 1 h at 22° C. and 700 rpm at 60% rH. To minimize non-specific binding interactions in the subsequent ELISA experiment, obtained crude cell extracts were supplemented with 40 µl/well PBS containing 10% w/v BSA and 0.05% v/v Tween 20 (final concentration 2% w/v BSA) for 1 h at 22° C. and 700 rpm at 60% rH.

For the detection of binding, the crude cell extracts containing the hNGAL muteins were tested for their reactivity with the prescribed target human CTLA-4-Fc and the unrelated control proteins human serum albumine (HSA, Sigma) and hIgG-Fc specific antibody, respectively, in ELISA experiments. Therefore, wells of black Fluotrac 600 ELISA plates (Greiner; 384 well) were coated overnight with 20 µl of a solution of mouse monoclonal antibody specific for the Fc-portion of human IgG at a concentration of 5 µg/ml in PBS or the control protein at 4° C., 10 µg/ml in PBS. Plates were washed five times with 100 µl PBS containing 0.05% v/v Tween 20 (PBST/0.05) per well with an automated ELISA plate washer (Molecular Devices) leaving a residual volume of 10 µl of the washing buffer in each well after the last washing step. Residual binding sites were blocked by incubation with 100 µl PBST/0.05 containing 2% w/v BSA for 2 h at room temperature. Afterwards, plates were again washed five times as described above. Subsequently the complex between hIgG-Fc specific antibody from above and human CTLA-4-Fc was formed by incubating the plate with a solution of hCTLA-4-Fc in PBS at 5 µg/ml for 1 h at 25° C. Plates were again washed five times as described above.

For complex formation between the hNGAL muteins and the immobilized target, the wells were incubated with 10 µl of the cell extract from above for 1 hour at room temperature. Subsequently, plates were washed again five times and 10 µl of an anti-T7 monoclonal antibody-HRP-conjugate (Amersham), diluted 1:5000 in PBST/0.05 containing 0.5% w/v non-fat dry milk powder (Vitalia), was added to each well and incubated for 1 hour at room temperature. Plates were again washed five times and 10 µl of the fluorogenic HRP-substrate QuantaBlu™ (Pierce) was added to detect bound hNGAL muteins by means of the attached anti-T7 monoclonal antibody-HRP-conjugate. After 45 minutes at room temperature fluorescence was excited at a wavelength of 320 nm (±12.5 nm) and measured at 430 nm (±17.5 nm) in a GENiosPlus plate reader (Tecan).

From the fifth panning cycle a number of clones displaying significantly higher binding signals on hCTLA-4-Fc compared to the unrelated control proteins were derived. Subsequently twelve clones in total were subjected for DNA-sequencing according to standard procedures.

Finally five of the twelve sequenced clones showed unique sequences. Two of the five clones were further pursued and the nucleotide sequence of these clones was translated into the amino acid sequence. Those amino acids deviating from the modified hNGAL encoded by phNGAL35 (FIG. 1) are given in Table 1. The nucleotide sequences of these lipocalin muteins, named S67.2-F03 and S67.3-C21, are given as SEQ ID NO: 8, and SEQ ID NO: 9, respectively.

TABLE 1

Sequence characteristics of selected anti-hCTLA-4-Fc muteins

| Pos. | hNGAL | S67.2-F03 | S67.3-C21 |
|---|---|---|---|
| 40  | Ala | Arg | Tyr |
| 42  | Leu | Leu | Trp |
| 44  | Glu | Asp | Asn |
| 46  | Lys | Gln | Arg |
| 47  | Asp | His | Tyr |
| 49  | Gln | Met | Met |
| 50  | Lys | Asn | Gln* |
| 70  | Leu | Ile | Ile |
| 72  | Arg | Pro | Asp |
| 73  | Lys | His | Thr |
| 77  | Asp | Glu | Glu |
| 79  | Trp | Thr | Pro |
| 101 | Pro | Gly | Arg |
| 102 | Gly | Asp | Met |
| 103 | Leu | Lys | Asp |
| 125 | Ala | Leu | Gln |
| 127 | Ser | Glu | Asn |
| 128 | Gln | Asp | His |
| 130 | Arg | Ala | Thr |
| 132 | Tyr | Phe | His |

*This glutamine residue was encoded by an amber stop codon.

Example 4

Production of the hNGAL Muteins

For the preparative production of the muteins S67.2-F03 and S67.3-C21 described in Example 3, the *E. coli* K12 strain JM83 harbouring the expression vector phNGAL37 (FIG. 2, SEQ ID NO: 6) encoding this mutein was used for the periplasmatic production via shake flask expression in an appropriate culture volume of LB-Ampicillin medium according to the protocol described in Schlehuber et al. (2000) J Mol Biol. 297(5), 1105-1120.

When larger amounts of material were needed, the *E. coli* K12 strain W3110 harbouring the expression vector phNGAL37 encoding this mutein was used for the periplasmatic production via fermentor cultivation in a 0.75 l or 10 l bioreactor (Biostat B, B. Braun) based on the protocol described in Schiweck et al. (1995) Proteins: Struct. Funct. Genet. 23, 561-565. Fermentation was carried out at 25° C. The oxygen concentration was maintained at 30% saturation. In a 0.75 l bioreactor, oxygen saturation was kept at 30% via controlling the stirrer speed up to 1500 rpm. In a 10 l reactor, stirrer speed was kept at 480 rpm while supply of air and pure oxygen was regulated automatically. In fed batch phase 50% w/v Glucose was supplied stepwise starting with 17.5 ml/h up to 50 ml/h at OD=22.5.

The mutein was purified from the periplasmic fraction in a single step chromatographic protocol with Strep-Tactin Superflow (IBA) using a column of appropriate bed volume and suitable equipment according to the manufacturers' recommendations.

Gel filtration was carried out with Superdex 75 material (Amersham Pharmacia Biotech) using a column of appropriate bed volume and suitable equipment according to the manufacturers' recommendations. The monomeric fractions were pooled and used for the further characterizations steps.

Example 5

Generation of an Error-Prone-PCR Library for the Affinity Maturation of CTLA-4-Specific hNGAL Muteins In order to generate libraries for affinity-maturation of CTLA-4-specific HNGAL muteins the mutein S67.2-F03 obtained in Example 3 and the successor S94.7-Q13 (which was derived from affinity maturation of S67.2-F03), were each used as templates for an error-prone PCR approach, employing the nucleotide analogs 8-oxodGTP and dPTP (TEBU-Bio) according to the method described in literature (Zaccolo et al. (1996) J Mol Biol. 255(4), 589-603). For the amplification reaction the same pair of 5' biotinylated oligonucleotides SEQ ID NO: 3 (NGAL12bio) and SEQ ID NO: 4 (NGAL13bio) was used as for the original library generation described in Example 6 of International Patent application WO 03/029463 which allows, together with the nucleotide analogs, to introduce point mutations distributed randomly over the whole BstXI gene-cassette of the hNGAL mutein. The PCR product was purified using the Wizard SV Gel and PCR Clean-Up System (Promega) and for cloning purposes, the fragments representing either the affinity-matured library of S67.2-F03 or S94.7-Q13 muteins in nucleic acid form were first cut with the restriction enzyme BstXI (Promega) according to the instructions of the manufacturer and then purified as described above, resulting in a double stranded DNA-fragment of 347 nucleotides in size. DNA-fragments not or incompletely digested were removed via their 5'-biotin tags using streptavidin-coated paramagnetic beads (Merck) as described in Example 6 of International Patent application WO 03/029463.

For subsequent ligation of the affinity-matured muteins from above a 4631 fragment was prepared by BstXI restriction digest of the DNA of the vector phNGAL35 (FIG. 1). The ligation reaction and the transformation of electrocompetent E. coli XL1-Blue (Bullock et al.) was carried out according to the description in Example 6 of International Patent application WO 03/029463.

Example 6

Phagemid Presentation and Selection of CTLA-4-Specific Lipocalin Muteins Against CTLA-4-Fc Employing Protein A Magnetic Beads For the selection of affinity-matured CTLA-4-specific lipocalin muteins the error-prone phagemid library based on Q13 derived from Example 5 was used.

The selection of CTLA-4-specific lipocalin muteins employing protein A beads was essentially carried out as described in Example 27 in International Patent application WO 2005/019256 except the following deviations: The target concentration in solution was restricted to 2, 0.5 and 0.1 nM and the phagemids were incubated for 15, 5 and 1 min from round 1 to 3, respectively in order to select muteins with faster $k_{on}$ rates compared to Q13. The phagemids were eluted acidic and basic followed by a final bacterial elution step.

Three rounds of selection separately against hCTLA-4-Fc and mCTLA-4-Fc were carried out in this way employing the preparation of amplified phagemids from the respective previous enrichment cycle with the exception that only about $1 \cdot 10^{11}$ phagemids were utilized beginning with the second enrichment cycle.

Selection for affinity-matured CTLA-4-specific lipocalin muteins based on F03 was carried out according to the description above except that the target concentration was restricted to 100, 20 and 2 nM and the phagemids were incubated for 15 min from round 1 to 3, respectively in order to select muteins with faster $k_{on}$ rates compared to F03. Additionally the number of washing cycles was increased stepwise during the three selection rounds from 8 to 10 to 12, respectively. All clones were identified via HT-ELISA screening as described in Example 7 without J08 competition, except F92.1-J08. The latter mutein was derived from colony screening method as described in Example 8.

Example 7

Identification of Affinity-Matured hCTLA-4-Binding hNGAL Muteins by Use of a High-Throughput ELISA Screening Method For the detection of binding of the affinity-matured CTLA-4-specific hNGAL muteins, the crude cell extracts containing the hNGAL muteins were tested for their reactivity with the prescribed target protein hCTLA-4-Fc or mCTLA-4-Fc and the unrelated control proteins hB7-1 (R+D Systems), mCD28-Fc and hIgG, respectively, in ELISA experiments. Experiments were performed as described in Example 3 with the following deviations:

For complex formation between the CTLA-4-specific muteins and the target, 40 µl of the cell extract from above were incubated with either 1 pmol or 0.3 pmol hCTLA-4-Fc or 0.3 pmol mCTLA-4-Fc in solution for 1 hour at room temperature in a non-protein binding poly-propylene plate. In some cases purified CTLA-4-specific hNGAL muteins J08 without T7-tag was added at final concentrations of 30 nM or 120 nM in order to compete with the lipocalin mutein from the extracts for target-binding. Subsequently, the mixture of lipocalin mutein, target and competitor was transferred to the plates previously coated with hIgG-Fc specific antibody from Example 2 to capture the formed complexes via the Fc-portion of CTLA-4 and incubated for 1 h at room temperature. The screening of binders from the affinity-maturation of S67.2-F03 was performed similar to the description above.

A selection of muteins showed significantly higher binding signals on the prescribed target compared to the original mutein Q13. Subsequently, the identified muteins were subjected for sequence analysis according to standard procedures.

Example 8

Identification of Affinity-Improved CTLA-4-Specific hNGAL Muteins by Use of the Colony Screening Method For the analytical production of the hNGAL muteins as fusion proteins with the Strep-Tag® II and the albumin-binding domain (ABD) and their characterization by colony screening, the gene cassette between the two BstXI cleavage sites was subcloned from the phagemid vector phNGAL35 (SEQ ID NO: 5; FIG. 1) into phNGAL38 (SEQ ID NO:7; FIG. 3).

The automated colony screening assay was performed as described in International Patent application WO 2005/019256 which following deviations from that protocol: For complex formation between the CTLA-4-specific muteins immobilized on the filter via the ABD-domain, the hCTLA-4-Fc target was restricted to a either 10 nM, 1 nM or 0.1 nmol and the mCTLA-4-Fc to either 10 nM or 1 nM solution in PBS, while incubated with the filter. The hNGAL mutein J08 was identified by this method.

Example 9

Measurement of Affinity-Constants of the CTLA-4-Specific Lipocalin Muteins Using Surface-Plasmon-Resonance Spectroscopy (SPR)

14000 RU AffiniPure mouse anti-human IgG Fc Gamma fragment-specific antibody (Jackson ImmunoResearch, 209-005-098) was coupled by amine-coupling to a CM5 sensor chip (BIAcore). Subsequently 2000 RU hCTLA-4-Fc (Chimerigen) or mCTLA-4-Fc (R&D Systems) were captured to this surface by injecting 10 µl of a 0.15 mg/ml target solution at a flow rate of 2 µl/min. HBS buffer (10 mM HEPES, 150 mM NaCl, 2 mM EDTA, 0.005% Tween pH 7.4) was used as running buffer. All samples were diluted in this running buffer and binding of the lipocalin muteins to the captured target was measured by injection of a 40 µl sample of purified HNGAL muteins at different concentrations (5-0.3 µM) with a 20 µl/min flow rate. Due to the slow dissociation rate of the HNGAL muteins, the surface of the chip has to be regenerated using 10 mM HCl followed by recoupling of CTLA-4-Fc before the next lipocalin mutein concentration could be measured. All measurements were performed on a BIAcore X apparatus. The obtained binding curves were fitted using the BIAevaluation software 3.1 from BIAcore and resulted in affinity binding constants ($k_{on}$, $k_{off}$, $K_D$).

TABLE 2

Affinities of selected anti-hCTLA-4-Fc muteins

| hNGAL mutein | hCTLA-4-Fc | | | mCTLA-4-Fc | | |
|---|---|---|---|---|---|---|
| | $k_{on}$ [M$^{-1}$s$^{-1}$] | $k_{off}$ [s$^{-1}$] | $K_D$ [nM] | $k_{on}$ [M$^{-1}$s$^{-1}$] | $k_{off}$ [s$^{-1}$] | $K_D$ [nM] |
| S67.2-F03° (SEQ ID NO: 8) | 7.03E+03 | 3.3E−04 | 47.1 | 4.5E+03 | 8.9E−04 | 198 |
| S67.3-C21° (SEQ ID NO: 9) | 1.6E+04 | 3.3E−04 | 20 | 1.45E+04 | 0.098 | 6800 |
| F92.1-J08* (SEQ ID NO: 10) | 9.24E+03 | 1.16E−04 | 12.8 | 8.18E+03 | 2.98E−04 | 36.4 |
| S94.2-F05*(SEQ ID NO: 11) | — | — | 18 | — | — | 65 |
| S94.7-Q13*(SEQ ID NO: 12) | 6.0E+03 | 7.1E−05 | 11.8 | 4.3E+03 | 1.7E−04 | 39.5 |
| S106.3-O19* (SEQ ID NO: 13) | — | — | 22 | — | — | 135 |
| S107.4-C16* (SEQ ID NO: 14) | — | — | 28 | — | — | 275 |
| S106.3-K20* (SEQ ID NO: 15) | — | — | 29 | — | — | 300 |
| S106.1-N15* (SEQ ID NO: 16) | — | — | 43 | — | — | 110 |
| S109.6-J11" (SEQ ID NO: 17) | — | — | 20 | — | — | 47 |
| S109.4-A15" (SEQ ID NO: 18) | — | — | 26 | — | — | >500 |

TABLE 2-continued

Affinities of selected anti-hCTLA-4-Fc muteins

| | hCTLA-4-Fc | | | mCTLA-4-Fc | | |
|---|---|---|---|---|---|---|
| hNGAL mutein | $k_{on}$ [M$^{-1}$s$^{-1}$] | $k_{off}$ [s$^{-1}$] | $K_D$ [nM] | $k_{on}$ [M$^{-1}$s$^{-1}$] | $k_{off}$ [s$^{-1}$] | $K_D$ [nM] |
| S109.5-L04" (SEQ ID NO: 19) | — | — | 29 | — | — | 42 |
| S109.5-L23" (SEQ ID NO: 20) | — | — | >500 | — | — | 19 |

Sequence IDs are given in brackets, following the mutein name
°Clones derived from original selection with hNGAL library as described in Example 2 were selected by HT-ELISA screening (see Example 3).
*Clones derived from affinity-maturation of S67.2-F03. For the selection of affinity-matured CTLA-4-specific HNGAL muteins an error-prone phagemid library based on F03 was used (description of library preparation see Example 5). Selection was carried out as described in Example 6 with the exception that the target concentration was restricted to 100, 20 and 2 nM and the phagemids were incubated for 15 min from round 1 to 3, respectively in order to select muteins with faster $k_{on}$ rates compared to F03. In addition, the number of washing cycles was increased stepwise during the three selection rounds from 8 to 10 to 12, respectively. The affinity-matured CTLA-4-specific lipocalin muteins were identified via HT-ELISA screening as described in Example 7 without the competition with purified J08. The clones S106 and S107 were derived from a rescreening of the clones S94 under competing conditions with soluble J08 (see Example 7).
F92.1-J08 is an affinity-matured successor of F03, which was derived from colony screening method as described in Example 8.

"Clones derived from affinity-maturation of S94.7-Q13 (see Example 5 and 6).

Example 10

Phagemid Presentation and Selection of Stability-Matured CTLA-4-Specific Lipocalin Muteins Employing Protein A Magnetic Beads For the selection of stability-matured CTLA-4-specific lipocalin muteins an error-prone phagemid library based on J08 was used, which was constructed as described in Example 5 with the exception that F92.1-F08 was used as a template for error-prone PCR.

The selection of CTLA-4-specific lipocalin muteins employing protein A beads was performed in accordance with Example 27 in International Patent application WO 2005/019256. The target concentration was restricted to 50 nM and the phagemids were heated to 40, 50, 60 or 70° C., respectively in order to select muteins with improved thermal stability compared to J08. The phagemids were eluted by an acidic elution step.

Three rounds of selection against hCTLA-4-Fc were carried out in this way employing the preparation of amplified phagemids from the respective previous enrichment cycle with the exception that only about 1·10$^{11}$ phagemids were utilized beginning with the second enrichment cycle.

Example 11

Identification of Stability-Matured hCTLA-4-Binding hNGAL Muteins by Use of a High-Throughput ELISA Screening Method The CTLA-4-specific lipocalin muteins were screened as described in Example 7 with deviations in the protocol as follows: Prior to complex formation between the CTLA-4-specific muteins and the target a part of the prepared mutein cell-extract was heated to 60° C. for 1 h, as the other part of the extract was incubated at RT. The binding signals on hCTLA-4-Fc of these extracts were compared to those of J08. Simultaneously the cross-reactivity of the muteins was checked on mCTLA-4-Fc using identical conditions but without heating the extracts. In order to screen for higher affinity, 20 nM soluble B7.1-Fc receptor (R+D systems) was added to the mutein extracts as a competitor for binding to hCTLA-4-Fc, which in this case was directly immobilized on the polystyrol plate at a concentration of 5 µg/ml in PBS.

8 hNGAL muteins with the highest binding signals on hCTLA-4-Fc after heating of extracts to 60° C. compared to J08 were selected for sequence analysis according to standard procedures.

Eight unique sequences of the sequenced clones carried a functional insert. The nucleotide sequences of the clones were translated into the amino acid sequence (SEQ ID NO: 23, SEQ ID NO: 24, SEQ ID NO: 25, SEQ ID NO: 26, SEQ ID NO: 27, SEQ ID NO: 28, SEQ ID NO: 22, SEQ ID NO: 21) and those amino acids deviating from the modified hNGAL mutein J08 (SEQ ID NO: 10) are given in Table 3. All eight clones were chosen for the determination of binding affinity for human and murine CTLA-4-Fc using the SPR-spectroscopy method as described in Example 9. The thermal stability of the muteins was measured via CD-spectroscopy as described in Example 13.

TABLE 3

Sequence characteristics of stability-matured CTLA-4-specific hNGAL muteins

| Mutein | Pos. 50 | Pos. 55 | Pos. 71 | Pos. 72 | Pos. 80 | Pos. 88 | Pos. 95 | Pos. 96 | Pos. 114 | Pos. 116 | Pos. 129 |
|---|---|---|---|---|---|---|---|---|---|---|---|
| F92.1-J08 | Asn | Ile | Phe | Pro | Ile | Gln | Gly | Asn | Asn | Asn | Asn |
| S140.1-F09 | Asn | Ile | Ser | Ser | Ile | Gln | Gly | Asn | Asn | Asn | Asn |

TABLE 3-continued

Sequence characteristics of stability-matured CTLA-4-specific hNGAL muteins

| Mutein | Pos. 50 | Pos. 55 | Pos. 71 | Pos. 72 | Pos. 80 | Pos. 88 | Pos. 95 | Pos. 96 | Pos. 114 | Pos. 116 | Pos. 129 |
|---|---|---|---|---|---|---|---|---|---|---|---|
| S140.1-D24 | Asn | Ile | Phe | Ser | Ile | Arg | Gly | Asn | Asn | Asn | Asn |
| S140.2-P24 | Asp | Ile | Ser | Ser | Ile | Gln | Gly | Asn | Asp | Ser | Asn |
| S140.2-H04 | Asn | Ile | Phe | Ser | Ile | Gln | Gly | Asn | Asn | Asn | Asn |
| S140.3-A23 | Asn | Val | Ser | Ser | Val | Gln | Gly | Asn | Asn | Asn | Asn |
| S140.3-P07 | Asn | Ile | Phe | Pro | Ile | Gln | Gly | Asn | Asp | Asn | Asp |
| S140.4-B16 | Asn | Ile | Phe | Pro | Ile | Gln | Ser | Asp | Asp | Asn | Asn |
| S140.4-O10 | Asn | Ile | Ser | Ser | Ile | Gln | Gly | Asn | Asp | Asn | Asn |

Amino acid substitution in bold letters arose from error-prone PCR comprising the complete BstXI-gene cassette

TABLE 4

Sequence characteristics of selected anti-hCTLA-4-Fc muteins

| Pos. | hNGAL | F92.1-J08 | S140.4-O10 |
|---|---|---|---|
| 40 | Ala | Arg | Arg |
| 44 | Glu | Asp | Asp |
| 46 | Lys | Gln | Gln |
| 47 | Asp | His | His |
| 49 | Gln | Met | Met |
| 50 | Lys | Asn | Asn |
| 70 | Leu | Ile | Ile |
| 71 | Phe | Phe | Ser |
| 72 | Arg | Pro | Ser |
| 73 | Lys | His | His |
| 77 | Asp | Glu | Glu |
| 79 | Trp | Thr | Thr |
| 101 | Pro | Gly | Gly |
| 102 | Gly | Asp | Asp |
| 103 | Leu | Lys | Lys |
| 114 | Asn | Asn | Asp |
| 118 | His | Tyr | Tyr |
| 120 | Met | Val | Val |
| 125 | Ala | Leu | Leu |
| 126 | Val | Ala | Ala |
| 127 | Ser | Glu | Glu |
| 128 | Gln | Asp | Asp |
| 130 | Arg | Ala | Ala |
| 132 | Tyr | Phe | Phe |

Example 12

Production of the hNGAL Muteins

The eight muteins were produced in a shakerflask expression as described in Example 4.

Example 13

Measurement of Affinity-Constants of Stability-Matured CTLA-4-Specific hNGAL Muteins Using BIAcore The selected muteins from stability-maturation including S140.4-O10 without T7 tag (SEQ ID NO: 56) were tested in terms of affinity for h/m CTLA-4-Fc using SPR-spectroscopy as described in Example 9. The affinities for human and mouse CTLA-4-Fc are summarized in Table 5.

TABLE 5

Affinities of stability-matured CTLA-4-specific hNGAL muteins

| hNGAL mutein | hCTLA-4-Fc | | | mCTLA-4-Fc | | |
|---|---|---|---|---|---|---|
| | $k_{on}$ [$M^{-1}s^{-1}$] | $k_{off}$ [$s^{-1}$] | $K_D$ [nM] | $k_{on}$ [$M^{-1}s^{-1}$] | $k_{off}$ [$s^{-1}$] | $K_D$ [nM] |
| S140.1-D24 | 2.1E+04 | 1.26E−04 | 6 | 1.4E+04 | 2.66E−04 | 19 |
| S140.1-F09 | 1.18E+04 | 4.26E−04 | 7.8 | 1.40E+04 | 3.79E−04 | 27.9 |
| S140.4-O10 | 1.53E+04 | 2.21E−04 | 8.3 | 1.19E+04 | 4.90E−04 | 40.8 |
| S140.4-O10 (−T7 tag) | 2.77E+04 | 1.08E−04 | 3.9 | 2.72E+04 | 4.16E−04 | 15.3 |
| S140.3-A23 | 1.8E+04 | 3.42E−04 | 19 | 1.4E+04 | 8.96E−04 | 64 |
| S140.2-P24 | 1.4E+04 | 2.8E−04 | 20 | 1.5E+04 | 7.05E−04 | 47 |
| S140.2-H04 | 1.5E+04 | 3.45E−04 | 23 | 1.16E+04 | 5.1E−04 | 44 |
| F92.1-J08 | 9.24E+03 | 1.16E−04 | 12.8 | 8.18E+03 | 2.98E−04 | 36.4 |
| S140.3-P07 | 1.1E+04 | 3.19E−04 | 29 | 6.8E+03 | 6.66E−04 | 98 |
| S140.4-B16 | 6.16E+03 | 4.18E−04 | 68 | 5E+03 | 5.6E−04 | 112 |

Example 14

Determination of Thermal Denaturation for CTLA-4-Specific hNGAL Muteins by Use of CD Spectroscopy Circular dichroism spectra of the purified CTLA-4-specific hNGAL muteins from stability-maturation as described in Example 11 were measured with a Jasco-810 spectropolarimeter (Jasco, Groβ-Umstadt, Germany) thermostatted with a computer controlled waterbath. Solutions of the lipocalin muteins were concentrated at 100-200 μg/ml in PBS buffer, pH 7.5 and applied in a quartz cuvette with a pathlength of 1 mm that was sealed with a Teflon lid. Thermal unfolding was performed by heating the sample at a constant temperature gradient of 40 k h-1 from 25 to 95° C. Data were collected for each 0.1 K step at a wavelength of 218 nm, where maximal spectral change upon unfolding was observed for hNGAL muteins beforehand. The sample buffer showed no change in ellipticity with variation in temperature, so no corrections were made. Data from the thermal denaturation experiments were fitted by non-linear least-square regression using Kaleidagraph software and an equation for a two-state model of the unfolding transition as described at Brumano et al. (2000) Arch Biochem Biophys. 382(1), 57-62 and Cohen et al. (1994) Protein Sci. 3(8), 1253-60. Using the parameters from the corresponding curve fit, the unfolded fraction f(u) was plotted as a function of temperature T for illustration (see FIG. 4) and the values for the melting temperature is given in Table 6 together with the corresponding $K_D$-values for each mutein.

TABLE 6

Tm of stability-matured CTLA-4-specific hNGAL muteins

| Lipocalin mutein | Tm [° C.] | KD [nM] vs hCTLA-4 | KD [nM] vs mCTLA-4 |
|---|---|---|---|
| F92.1-J08 | 48.3 | 12.8 | 34.4 |
| S140.1-F09 | 60.1 | 7.8 | 27.9 |
| S140.1-D24 | 60.2 | 6 | 19 |
| S140.4-B16 | 57.6 | 68 | 112 |
| S140.2-H04 | 64.0 | 23 | 44 |
| S140.3-P07 | 56.8 | 29 | 98 |
| S140.3-A23 | 59.6 | 19 | 64 |
| S140.2-P24 | 65.3 | 20 | 47 |
| S140.4-O10 | 65.5 | 8.3 | 40.8 |

As can be seen from these melting temperatures and the comparison of the amino acid sequence, the mutein F09 which has the same amino acid sequence as the mutein J08 except the presence of a Ser residue at position 71 and 72 has substantially the same affinity to murine and human CTLA-4 but a melting temperature that is by more than 10° C. higher than the one of J08. The mutein O10 which has the same amino acid sequence as the mutein F09 expect the presence of an Asp residue at position 114 and 72 also has substantially the same affinity to murine and human CTLA-4 but a melting temperature that is even 5° C. higher than the one of F09. Accordingly, this data shows that the presence of a negatively charged amino acid such as an Asp at sequence position 114 and the presence of Ser residues at positions 71 and or 72 of hNGAL leads to a significant increase in the folding stability of the CTLA-binding muteins at unchanged binding properties.

Example 15

Stability Test of S140.4-O10

Stability of CTLA-4 binding hNGAL mutein S140.4-O10 at 37° C. was tested under various conditions. The tests with this lipocalin mutein were carried out at concentrations of 10 mg/ml and 0.5 mg/ml in PBS, pH 7.4 and also in human respectively murine plasma at 0.5 mg/ml each. Samples were stored at 37° C. for 1 hour, 1, 4 and 7 days. Reference standards were frozen at −20° C. Additionally, osmotic pumps (Alzet, Model 2001) with a pumprate of 1 μl/h over seven days as application system for lipocalin muteins in animal studies were investigated. Pumps were used according to manufacturer's recommendations. The mutein S140.4-O10 was applied at a concentration of 10 mg/ml to the pumps, which were placed in 7 ml PBS. The mutein was analyzed subsequently from surrounding PBS. Pumps were incubated at 37° C. for 1, 2, 3, 4 and 7 days. PBS samples were analyzed by SDS-PAGE, Westernblot, HPLC-SEC and Affinity-ELISA (using hCTLA-4 Fc as capture reagent and a T7 tag specific antibody for detection). Samples incubated in murine respectively human plasma and samples from osmotic pumps were analyzed by Affinity-ELISA.

No aggregation or degradation of the mutein S140.4-O10 could be detected during seven day incubation in PBS at 0.5 mg/ml at 37° C. Even at 10 mg/ml>98%, judged by HPLC-SEC (see FIG. 5), of the material remained monomeric. The measured affinities of all samples incubated in PBS at 37° C. were within a range of +/−25% compared to the reference standard (table 6). Affinities of all samples in human plasma were within a range of +/−25% compared to the reference standard (Table 7) as well. Incubation of the lipocalin mutein in mouse plasma resulted in a drop of affinity after 7 days to approximately 50% compared to reference. Affinities from osmotic pumps samples were within a range of +/−25% to the reference standard (Table 7). One time point (1 day, 164% compared to reference standard) was outside the range.

TABLE 7

Affinities of mutein S140.4-O10 to human CTLA-4 incubated under various conditions determined by ELISA

| Time | 10 mg/ml in PBS | 0.5 mg/ml in PBS | 0.5 mg/ml in mouse plasma | 0.5 mg/ml in human plasma | 10 mg/ml in PBS (osmotic pumps) |
|---|---|---|---|---|---|
| 0 h | 26 (100) | 34 (100) | 49 (100) | 32 (100) (100*) | 41 (100) |
| 1 h | 25 (104) | 33 (103) | 42 (117) | 35 (91) (97.5*) | 25 (164) |

TABLE 7-continued

Affinities of mutein S140.4-O10 to human CTLA-4 incubated under various conditions determined by ELISA

| Time | 10 mg/ml in PBS | 0.5 mg/ml in PBS | 0.5 mg/ml in mouse plasma | 0.5 mg/ml in human plasma | 10 mg/ml in PBS (osmotic pumps) |
|---|---|---|---|---|---|
| 1 day | 31 (84) | 34 (100) | 56 (88) | 36 (89) (96.1*) | 47 (87) |
| 4 days | 31 (84) | 38 (89) | 48 (102) | 32 (100) (91.2*) | 42 (98) |
| 7 days | 34 (76) | 41 (83) | 91 (54) | 41 (78) (102.8*) | 36 (114) |

*Values were determined from a quantitative ELISA, where O10 was functionally captured via mCTLA-4-Fc and detected with an anti-hNGAL antibody.
Table 7. Affinities of mutein S140.4_O10 to human CTLA-4 were determined by Affinity-ELISA after incubation under various conditions and for the time periods indicated in the table. The calculated percentage of the experimental samples affinity compared to reference standard is indicated in brackets.

Example 16

FACS Binding Studies with CHO Cell Lines Expressing Human, Mouse or Cynomolgus CTLA-4

The full length cDNAs coding for human, murine and simian CTLA-4 were cloned by RT-PCR using standard procedures (Sambrook et al. Molecular Cloning: A Laboratory Manual (2d ed., Cold Spring Harbor Laboratory Press, Cold Spring Harbor, N.Y. (1989))). RNA was prepared from human PBMC, murine spleen cells or cynomolgous monkey (*macaca fascicularis*) PBMC that were activated in vitro for two days with plate bound anti-CD3 (anti-human CD3, clone OKT3 for human and cynomolgous cells, and anti-mouse CD3 clone CL001A, Acris for murine cells at 10 µg/ml) and soluble anti-CD28 (anti-human CD28, clone B-T3, Acris for human and cynomolgous and anti-mouse CD28, clone 37.51.1, Acris at 5 µg/ml) antibody preparations. The following primers were used to amplify the CTLA-4 cDNA from different species.

```
human and cynomolgous monkey:
hCTLA-4-fwd: C T A C T T C C T G A A G A C C T G A A C A C C  (SEQ ID NO: 75)

hCTLA-4-rev: G T T A G A A T T G C C T C A G C T C T T G G    (SEQ ID NO: 76)

mouse:
mCTLA-4-fwd: G G T T T T A C T C T G C T C C C T G A G G A C  (SEQ ID NO: 77)

mCTLA-4-rev: G C T T T T A G A G A C T G A A G T A T G C T C  (SEQ ID NO: 78)
```

PCR products of the corresponding length were isolated by agarose gel electrophoresis, purified and ligated into the cloning vector pCRBluntII-TOPO (Invitrogen) according to the manufacturer's recommendations and sequenced to identify clones with the correct sequence. CTLA-4 cDNAs were excised from the vector by XhoI/HindIII restriction digestion and isolated by agarose gel electrophoresis as described in Sambrook et al. Molecular Cloning: A Laboratory Manual (2d ed., Cold Spring Harbor Laboratory Press, Cold Spring Harbor, N.Y. (1989)). The fragment was purified and ligated into the expression vector pcDNA3.1Zeo(+) (Invitrogen) which had been linearized with the same restriction enzymes. XL1-Blue bacteria were transformed with the expression constructs and the DNA was extracted and purified using the ET-free Maxiprep Kit (Qiagen). 400.000 CHO-K1 cells (DSMZ no. ACC 110) were plated in 3.5 cm plates and transfected the following day using 4 µg plasmid DNA and 10 µl LipofectAMINE2000 (Invitrogen) according to the manufacturer's recommendations. Cells were either transfected with pcDNA-human-CTLA-4, pcDNA-murine-CTLA-4, pcDNA-cynomologous-CTLA-4 or the empty vector pcDNA3.1Zeo(+). One day later, the cells were trypsinized and transferred into five 9.5 cm plates. Selection started by addition of 200 µg zeocin/ml medium the following day. After a week, zeocin resistant clones were picked, transferred into 24 well plates and expanded in zeocin containing media for FACS analysis. High levels of CTLA-4 cell surface expression were detected with CTLA-4-specific monoclonal antibody 8H5 (Ancell) for human, 4F10 (UC10-4F10-11, ATCC #HB-304) for mouse and BNI3 (BD Biosciences) for cynomolgus monkey. Clones exhibiting the highest expression were kept, stocks were frozen and all further assays were performed with these cell lines up to passage number 30. In analogy, clones of A431 cells (DSMZ, no. ACC 91) stably transfected with human CTLA-4 were generated using the pcDNA-human-CTLA-4 expression vector and approach as described above.

The 4F10 monoclonal antibody was purified from the cell culture supernatant of the hybridoma UC10-4F10-11, ATCC #HB-304 by protein-G affinity chromatography as recommended by the supplier (Amersham Pharmacia). Antibody was eluted with 0.1 M glycine pH 2.7 and the collected fractions were neutralized instantaneously with 1 ml of Tris-HCl pH 9.0. Pooled fractions were dialysed with a 10 kDa cutoff membrane against PBS and sterile filtered over a 0.2 uM membrane filter.

FACS binding studies were performed with the transfected CHO cells to assess binding of the lipocalin mutein to the target in its native conformation on the cell surface. For this purpose, approximately 200.000 transfected CHO cells were resuspended in 30 µl PBS-2% v/v FCS and incubated with 2.5 µg of lipocalin muteins or 1 µg control antibodies for 30-45 minutes on ice. Bound lipocalin muteins were detected using a biotinylated hNGAL specific monoclonal antibody (HYB211-2-bio, Antibodyshop) and streptavidin-phycoerythrin (Sigma) whereas bound antibodies were detected with an isotype specific antibody conjugated with phycoerythrin. Vector control transfected CHO cells were stained in parallel and isotype reagents (hNGALwt and IgG preparations) were used to demonstrate specificity of the lipocalin mutein and antibody staining. The identified hNGAL muteins S67.2-F03, F92.1-J08, S94.7-Q13 and S140.4_O10 bound specifically to native human CTLA-4 expressed on the cell surface of transfected CHO cells but not vector control transfected CHO cells. The results were furthermore confirmed on human CTLA-4 transfected A431 cells. Cross-reactivity with native murine and cynomolgous CTLA-4 expressed on the cell surface of transfected CHO cells could be demonstrated and exemplary results of a FACS experiment are shown in FIG. 6. Target specific binding of half-life extended versions of hNGAL muteins namely S140.4-O10-ABD, site-directed PEGylated form of S140.4-O10 (12 kD, 20 kD, 30 kD PEG), S140.4-O10-CH4 and S140.4-O10-Fc was also demonstrated in FACS experiments with hCTLA-4 transfected CHO cells.

Example 17

CTLA-4-Fc FACS Competition Studies with Human B7 Expressing Cell Lines

FACS competition studies measuring the inhibition of human or mouse CTLA-4 Fc (Chimerigen) binding to different human B7.1 and/or B7.2 expressing cell lines were used to assess the efficacy of different CTLA-4 specific lipocalin muteins and monoclonal antibodies. Initially, P815 cells transfected with human CD86 and later human B7.1 and B7.2 expressing JY human B lymphoblastoid cell line and Raji (DSMZ, ACC 319) cells were used. Lipocalin muteins or monoclonal antibodies 4F10 (purified from hybridoma UC10-4F10-11, ATCC #HB-304 as described in example 16), 9H10 (Acris), 14D3 (eBioscience) or BNI3 (Becton Dickinson) were pre-incubated with human or murine CTLA-4 Fc (Chimerigen) in FACS buffer (PBS, 2% BSA) for 30-60 minutes at room temperature before the addition to $1-2\times10^5$ cells washed cells to allow the lipocalin muteins or antibodies to bind to CTLA-4 Fc. Human and murine CTLA-4 Fc were initially used at 55 and 50 nM respectively and subsequently at a 2.5 nM concentration. Lipocalin mutein/antibody pre-incubated human or mouse CTLA-4 Fc was incubated for 30 minutes at 4° C. with B7 expressing cells, washed with FACS buffer and incubated with PE-labeled goat anti-human or goat anti-mouse IgG-PE (F(ab)2 fraction, Jackson) for 30 minutes at 4° C. Cells were analyzed in a FACScan or FACSCalibur (Becton Dickinson) using CellQuest software. Typically, 10.000 events were recorded, a gate was set around the viable cells, and results are expressed as geometric mean of the fluorescence intensity (MFI).

A dose dependent inhibition of human CTLA-4 Fc binding to B7.2 transfected cells by the lipocalin muteins S67.2-F03 and S94.7-Q13 could be observed and was compared to antibody controls (14D3 human CTLA-4 specific, 4F10 mouse CTLA-4 specific) at equal concentrations (FIG. 7 A). S94.7-Q13 but not S67.2-F03 also inhibited mouse CTLA-4 Fc binding in this assay. Comparable inhibition of human and mouse CTLA-4 Fc binding to B7.2 transfected cells by hNGAL mutein S94.7-Q13 and F92.1-J08 could be demonstrated in a subsequent study (FIG. 7 B). Lower concentrations of lipocalin mutein were required to inhibit human CTLA-4 Fc binding compared to mouse CTLA-4 Fc (FIG. 7 B). Comparable results were obtained when the experiments were performed with B7.1 and B7.2 expressing JY cells.

In subsequent experiments human and mouse CTLA-4 Fc were used at 2.5 nM that was sufficient to obtain maximal FACS staining with B7.1 and B7.2 expressing Raji cells. A titration of equimolar amounts of lipocalin mutein S140.4-O10 (22 kD) and monoclonal antibodies (150 kD) were used to assess IC50 values (FIG. 8 and Table 8). IC50 values were calculated using a sigmoidal dose response model with the program Prism (GraphPad). Similar IC 50 values were obtained with the half-life extended versions of hNGAL muteins namely S140.4-O10-ABD and the site-directed PEGylated forms of S140.4-O10 (20 kD, 30 kD PEG) in this assay (FIG. 23). A control lipocalin hNGAL-58 or isotype matched antibody controls did not influence human or mouse CTLA-4 Fc binding to Raji cells.

TABLE 8

| Lipocalin mutein/antibody Fc | IC 50 [nM] with hCTLA-4 Fc | IC 50 [nM] with mCTLA-4 |
|---|---|---|
| mAb 14D3 | 1.9 | n.a. |
| mAb BNI3 | 2.1 | n.a. |
| S140.4-O10(-T7) | 2.5 | 15.5 |
| mAb 4F10 | n.a. | 4.1 |

Example 18

Lipocalin Muteins Reverse Human and Mouse CTLA-4 Fc Inhibition of CD86 Costimulation-Dependent Activation of T Cells by Anti-CD3+P815-B7.2 Cells Costimulation-dependent T cell activation can be completely inhibited in vitro by the addition of human or mouse CTLA-4 Fc to an appropriate cell culture assay. Reversal of this inhibition by lipocalin muteins or monoclonal antibodies was used as a functional in vitro assay to assess the efficacy of lipocalin muteins. INFγ secretion was used to measure human T cell activation induced with anti-CD3 and B7.2 transfected P815 cells in the presence and absence of CTLA-4 Fc.

Peripheral blood mononuclear cells (PBMC) were isolated from a buffy coat by density centrifugation on lymphoprep (Nycomed), followed by three washes. T cells were isolated from the PBMC by using lymfokwik-T (One Lambda Inc, Canoga Park, Calif.) as indicated by the supplier. T cells ($10^5$ T cells/well) were co-cultured with $10^4$ murine FcγRI expressing P815 cells transfected human CD86 in IMDM (BioWhittaker), 10% Fetal calf serum, and 80 µg/ml gentamycin. The cells were cultured at 37° C., 5% CO2 in a humidified atmosphere (95% relative humidity). To these cultures 1 µg/ml of the anti-CD3 monoclonal antibody UCHT-1 was added. After a 48 hours period (and in some experiments also a 120 hour incubation period), supernatants were removed to measure the production of IFN-g (Cytoset human IFN-g Biosource International) according to the instructions of the manufacturer.

All three hNGAL muteins S67.2-F03, S94.7-Q13 and F92.1-J08 completely reverse inhibition of human T cell stimulation by human CTLA-4-Fc in a concentration dependent manner. Control co-stimulation experiments excluded a stimulatory effect of preparations of the lipocalin muteins in the absence of anti-CD3 stimulation or an inhibitory effect in the absence of CTLA-4-Ig. Efficacy correlates with affinities as F92.1-J08 works slightly better than S94.7-Q13 and S67.2-F03. Furthermore, S94.7-Q13 and F92.1-J08 also completely reverse inhibition of T cell stimulation by mouse CTLA-4 Fc in this assay (see FIG. 9).

Example 19

Lipocalin Muteins Reverse Human and Mouse CTLA-4 Fc Inhibition of Costimulation-Dependent Activation of T Cells by Protein Antigens The effect of CTLA-4-Ig and lipocalin muteins on antigen-specific T-cell proliferation against antigens such as tetanus toxoid (RIVM, Bilthoven, The Netherlands) or *candida albicans* (ARTU, Lelystad, The Netherlands) was studied. To this aim, peripheral blood mononuclear cells (PBMC) were isolated from a buffy coat by density centrifugation on lymphoprep (1.077 g/ml, Nycomed, Torstov, Norway), followed by three washes. The cells were suspended in IMDM, 5% normal human serum (NHS, Bio-Whittaker), and gentamycin as antibiotic. $2 \times 10^5$ PBMC were added per well to a 96 well round bottom tissue culture plate. To these wells was added tetantus toxoid (TT, final dilution 0.75 Lf/ml or *candida albicans* (CA, 5 µg/ml). To these cultures CTLA-4 Fc and/or lipocalin muteins were added at the start of the culture. Plates were cultured for 6 days, at the end of which 50 µl supernatant was removed to measure IFN-γ and proliferation was measured by $^3$H-thymidine incorporation.

In vitro efficacy of CTLA-4 binding hNGAL muteins has been demonstrated using antigen (*Candida albicans* and tetanus toxoid) specific proliferation of human peripheral blood T cells in the presence and absence of CTLA-4 Fc. Addition of 5 µg/ml CTLA-4 Fc protein at the start of the culture inhibits T cell co-stimulation and thereby proliferation. Pre-incubation of CTLA-4 Fc with anti-CTLA-4 monoclonal antibodies or CTLA-4 binding lipocalin muteins reverse the inhibitory effect of CTLA-4 Fc in a dose dependent manner. Similar potency of F92.1-J08 and S94.7-Q13 were demonstrated in side by side comparison against human and mouse CTLA-4 Fc (data shown for F92.1-J08). F92.1-J08 appears to reverse the inhibitory effect of mouse CTLA-4 Fc similar to the 9H10 control antibody as demonstrated with two different antigens in the T cell activation assay. The reversing activity towards human CTLA-4 was about 4 times more efficient compared to mouse CTLA-4 which is consistent with the lower affinities of F92.1-J08 for mouse CTLA-4 (see FIG. 12*a*). Dose dependent reversal of human and mouse CTLA-4 Fc inhibition of *Candida albicans* and tetanus toxoid induced T cell proliferation was demonstrated for the affinity matured lipocalin mutein S140.4-O10 as well (see FIG. 12 *b*). Two independent production batches of the lipocalin mutein were tested on PBMC isolated from two different donors with comparable results.

Example 20

Extension of Serum Half Life of CTLA-4-Specific Lipocalin Muteins and Determination of Affinities Towards hCTLA-4

In order to increase the in vivo half-life, lipocalin muteins were exemplarily modified by the following procedures.

The hNGAL mutein F92.1-J08 was PEGylated with linear 20 kDa-mPEG-NHS ester leading to a randomly PEGylated protein with modified lysine side chains. The protein was treated for 1 hour at room temperature with an equimolar ratio of PEGylating agent in PBS at pH7.5 (yield 40-50%).

In the case of site-directed PEGylation the hNGAL mutein S140.4-O10 comprising a free cystein residue at amino acid position 87 (SEQ ID NO: 61) was used for PEGylation with linear 12 K, 20 k or 30 k PEG-maleimide. To this aim, the Serin at position 87 was back-mutated to a Cystein like originally occurs in hNGAL wildtype by site-directed mutagenesis (Quick-change mutagenesis Kit, Stratagene). Prior to the PEGylation reaction the free cystein residue was reduced using 250 µM TCEP for 3 h at RT. Before the PEGylation step the TCEP has to be removed completely from the reaction mixture by dialysis against 20 mM NaPhosphate buffer pH 7.0 with 150 mM NaCl. PEGylation was performed by mixing the protein with 2.5 molar excess of PEG-maleimide reagent for 4-6 h at 4° C. The reaction was stopped by adding 10 µM of Thioethanol.

An ABD-fusion protein was constructed with the mutein S94.7-Q13 as described in Example 8 (SEQ ID NO: 29). The mutein S140.4-O10 was also fused to the albumin binding domain but in contrast to S94.7-Q13-ABD the original linker derived from streptococcal protein G was located between the hNGAL mutein and ABD (SEQ ID NO: 59). In order to extend serum half life by dimerization S140.4-O10 was genetically fused to the CH4 domain of the human IgE-Fc portion. Therefore the CH4 domain was cloned between the hNGAL mutein and the C-terminal strep-affinity tag (SEQ ID NO: 58).

The half-life extended versions of hNGAL muteins were produced as described in Example 4 using an additional Q-Sepharose chromatography step in order to remove bacterial endotoxins. Pharmacokinetic studies in the mouse were performed with the F92.1-J08-PEG (20 k), S94.7-Q13-ABD, S140.4-O10-ABD, the site-directly PEGylated O10 (20 k, 30 k PEGs) and the S140.4-O10-CH4 as described in Example 21. Affinities of different half-life extended formats of the hNGAL mutein S140-O10 towards hCTLA-4-Fc were determined by SPR-spectroscopy and ELISA as described in Example 9 and are summarized in Table 10 in comparison to the naked hNGAL mutein S140.4-O10.

TABLE 10

| format of lipocalin mutein | SPR-Affinity [nM] | ELISA affinities [nM] |
|---|---|---|
| O10 | 3.7 | 3.8 |
| O10-ABD | 8.9 | 3.3 |
| O10_PEG(12k) | 20 | 3.2 |
| O10_PEG(20k) | 11 | 3.6 |
| O10_PEG(30k) | | 3 |
| O10_—CH4 | 0.8 | |

Example 21

Pharmacokinetic Studies in Mice

Pharmacokinetic studies in mice were performed to determine plasma levels of the hNGAL muteins over time after i.v., s.c. or i.p. administration according to standard procedures. Unmodified hNGAL muteins, PEGylated forms, and ABD- or CH4 fusion hNGAL muteins were administered as a bolus dose of 2-7.5 mg/kg. Terminal blood samples were collected at appropriate time points after dosing from 3 animals per time point. The concentration of double tagged lipocalin muteins in plasma samples was determined with a sensitive and quantitative sandwich ELISA using a StrepTag specific antibody (Qiagen) for capture and anti-T7-HRP conjugate (Novagen) for detection. The concentration of site-directly PEGylated O10 and O10-ABD in mouse plasma samples was quantified by functional capturing of the muteins via mCTLA-4-Fc (Chimerigen) and detected via a goat-anti hNGAL-specific polyclonal antibody (R+D Systems) and a mouse anti-goat IgG-HRP conjugate (Sigma). Pharmacokinetic calculations were performed by non-compartmental and 2-compartmental analysis yielding similar t1/2 values. A terminal serum half life of approximately 27 minutes was determined for the CTLA-4 specific lipocalin mutein S94.7-Q13 (see FIG. 11). Serum half-life was considerable extended by recombinant fusion with an albumin binding domain to approximately 8 hours in case of S94.7-Q13-ABD or by random pegylation to approximately 11.4 hours in case of F92.1-J08-PEG (see FIG. 11). The half-life extended version of S140.4-O10 exhibited terminal serum half lives of approximately 9.1 hours in the case of the ABD-fusion and 3.9 hours for the CH4-dimer (see FIG. 21). Determination of terminal serum half lives for the PEGylated O10 illustrates the possibility of half life tuning and resulted in 2.7 hours and 7.8 hours for a 20 k-PEG and a 30 k-PEG, respectively (see FIG. 21).

Bioavailability of naked S140.4-O10 as well as serum half life extended versions thereof was investigated in mouse PK studies. Naked S140.4-O10 was administered to mice intravenously, intraperitoneal or subcutaneous and after i.p. administration of O10-ABD and the Pegylated mutein (30 k-PEG) for comparison. Good bioavailability of both variants was observed after i.p. administration and terminal serum half lives were comparable to the ones obtained after i.v. administration (see FIG. 22).

Example 22

Tumor Growth Inhibition Study of the Anti-CTLA-4 hNGAL Mutein F92.1 J08 in a Syngenic Animal Model A previously described syngeneic CSA1M fibrosarcoma tumor model (Yang et al (1997) Cancer Res. 57, 4036-4041) was used to test the in vivo activity of F92.1-J08. Fibrosarcoma is a malignant tumor developed at the expense of fibroblasts generally sub-cuteanously. CSA1M cells were kindly provided by Dr. Hiromi Fujiwara (Osaka) and originally derived by Dr. Takato Yoshida (Yokohama). CSA1M cells were decontaminated from *mycoplasm* using Mynox reagent according to recommendations of the supplier (Minerva Biolabs) prior to the use in animal experiments. A PCR based *mycoplasm* detection system VenorGeM PCR Kit (Minerva Biolabs) was used to assure that CSA1M cells were free of mycoplasms. Log-growing CSA1M cells were trypsinized, counted, washed and re-suspended in serum-free DMEM medium for subcutaneous injection of $1.0 \times 10^6$ CSA1M cells in 200 µl subcutaneously onto the flank of Balb/c mice. Under these conditions all mice developed progressively growing tumors as determined in a pilot study. Tumor therapy with CTLA-4 blocking lipocalin mutein was started on the same day about 4 hours after tumor cell injection. The lipocalin mutein was produced for these studies as described in example 4. The 4F10 antibody was produced for these studies as described in example 16. Groups of 12 animals were administered with vehicle (PBS), a positive reference monoclonal antibody 4F10 and the CTLA-4 specific lipocalin mutein F92.1_J08 several times by i.p. injection. Mice treated with PBS or F92.1_J08 received two daily doses (at least 8 hours apart) of 200 µl PBS or test substance (300 µg) on 14 occasions, daily from Day 0 (the day of CSA1M cell injection). Mice treated with the mAb 4F10 received 100 µg in 200 µl on 7 occasions, every other day from Day 0. Animals were monitored daily and tumors were measured using an external caliper twice a week. The tumor dimensions measured over the period of the study. Tumor length (L, long) and width (W, short) were used to calculate tumor volume (V) in $mm^3$ using the following formula $V=(W2 \times L)/2$. A small, palpable tumor developed in all mice injected with CSA1M cell s.c. Tumors grew progressively in all vehicle treated animals where as CTLA-4 blockade by the monoclonal antibody 4F10 or the lipocalin mutein F92.1-J08 inhibited tumor growth with comparable efficacy. Palpable tumor nodules at day 3 reseeded similarly indicated by a similar decline in mean tumor volume. Furthermore, 9 and 8 out of 12 mice were completely free of a palpable tumor nodule 5 weeks after injection of CSA1M cells in the 4F10 and F92.1-J08 treated group respectively (see FIG. 10).

Additional syngeneic tumor models including, but not limited to, for example 51Blim10 or SaI/N (Leach et al. (1996) Science 271, 1734-1736), pTC1 (Kwon et al. (1997) PNAS 94, 8099-8103) or OV-HM ((Yang et al (1997) Cancer Res. 57, 4036-4041) can be used analogous to the above described protocol to demonstrate in vivo efficacy of CTLA-4 specific lipocalin muteins.

Example 23

Tumor Growth Inhibition Study of the Anti-CTLA-4 hNGAL Mutein S140.4 O10 in a Syngenic Animal Model The same syngeneic CSA1M fibrosarcoma tumor model as described in example 22 was used to test the in vivo activity of S140.4_O10. As previously, tumor therapy with the CTLA-4 blocking lipocalin mutein was started on the same day about 4 hours after tumor cell injection. Groups of 12 animals were administered with vehicle (PBS), a positive reference monoclonal antibody 4F10 and the CTLA-4 specific lipocalin mutein S140.4-O10 several times by i.p. injection. Mice treated with PBS or S140.4-O10 received two daily doses (at least 8 hours apart) of 200 µl PBS or lipocalin mutein (140 or 300 µg) on 14 occasions, daily from Day 0 (the day of CSA1M cell injection). Mice treated with the mAb 4F10 received 100 µg in 200 µl on 7 occasions, every other day from Day 0. Two additional groups were included in this study to deliver the lipocalin mutein via Alzet osmotic pumps (Charles River Laboratories). 12 Balb/c mice per group were implanted with Alzet osmotic pumps, model 2001 under the skin on the opposite flank of mice on the day of CSA1M cell injection. Pumps were filled with 200 µl of vehicle or S140.4-O10 at a concentration of 10 mg/ml and primed prior to implantation. The Alzet pumps were replaced with new and primed pumps after 7 days and the second serially implanted pump was removed on day 14 after tumor cell injection. Animals were monitored daily and tumors were measured using an external caliper twice a week. The tumor dimensions measured over the period of the study—length (L, long) and width (W, short) were used to calculate tumor volume (V) in $mm^3$ using the following formula $V=(W2 \times L)/2$. Mean values of tumor volumes and the standard error of the mean were calculated and a student t test was used for a statistical evaluation. As shown in FIG. 17, a clear and statistical significant inhibition of tumor growth could be observed when mice were treated with the lipocalin mutein S140.4-O10 either by multiple i.p. injections using 140 µg or 300 µg per injection (FIG. 17A) or when a total of 4 mg of the lipocalin mutein S140.4-O10 was delivered continuously via Alzet pumps over 14 days (FIG. 17B).

Example 24

Combination Therapy of CTLA-4 Blocking Lipocalin Muteins with Chemotherapy in Syngenic Animal Models It also encompassed in the present invention to combine CTLA-4 specific lipocalin muteins with a chemotherapy regiment in the treatment of melanoma or other cancer types. The immunosuppressive potential of anticancer drugs has been recognized for a long time (Santos et al. (1964) Ann NY Acad Sci. 114, 404-423). Nevertheless, an enhancement of immune responses has been described as well (Ehrke et al. (1986) Cancer Res 46, 54-60, Maguire et al. (1967) J. Invest Dermatol. 48, 39-43, Ozer et al. (1982) J Exp Med 155, 276-290) and synergy with CTLA-4 blockade was demonstrated with a low dose regime in a plasmacytoma tumor model (Mokyr et al., Cancer Res. 58: 5301-04). Therefore, certain chemotherapeutics have been combined with tumor cell vaccines in patients with advanced melanoma and renal carcinoma (Berd et al. (1986) Cancer Res 46, 2572-2577, Berd et al. (1990) J. Clin. Oncol. 8, 1858-1867, and others). Dacarbazine (DTIC) for example has been used alone or in combination with other chemotherapeutics or biologics including anti-CTLA-4 mAb in late stage melanoma.

To this aim lipocalin muteins or a control antibody such as antibody 4F10 can be administered as mono therapy and in combination with a chemotherapeutic compound e.g. dacarbazine (DCZ) in the B16-F1 mouse melanoma model in vivo. B16-F10 tumour fragments of approximately 1 mm$^3$ will be subcutaneously inoculated in female B6D2F1 mice at Day 0. Chemotherapeutics will be administered in a dose and schedule previously determined to be optimal in this model. Dacarbazine (15-60 mg/kg) will be administered intraperitoneal 3 times a week for 3 consecutive weeks starting at day 7 after tumor inoculation. Lipocalin muteins and antibodies will be administered as described in example 22 starting on day 7 after tumor inoculation. Measurements of the subcutaneous tumours will be done with callipers 2 times a week. Mice will be twice daily observed for general health status and sacrificed when moribund. It is this day of sacrifice that is said to be the day of death. In case mice would not become moribund within 60 days after the day of sacrifice of the last control mouse, these animals are considered to be cured and sacrificed at that moment. Parameter for activity is prolongation of survival and inhibition of tumour growth. The effects on prolongation of survival will be evaluated by 2 means. First the % T/C-value is calculated. This % T/C-value is calculated by dividing the day of death of the median mouse in a treated group T by the day of death of the median mouse in the control group C, the latter said to be 100%. A T/C-value greater than 130% indicates a relevant prolongation of survival as compared to the vehicle treated group. The second way of evaluating the effect upon survival is by a Kaplan-Meier analysis. The cut-off level for significance by log-rank statistics is set at a p-value of p<0.05. Statistical analysis of the effects of treatment on subcutaneous tumour growth will be performed with the Mann-Whitney U-test. Here also the statistical cut-off level is p<0.05.

Example 25

Combination Therapy of CTLA-4 Blocking Lipocalin Mutein with Tumor Vaccination in Syngenic Animal Models It also encompassed in the present invention to combine CTLA-4 specific lipocalin muteins with a tumor vaccination regiment for the treatment of melanoma or other cancer types. Syngeneic melanoma tumor models like B16 or B16 transfected with a surrogate tumor antigen like ovalbumin can be used in combination with a tumor cell vaccine or ovalbumin based vaccine respectively. Animals will be either vaccinated prior or after challenge with live tumor cells. Various vaccination strategies could be used including irradiated tumor cells, tumor cells transfected with cytokines like GM-CSF, tumor specific or associated antigens together with adjuvant formulations or loaded on professional antigen presenting cells. Synergy of a CTLA-4 blockade by a CTLA-4 specific lipocalin mutein with various vaccination strategies can for example be tested in the B16 melanoma model. Mice will be challenged with an appropriate amount of syngeneic B16 melanoma cells (between $5 \times 10^4$ and $5 \times 10^6$) for example 15 days after a vaccination with $1 \times 10^5$-$1 \times 10^7$ gamma-irradiated (35 Gy) B16 cells injected intraperitoneal either at a single dose on day 1 (vaccination I) or by three i.p. injections ($1 \times 10^7$ cells each) on day 1, 8 and 15 respectively (vaccination II). CTLA-4 specific lipocalin muteins will be administered intraperitoneal or intravenously at an effective dose starting with the day of the immunization. Tumour growth of subcutaneous B16 challenge tumors will be monitored in terms of tumor volumes. Lung metastases will be counted microscopically after termination of the study. Satellite groups will be included in every case to quantify the strength of the induced tumor-specific CTL response 7 days after tumor challenge using a $^{51}$Cr release assay of spleen cells against the respective tumor, an irrelevant tumor, and the NK sensitive target cell line YAC-1.

The B16 melanoma tumor model or other relatively low immunogenic syngeneic tumor models can be combined with other vaccination approaches for example GM-CSF transfected tumor cells (Elsas et al., J. Exp. Med., 1999, 190, 355-366, Hurvitz et al. PNAS 1998 95: 10067-71, Hurvitz et al., Cancer Res. 2000 60: 2444-48), peptide vaccines (Davila et al., Cancer Res. 2003 63: 3281-88, Ito et al., JI 2000 164:1230-35), DNA vaccines (Gregor et al., Vaccine 2004 22: 1700-08) or dendritic cells (Santulli-Marotto et al., Canc. Res. 2003, 63: 7483-89) analogous to the above described protocol to demonstrate in vivo efficacy of CTLA-4 specific lipocalin muteins. In addition, CTLA-4 blockade by a lipocalin mutein can be combined for example with surgical removal or irradiation of the primary tumor (Kwon et al., PNAS 1999, 96, 15074-79 and Demaria et al., Clin Cancer Res. 2005, 11, 728-34).

Example 26

CTLA-4 Specific Lipocalin Muteins Excert their Enhancing Effect on Effector T Cells in Solid Tumors The activation of a T-cell response is a complex process involving co-stimulatory receptors expressed on T cells. Positive co-stimulatory signals are mediated primarily by CD28 interactions where as negative co-stimulatory signals are primarily mediated by cytotoxic T lymphocyte-associated antigen (CTLA-4) interactions with members of the B7 family of antigen-presenting cells (APC). Tumor derived peptides are displayed on MHCI and MHCII molecules and cross-presented to T cells by professional antigen presenting cells (APC) primarily in secondary lymphoid organs as spleen and lymphnode. APC's aquire, process and ferry the antigen from the tumor tissue to draining lymphnodes (Kripke M L et al., J Immunol. 1990, 145(9):2833-8). In addition, T cells could be primed and/or re-stimulated by peptide-MHC complexes on tumor cells themselves or APC's in the tumor. Alternatively, CTLA-4 blockade in the tumor might affect T cell effector functions directly or indirectly through inhibiting the suppressive activity of regulatory T cells. For example, a CTLA-4 blocking monoclonal antibody exerted its effect not in the lymphnode but in the pancreas where activated T cells re-encounter their antigen in an adoptive transfer model with TCR transgenic diabetogenic T cells (Luhder F et al., Proc Natl Acad Sci USA. 2000, 97(22):12204-9). Inhibition of CTLA-4/B7 interactions in the tumor environment might be critical for a successful tumor therapy. It is thus also encompassed in the present invention that CTLA-4 binding lipocalin muteins are able to enhance tumor specific T cell immunity more effectively compared to monoclonal antibodies due to their smaller size and assumed better tumor penetration. To elucidate the critical period of administration and anatomical place of action one could compare the efficacy of a CTLA-4 blocking lipocalin mutein in a syngeneic tumor model as described in Example 25 when administered early or at later time points after a therapeutic tumor specific vaccination in tumor bearing animals. The duration of a CTLA-4 blockade could be adjusted in case of lipocalin muteins due to their relative short serum half live, where as monoclonal antibodies would be present in significant amounts for several days. Since the process of antigen uptake, processing and presentation follows a defined spatial and temporal pattern one could limit CTLA-4 blockade during the initial T cell activation and expansion phase in spleen and lymphnodes and/or inhibit CTLA-4 during the effector phase in the tumor tissue.

To circumvent a need for T cell activation in the lymphnode one could transfer in vitro activated and matured tumor-specific effector TCR transgenic T cells that would home directly to the tumor tissue of tumor bearing mice. To this aim, for example OT-I TCR transgenic T cells would be stimulated in vitro under the appropriate conditions with ovalbumin pulsed antigen presenting cells and transferred into C57/1316 mice harboring B16 melanomas transfected with a ovalbumin expression vector (B16-OVA). Direct homing of OT-I T cells into the tumor tissue could be monitored by flow cytometry using MHC pentamer reagents (H2-kb/SIINFEKL (SEQ ID NO: 83) pentamer-PE, Proimmune). Functional activity of tumor infiltrating T cells could be assessed in vitro using a tumor specific INF□ ELISspot assay and tumor growth would be monitored. We predict that transferred effector OT-I T cells would exhibit an enhanced tumor specific functional activity measured by ELIspot assay and/or inhibit B16-OVA tumor growth more efficiently in the presence of pharmacolocigal active amounts of a CTLA-4 blocking lipocalin mutein such as S140.4-O10 or F92.1-J08 or half live extended versions thereof. In addition, S140.4-O10, F92.1-J08 or half life extended versions might be more effective than a monoclonal antibody in such an experiment due to better tumor penetration.

Example 27

CTLA-4 Specific Lipocalin Muteins for the Treatment or Prevention of Infectious Diseases T lymphocytes are essential in fighting many different types of infections, in mediating rejection of transplants and contributing to host defenses against tumors. The activation of a T-cell response is a complex process involving co-stimulatory receptors expressed on T cells. Positive co-stimulatory signals are mediated primarily by CD28 interactions where as negative co-stimulatory signals are primarily mediated by cytotoxic T lymphocyte-associated antigen (CTLA-4) interactions with members of the B7 family of antigen-presenting cells (APC). The dynamic integration of the TCR, CD28 and CTLA-4 signals determines the outcome of T-cell activation, expansion and peripheral tolerance. Over the past several years it was demonstrated that antibodies blocking CTLA-4/B7 interactions can greatly enhance T-cell responses in a number of different experimental models including infectious disease. A beneficial effect of CTLA-4 blockade on the pathogen clearance or disease pathology has been demonstrated in animal models of parasitic infections with *Leishmania* (Murphy et al. (1998) J Immunol. 161(8), 4153-4160, Zubairi S et al., Eur J Immunol. 2004, 34(5): 1433-40), *Trypanosoma cruzi* (Martins et al. (2004) J Immunol. 172(8), 4893-4901), *Cryptococcus* (McGaha et al. (2000) Infect Immun. 68(8), 4624-4630) or Nematodes (McCoy et al. (1997) J Exp Med. 186(2), 183-187). In addition, certain polymorphism in CTLA-4 have been linked to HTLV-1 infections and CD4 T cells from HIV infected patients appear to express detectable levels of CTLA-4 which increase over the course of infection (Steiner et al. (1999) Clin Exp Immunol. 115(3), 451-457). In vitro data suggest that CTLA-4 blockade could contribute to the immunological control of HIV (Riley et al. (2000) J Exp Med. 191(11), 1987-1997). Polymorphisms in the CTLA-4 haplotype have been correlated with the response rate to standard therapy of chronic hepatitis C suggesting it as a possible target (Yee et al. (2003) J. Infect. Dis. 187(8), 1264-1271).

It is also encompassed in the present invention to use CTLA-4 specific lipocalin muteins as adjuvants to improve infectious disease specific vaccines that would otherwise require multiple doses or are ineffective in the treatment of chronic or drug resistant infectious diseases. A combination with anti-infectious drugs that are non curative or of suboptimal efficacy is thus also encompassed herein for the treatment of infectious diseases as well. Animal models such as described in the literature cited can be used by the expert skilled in the art for the evaluation of a beneficial role of CTLA-4 specific lipocalin muteins in the treatment of infectious diseases. The main advantage of a lipocalin mutein should be its shorter half-life compared to an antibody as the enhancement of a vaccine specific immune response would be limited temporally to the immediate vaccine response and should decrease the risk of autoimmune reactions.

Example 28

Testing of hNGAL Mutein-Toxin Complexes for Toxic Effects in a CHO Cell Line Expressing Human CTLA-4

CTLA-4 specific toxicity of an hNGAL mutein based immunotoxin was demonstrated in a proliferation assay with CTLA-4 and vector transfected CHO cells (described in Example 16). 2500 cells were plated in triplicates in a 96 well plate in medium containing 5% FCS. Saporin-conjugated neutravidin (custom conjugate, Advanced Targeting Systems) was incubated for 30 min at room temperature with a 4-fold molar amount of biotinylated CTLA-4 binding mutein F92.1-J08, biotinylated wild type hNGAL58 or biotinylated CTLA-4 specific control antibody. 8H5-bio (Ancell). The lipocalin mutein and the wild type hNGAL were biotinylated with EZ-Link Sulpho-NHS-LC-LC-Biotin (Pierce) as recommended by the manufacturer. In brief, the proteins were mixed with a 2:1 molar excess of biotin reagent in PBS and incubated at RT for 1 h. The excess reagent was removed by desalting over PD-10 columns (Pharmacia). Complexes between biotinylated reagents and neutravidin-saporin were added to the cells in mutein or antibody concentrations of 40 or 80 nM. The cells were incubated for 72 h, and fresh lipocalin mutein/neutravidin/saporin complexes were added daily. After 72 h proliferation was analyzed by MTS assay according to the recommendations of the manufacturer (Promega). All results were set in correlation to the proliferation of untreated cells. In vector-transfected control cells there was no significant change of proliferation with any of the substances, whereas CTLA-4-transfected cells showed significant decrease of proliferation after incubation with the toxin complex of the lipocalin mutein F92.1-J08 and the corresponding toxin-antibody complex, but not with the hNGAL58 toxin complex (see FIG. 13).

Example 29

Testing of hNGAL Mutein-Toxin Complexes for Toxic Effects in a CHO Cell Line Expressing Human CTLA-4

CTLA-4 specific toxicity of an hNGAL mutein based immunotoxin was demonstrated further in a proliferation assay with CTLA-4 and vector transfected CHO and A431 cells (described in Example 16). Cells were plated in triplicates in a 96 well plate in medium containing 5% FCS. Saporin-conjugated neutravidin (custom conjugate, Advanced Targeting Systems) was incubated for 30 min at room temperature with an equal molar amount of biotinylated monoclonal antibody 8H5 (Ancell). The lipocalin mutein was conjugated to saporin via a disulfide containing linker in a lipocalin mutein/saporin ratio of approximately 1:1 to 1:2 (custom conjugates, Advanced Targeting Systems). The lipocalin mutein saporin conjugate, a mixture of unconjugated lipocalin mutein and free saporin or the complex between biotinylated monoclonal antibody 8H5 and neutravidin-saporin was added to the cells in lipocalin mutein or antibody concentrations between 0.01 nM and 100 nM at the start of the in vitro culture. Cell proliferation was analyzed by MTS assay according to the recommendations of the manufacturer (Promega) after a 72 to 96 h incubation period. All results were set in correlation to the proliferation of untreated cells set as 0% inhibition. CTLA-4 specific inhibition of proliferation could be observed with the 8H5-bio/NA-saporin complex as well as the S140.4-O10-saporin lipocalin mutein conjugates in a dose dependent manner with human CTLA-4 transfected CHO cells (see FIG. 16a) and A431 cells (see FIG. 16b).

Example 30

Lipocalin Muteins Reverse Human and Mouse CTLA-4 Fc Inhibition of T Cells Activation in an Anti-EBV Transformed Human B Cell Mixed Lymphocyte Reaction The lipocalin mutein S140.4-O10 reversed the functional inhibition of T cell responses by human and mouse CTLA-4 Fc in a mixed lymphocyte reaction (MLR). To this aim, T cells were isolated from PBMC using lymfokwik-T (One Lambda Inc, Canoga Park, Calif.) as indicated by the supplier. The T cells ($5 \times 10^4$-$10^5$ T cells/well of a 96-well flat bottom plate) were cocultured with varying numbers of 5000 RAD irradiated JY cells (human EBV transformed B cell line), 5% fetal calf serum, and 80 μg/ml gentamycin. The cells were cultured at 37° C., 5% $CO_2$ in a humidified atmosphere (95% relative humidity). To these cultures lipocalin muteins or antibodies+/−CTLA-4 Fc was added. After a 120 hour incubation period supernatants were removed to measure the production of IFN-γ and proliferation was measured by $^3$H-thymidine incorporation. CTLA-4 Fc (both human and murine) almost completely inhibited the JY-specific MLR as evidenced by $^3$H-thymidine incorporation and IFN-γ production. Two independent production batches of the lipocalin mutein S140.4-O10 as well as CTLA-4-specific mAbs BNI3 human) and 4F10 (mouse) could completely reverse the inhibitory effect of CTLA-4-Ig on the anti-JY MLR (see FIG. 18, top panel with human CTLA-4 Fc and bottom panel with mouse CTLA-4 Fc). In contrast, two independent production batches of the negative control hNGALwt-58 and antibody isotype control did not have any effects. The functional reversal of human and mouse CTLA-4-Ig induced inhibition of the JY-specific MLR by the lipocalin mutein S140.4-O10 was reproduced in experiments using T cells isolated from different donors.

Example 31

Lipocalin Muteins Enhance PHA Blast T Cells Activation in an Anti-EBV Transformed Human B Cell Mixed Lymphocyte Reaction The functional activity of lipocalins muteins was further demonstrated in a mixed lymphocyte reaction (MLR) against allogeneic (MHC disparate) CD80+ and CD86+ JY cells (EBV-transformed human B-cell). To this aim, PHA blasts were generated by culturing human PBMC for 72 h in the presence of PHA (1 μg/ml). JY cells were collected, irradiated (3500 RAD) and cocultured (at different concentrations) with washed T cell blasts ($10^5$/well) in the presence or absence of anti-human CTLA-4 specific antibody BNI3 or lipocalin muteins at 50 μg/ml. Supernatants were collected after 48 and 96 hours and INFγ was measured by a quantitative ELISA. PHA blasts in the absence of stimulating JY cells produced no more than 19 pg/ml INFg with or without lipocalin muteins or antibodies present. A relative weak T cell activation was observed with 5000 JY cells (two fold increase in INFγ) which could be significantly enhanced through CTLA-4 blockade by the lipocalin mutein S140.4-O10 or the monoclonal antibody BNI3 but not with the negative control lipocalin wild type or antibody isotype (see FIG. 19 top panel). The same trend could be observed even when a strong T cell response (more than 100 fold increase in INFγ) was obtained in the MLR assay with 25000 JY cells (see FIG. 19 bottom panel).

Example 32

Assessment of Cross-Reactivity of Lipocalin Mutein S140.4-O10 with Normal Human Tissues The objective of this study was to evaluate the potential cross-reactivity of the test article with cryosections of normal human tissues. In order to detect binding, the lipocalin mutein S140.4-O10 and the isotype matched lipocalin hNGALwt was applied to cryosections of normal human tissues (1 donor per tissue, where available) at two concentrations (40 mg/mL and 5 mg/mL). Additionally, each tissue was stained with a commercial murine MsIgG2a anti-CTLA-4 monoclonal antibody (clone BNI3.1, designated BNI3) and its isotype-matched negative control antibody, MsIgG2a. Tissues that had been obtained previously via autopsy or surgical biopsy were embedded in Tissue-TekÒ O.C.T. medium, frozen on dry ice, and stored in sealed plastic bags below −70° C. Tissues were sectioned at approximately 5 mm and fixed in acetone for 10 minutes. An indirect immunoperoxidase procedure was performed to evaluate binding of test substances to normal human tissue sections. The staining procedures, primary and secondary antibody dilutions, and controls were qualified in preliminary staining runs for this study. Acetone-fixed cryosections were rinsed twice in phosphate-buffered saline (PBS [0.15M NaCl, pH 7.2]). Endogenous peroxidase was blocked by incubating the slides with the peroxidase solution provided in the Dako EnVision+ Kit for 5 minutes and rinsing twice in PBS (0.15M NaCl, pH 7.2). Next, the slides were treated with a protein block designed to reduce nonspecific binding for 20 minutes. The protein block was prepared as follows: PBS (0.15M NaCl, pH 7.2); 0.5% casein; 1% bovine serum albumin; and 1.5% normal goat serum. Following the protein block, the primary antibody (test article, negative control antibody, or none [buffer alone as the assay control]) was applied at room temperature for one hour. Next, the slides were rinsed two times with PBS (0.15M NaCl, pH 7.2). Then, the unconjugated secondary antibody (mouse anti-StrepTag) was applied for 30 minutes. Next, the slides were rinsed two times with PBS (0.15M NaCl, pH 7.2), treated with the peroxidase-labeled goat anti-mouse IgG polymer supplied in the Dako EnVision+ Kit for 30 minutes, rinsed two times with PBS (0.15M NaCl, pH 7.2), and treated with the substrate-chromogen (DAB+) solution supplied in the Dako EnVision+ Kit for 8 minutes. All slides were rinsed with tap water, counterstained with hematoxylin, blued in saturated lithium carbonate, dehydrated through alcohols, cleared in xylene, and coverslipped for interpretation. PBS (0.15M NaCl, pH 7.2)+1% bovine serum albumin served as the diluent for all antibodies.

All slides were read by a certified Pathologist to identify the tissue or cell type stained and intensity of staining (graded ± [equivocal], 1+ [weak], 2+ [moderate], 3+ [strong], 4+ [intense], or Neg [negative]). All test article-stained slides and selected control slides were evaluated by the Reviewing Pathologist. All slides were judged for adequacy of tissue elements and staining. As a tissue control, rabbit anti-β2-microglobulin was reacted with cryosections of all human tissues (except blood smear). The β2-microglobulin antigen is a minor Class I determinant found on most tissues that is strongly expressed on endothelium. Its demonstration is indicative of localization of cell surface proteins by the normal tissues. These slides were fixed for 10 minutes in acetone and stained using an immunoperoxidase procedure and a rabbit anti-human 32-microglobulin antibody. These slides were subsequently reacted with DAB and interpreted as positive (Pos) or negative (Neg).

S140.4-O10 (phNGAL15) intensely stained the membrane of the positive control cells (CD152-expressing cells in cryosections of human tonsil) at both concentrations examined. S140.4-O10 (phNGAL15) did not specifically react with the negative control cells (CD152-non-expressing cells in cryosections of human tonsil [squamous epithelium]). The negative control lipocalin hNGALwt-58, did not specifically react with cryosections of positive or negative control cells (see FIG. 20). The excellent specific reactions of the test article with the positive control tissue and the lack of specific reactivity with the negative control tissues, as well as the lack of reactivity of the negative control antibody, indicated that the assay was sensitive, specific, and reproducible. BNI3 intensely stained the membrane of the positive control cells (CD152-expressing cells in cryosections of human tonsil) at the 5 μg/ml concentration. BNI3 did not specifically react with the negative control cells (CD152-non-expressing cells in cryosections of human tonsil [squamous epithelium]). The negative control antibody (MsIgG2a) did not specifically react with cryosections of positive or negative control cells. S140.4-O10 (phNGAL15)-specific reactivity was present in mononuclear cells in the kidney, spleen and tonsil. This CTLA-4 reactivity was confirmed by BNI3-specific staining of mononuclear cells membranes in the kidney, spleen and tonsil. No other reactivities or cross-reactivities were noted in this study (see FIG. 20). These findings were consistent with CTLA-4 expression reported in scientific literature.

Example 33

Production and Characterization of Alternative Cystein-Mutants of the hNGAL Mutein S140.4-O10 for Site-Directed PEGylation In order to increase the in vivo half-life of the CTLA-4-specific hNGAL mutein S140.4-O10 by site-directed PEGylation via alternative free cystein residues, lipocalin muteins were exemplarily modified by the following procedures.

Eleven suitable amino acid positions (see Table 11) were identified to introduce a free cystein residue in the hNGAL mutein S140.4-O10 via site-directed mutagenesis (Quickchange mutagenesis kit, Stratgene). The nucleotide sequences of these lipocalin muteins, named S140.4-O10_S146C, S140.4-O10_V84C, S140.4-O10_T141C, S140.4-O10_N116, S140.4-O10_A145C, S140.4-O10_E143C, S140.4-O10_S14C, S140.4-O10_S158C, S140.4-O10_Q88C, S140.4-O10_E60C, and S140.4-O10_N21C were translated into amino acid sequence and are given as SEQ ID NO 63, SEQ ID NO 64, SEQ ID NO 65, SEQ ID NO 66, SEQ ID NO 67, SEQ ID NO 68, SEQ ID NO 69, SEQ ID NO 70, SEQ ID NO 71, SEQ ID NO 72, and SEQ ID NO 73, respectively. The muteins were produced in a 1 l shakerflask as described in Example 4, however without the N-terminal T7-affinity tag. To this aim, the muteins were subcloned on the expression vector phNGAL15 via the BstXI restriction sites. phNGAL15 codes for a fusion protein of the OmpA-signal sequence with a modified hNGAL according to FIG. 1 (phNGAL35) with the exception of the three exchanges Arg81 to Ala, Lys125 to Ala and Lys134 to Ala and the Strep-Tag® II affinity tag. A relevant segment of the nucleic acid sequence of phNGAL15 is reproduced together with the encoded amino acid sequence in the sequence listing as SEQ ID NO: 62. The segment begins with the XbaI restriction site and ends with the HindIII restriction site. The vector elements outside this region are identical with the vector pASK75. Further purification of the muteins was carried out as described in example 4. Prior to the PEGylation reaction the free cystein residue was reduced using 1 mM TCEP for 1.5 h at RT. Before the PEGylation step the TCEP was removed completely from the reaction mixture by dialysis against 20 mM NaPhosphate buffer pH 7.0 with 150 mM NaCl. PEGylation was performed by mixing the protein with 3-fold molar excess of a 12 k PEG-maleimide reagent for 1 h at RT. The reaction was then stopped by adding 50 mM of cysteine.

In subsequent experiments the muteins were characterized in terms of expression yields, yield of monomeric protein and affinities towards hCTLA-4-Fc, either by ELISA or Biacore measurements, before and after the PEGylation reaction. Most of the muteins display expression yields and affinities towards hCTLA-4-Fc comparable to the original S140.4-O10 or the S87C variant, which was already used for site-directed PEGylation (see Example 20).

TABLE 11

Table 11. Expression yields from 11 shakerflask expression were determined after purification of the muteins by OD280 measurements. The yield of monomeric lipocalin mutein in [%] was calculated via integrating of peaks derived from analytical SEC-HPLC runs. The affinities of the muteins either were determined by Affinity-ELISA or by SPR-spectroscopy.

| Lipocalin mutein | Expression yield [µg/l] | Yield of monomer after SEC [%] | SPR-Affinity monomer [nM] | SPR-Affinity PEGylated monomer [nM] | ELISA-Affinity PEGylated Monomer [nM] |
|---|---|---|---|---|---|
| O10 | 210 | 95 | 3 | n.d. | 87 |
| O10_S146C | 180 | 95 | 9 | 50 | 100 |
| O10_V84C | 160 | 90 | 15 | 97 | 100 |
| O10_T141C | 105 | 88 | 4 | 69 | 82 |
| O10_S87C | 110 | 85 | 6 | 26 | 52 |
| O10_N116C | 100 | 85 | 10 | n.d. | n.d. |
| O10_A145C | 125 | 82 | 6 | 50 | 74 |
| O10_E143C | 85 | 78 | 15 | 85 | 103 |
| O10_S14C | 120 | 70 | 13 | n.d. | n.d. |
| O10_S158C | 105 | 70 | 13 | n.d. | n.d. |
| O10_Q88C | 100 | 60 | 15 | n.d. | n.d. |
| O10_E60C | 60 | 60 | 24 | n.d. | n.d. |
| O10_N21C | 85 | 40 | 32 | n.d. | n.d. |

What is claimed is:

1. A mutein derived from human neutrophil gelatinase-associated lipocalin (hNGAL), said mutein having binding specificity for the cytotoxic T lymphocyte-associated antigen (CTLA-4), wherein said mutein:
   (a) comprises the amino acid sequence of SEQ ID NO: 79 but for at least 12 amino acid replacements selected from the group consisting of A40R, A40Y, E44D, E44N, K46Q, K46R, D47H, D47Y, Q49M, K50Q, K50N, K50D, L70I, F71S, F71L, R72S, R72P, R72D, K73H, K73T, D77E, W79T, W79P, N96D, P101G, P101R, G102D, G102M, L103K, L103D, A125L, A125Q, V126A, S127E, S127N, S127G, Q128D, Q128H, N129D, R130A, R130T, Y132F, and Y132H; and
   (b) binds human CTLA-4 with a $K_D$ of 50 nM or less.

2. The mutein of claim 1, wherein said mutein: blocks the interaction between CTLA-4 and its physiological ligands CD80 (B7-1) and/or CD86 (B7-2).

3. The mutein of claim 1, wherein the mutein binds human CTLA-4 with a $K_D$ of 25 nM or less.

4. The mutein of claim 1, wherein the mutein binds murine CTLA-4 with a $K_D$ of 200 nM or less.

5. The mutein of claim 1, wherein the specificity of binding expressed as the ratio $r=K_D$ for the complex between mutein and human CTLA-4/$K_D$ for the complex between mutein and murine CTLA-4 has a value of 20 or less, or of 1 or less, or of 0.5 or less.

6. The mutein of claim 1, wherein at least one of said amino acid replacements is F71S.

7. The mutein of claim 1, wherein at least one of said amino acid replacements is R72S.

8. The mutein of claim 1, which has an amino acid sequence further differing from that corresponding to SEQ ID NO: 79 by additionally at least one of the amino acid replacements selected from the group consisting of I55V, N65D, Q88R, N114D, N116S, H118Y, and M120V.

9. The mutein of claim 1, which has an amino acid sequence further differing from that corresponding to SEQ ID NO: 79 by additionally at least one of the amino acid replacements selected from the group consisting of S14C, N21C, E60C, V84C, Q88C, N116C, T141C, E143C, A145C, S146C, and S158C.

10. The mutein of claims 1, wherein the mutein has an amino acid sequence selected from the group consisting of SEQ ID NOs: 34, 35, 37, 47, 48, 49, 50, 51, 52, 53, 54, 63, 64, 65, 66, 67, 68, 69, 70, 71, 72, and 73.

11. The mutein of claim 1, wherein the mutein is conjugated to a compound selected from the group consisting of an organic molecule, an enzyme label, a radioactive label, a fluorescent label, a chromogenic label, a luminescent label, a hapten, biotin, a metal complex, a metal, colloidal gold, a cystostatic agent, a toxin and a moiety that extends the serum half-life of the mutein.

12. The mutein of claim 1, wherein the mutein is conjugated to a toxin selected from the group consisting of pertussis-toxin, diphtheria toxin, ricin, saporin, pseudomonas exotoxin, calicheamicin, a taxoid, a maytansinoid, a tubulysin auristatin E, monomethylauristatin E, auristatin PYE and auristatin PHE.

13. The mutein of claim 11, wherein the moiety that extends the serum half-life of the mutein is selected from the group consisting of a polyalkylene glycol molecule, hydroxyethylstarch, a Fc part of an immunoglobulin, a CH3 domain of an immunoglobulin, a CH4 domain of human IgE, an albumin binding peptide, and an albumin binding protein.

14. The mutein of claim 1, wherein the mutein is fused at its N-terminus and/or its C-terminus to a protein, a protein domain or a peptide.

15. The mutein of claim 14, wherein the protein domain is a CH4 domain of human IgE, which extends the serum half-life of the mutein.

16. A nucleic acid molecule comprising a nucleotide sequence encoding a mutein of claim 1.

17. A host cell containing a nucleic acid molecule of claim 16.

18. A pharmaceutical composition comprising a mutein of claim 1.

* * * * *

UNITED STATES PATENT AND TRADEMARK OFFICE
CERTIFICATE OF CORRECTION

PATENT NO. : 7,892,827 B2
APPLICATION NO. : 11/720234
DATED : February 22, 2011
INVENTOR(S) : Gabriele Matschiner et al.

It is certified that error appears in the above-identified patent and that said Letters Patent is hereby corrected as shown below:

Col. 149, claim 5, lines 59-61, replace the formula:

"ratio $r=K_D$ for the complex between mutein and human CTLA-4/$K_D$ for the complex between mutein and murine CTLA-4"

with the following:

$$\text{ratio } r = \frac{K_D \text{ for the complex between mutein and human CTLA-4}}{K_D \text{ for the complex between mutein and murine CTLA-4}}$$

Col. 150, claim 8, line 38, "155V" should be --I55V--.

Col. 150, claim 10, line 46, "claims 1" should be --claim 1--.

Signed and Sealed this
Tenth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,892,827 B2 | Page 1 of 1 |
| APPLICATION NO. | : 11/720234 | |
| DATED | : February 22, 2011 | |
| INVENTOR(S) | : Matschiner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this
Twelfth Day of July, 2011

David J. Kappos
*Director of the United States Patent and Trademark Office*

SEQUENCE LISTING

```
<160> NUMBER OF SEQ ID NOS: 83

<210> SEQ ID NO 1
<211> LENGTH: 77
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(32)
<223> OTHER INFORMATION: a, c, g, or t
<220> FEATURE:
<221> NAME/KEY: modified_base
<222> LOCATION: (37)..(38)
<223> OTHER INFORMATION: a, c, g, or t
<220> FEATURE:
<221> NAME/KEY: modified_base
<222> LOCATION: (49)..(50)
<223> OTHER INFORMATION: a, c, g, or t
<220> FEATURE:
<221> NAME/KEY: modified_base
<222> LOCATION: (52)..(53)
<223> OTHER INFORMATION: a, c, g, or t
<220> FEATURE:
<221> NAME/KEY: modified_base
<222> LOCATION: (58)..(59)
<223> OTHER INFORMATION: a, c, g, or t

<400> SEQUENCE: 1
ggctgggaac ctggaacaaa agtcgcgatm nngtamnnac acttcttmnn mnnaaamnng        60
acggaggtga cattgta                                                      77

<210> SEQ ID NO 2
<211> LENGTH: 77
<212> TYPE: DNA
<213> ORGANISM: Artificial Sequence
<220> FEATURE:
<223> OTHER INFORMATION: Description of Artificial Sequence: Synthetic
```

```
        primer
<220> FEATURE:
<221> NAME/KEY: modified_base
<222> LOCATION: (33)..(34)
<223> OTHER INFORMATION: a, c, g, or t
<220> FEATURE:
<221> NAME/KEY: modified_base
<222> LOCATION: (39)..(40)
<223> OTHER INFORMATION: a, c, g, or t
<220> FEATURE:
<221> NAME/KEY: modified_base
<222> LOCATION: (45)..(46)
<223> OTHER INFORMATION: a, c, g, or t
<220> FEATURE:
<221> NAME/KEY: modified_base
<222> LOCATION: (48)..(49)
<223> OTHER INFORMATION: a, c, g, or t
<220> FEATURE:
<221> NAME/KEY: modified_base
<222> LOCATION: (54)..(55)
<223> OTHER INFORMATION: a, c, g, or t

<400> SEQUENCE: 2
ccttggttct cccgtagatg gtaatcgcga amnnctcmnn gttmnnmnna acmnncttaa       60
agaacaccat agcatgc                                                     77

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cttccaggac aaccaattcc atgggaagtg gtatgtggta ggtctcgcag ggaa            54

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctttagttc cgaagccagc tccttggttc tcccgtaga                             39

<210> SEQ ID NO 5
<211> LENGTH: 1890
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5
tctagataac gagggcaaaa aatgaaaaag acagctatcg cgattgcagt ggctctggct      60
ggcttcgcta ccgtagcgca ggccatggct tccatgaccg gtggtcagca gatgggtcag     120
gactccacct cagacctgat cccagcccca cctctgagca aggtccctct gcagcagaac     180
ttccaggaca accaattcca tgggaagtgg tatgtggtag gtctcgcagg gaatgcaatt     240
ctcagagaag acaaagaccc gcaaaagatg tatgccacca tctatgagct gaaagaagac     300
aagagctaca atgtcacctc cgtcctgttt aggaaaaaga gtgtgactac ctggatcgcg     360
acttttgttc caggttccca gccaggcgag ttcacgctgg gcaacattaa gagttaccct     420
```

```
ggattaacga gttacctcgt ccgagtggtg agcaccaact acaaccagca tgctatggtg    480
ttcttcaagg cagtttctca aaacagggag tacttcgcga ttaccatcta cgggagaacc    540
aaggagctgg cttcggaact aaaggagaac ttcatccgct ctctaaatc tctgggcctc     600 cctgaaaacc acatcgtctt ccctgtccca atcgaccagt gtatcgacgg cagcgctggt    660
ggggcctaga ctgttgaaag ttgtttagca aaaccccata cagaaaattc atttactaac    720
gtctggaaag acgacaaaac tttagatcgt tacgctaact atgagggctg tctgtggaat    780
gctacaggcg ttgtagtttg tactggtgac gaaactcagt gttacggtac atgggttcct    840
attgggcttg ctatccctga aaatgagggt ggtggctctg agggtggcgg ttctgagggt    900
ggcggttctg agggtggcgg tactaaacct cctgagtacg tgatacacc tattccgggc      960 tatacttata tcaaccctct cgacggcact tatccgcctg gtactgagca aaaccccgct    1020
aatcctaatc cttctcttga ggagtctcag cctcttaata ctttcatgtt tcagaataat    1080
aggttccgaa ataggcaggg ggcattaact gtttatacgg gcactgttac tcaaggcact    1140
gaccccgtta aaacttatta ccagtacact cctgtatcat caaaagccat gtatgacgct    1200
tactggaacg gtaaattcag agactgcgct ttccattctg gctttaatga ggatccattc    1260
gtttgtgaat atcaaggcca atcgtctgac ctgcctcaac ctcctgtcaa tgctggcggc    1320
ggctctggtg gtggttctgg tggcggctct gagggtggtg ctctgaggg tggcggttct     1380 gagggtggcg gctctgaggg aggcggttcc ggtggtggct ctggttccgg tgattttgat    1440
tatgaaaaga tggcaaacgc taataagggg gctatgaccg aaaatgccga tgaaaacgcg    1500
ctacagtctg acgctaaagg caaacttgat tctgtcgcta ctgattacgg tgctgctatc    1560
gatggtttca ttggtgacgt ttccggcctt gctaatggta atggtgctac tggtgatttt    1620
gctggctcta attcccaaat ggctcaagtc ggtgacggtg ataattcacc tttaatgaat    1680
aatttccgtc aatatttacc ttccctccct caatcggttg aatgtcgccc ttttgtcttt    1740
ggcgctggta accatatga ttttctatt gattgtgaca aaataaactt attccgtggt      1800
gtctttgcgt ttctttata tgttgccacc tttatgtatg tattttctac gtttgctaca     1860
tactgcgtaa taaggagtct taataagctt                                     1890
```

<210> SEQ ID NO 6
<211> LENGTH: 694
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6

```
tctagataac gagggcaaaa aatgaaaaag acagctatcg cgattgcagt ggctctggct     60
ggcttcgcta ccgtagcgca ggccatggct tccatgaccg tggtcagca gatgggtcag     120 gactccacct cagacctgat cccagcccca cctctgagca aggtccctct gcagcagaac    180
ttccaggaca ccaattcca tgggaagtgg tatgtggtag tctcgcagg gaatgcaatt      240 ctcagagaag acaaagaccc gcaaaagatg tatgccacca tctatgagct gaaagaagac    300
aagagctaca atgtcacctc cgtcctgttt aggaaaaaga gtgtgactac tggatcgcg     360 actttttgttc caggttccca gccaggcgag ttcacgctgg caacattaa gagttaccct    420 ggattaacga gttacctcgt ccgagtggtg agcaccaact acaaccagca tgctatggtg    480
ttcttcaagg cagtttctca aaacagggag tacttcgcga ttaccatcta cgggagaacc    540
```

```
aaggagctgg cttcggaact aaaggagaac ttcatccgct tctctaaatc tctgggcctc      600
cctgaaaacc acatcgtctt ccctgtccca atcgaccagt gtatcgacgg cagcgcttgg      660
tcccacccgc agttcgaaaa ataataagct tatt                                  694
```

```
<210> SEQ ID NO 7
<211> LENGTH: 805
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
tctagataac gagggcaaaa aatgaaaaag acagctatcg cgattgcagt ggcactggct       60
ggtttcgcta ccgtagcgca ggcccaggac tccacctcag acctgatccc agccccacct     120
ctgagcaagg tccctctgca gcagaacttc aggacaacc aattccatgg gaagtggtat      180
gtggtaggtc tcgcagggaa tgcaattctc agagaagaca agacccgca aaagatgtat     240 gccaccatct atgagctgaa agaagacaag agctacaatg tcacctccgt cctgtttagg    300
aaaaagaagt gtgactactg gatcaggact tttgttccag gttgccagcc cggcgagttc    360
acgctgggca acattaagag ttaccctgga ttaacgagtt acctcgtccg agtggtgagc    420
accaactaca accagcatgc tatggtgttc ttcaagaaag tttctcaaaa cagggagtac    480
ttcaagatta ccatctacgg gagaaccaag gagctggctt cggaactaaa ggagaacttc    540
atccgcttct ctaaatctct gggcctccct gaaaaccaca tcgtcttccc tgtcccaatc    600
gaccagtgta tcgacggcag cgcttggtcc cacccgcagt tcgaaaaata ggctagcctg    660
gctgaagcta aagttctggc taaccgtgaa ctggacaaat acggtgtttc cgactactac    720
aaaaacctca tcaacaacgc taaaaccgtt gaaggtgtta aagctctgat cgacgaaatt    780
ctcgcagcac tgccgtaata agctt                                          805
```

```
<210> SEQ ID NO 8
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Val Glu Asp
        115                 120                 125

```
Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 9
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Tyr Ile Trp Arg Asn Asp Arg Tyr Pro
            35                  40                  45

Met Gln Met Tyr Ala Thr Ile Tyr Glu Leu Lys Glu Asp Lys Ser Tyr
        50                  55                  60

Asn Val Thr Ser Val Ile Phe Asp Thr Lys Lys Cys Glu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Arg Met Asp Thr Ser Tyr Leu Val Arg Val Val Ser
            100                 105                 110

Thr Asn Tyr Asn Gln His Ala Met Val Phe Phe Lys Gln Val Asn His
        115                 120                 125

Asn Thr Glu His Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 10
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45
```

```
Met Asn Met Tyr Ala Thr Ile Tyr Glu Leu Lys Glu Asp Lys Ser Tyr
         50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 11
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
         50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln Tyr Ala Met Val Phe Phe Lys Leu Ala Glu Asp
            115                 120                 125

Asn Ala Glu Phe Phe Ala Val Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 12
<211> LENGTH: 186
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 12

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln His Ala Thr Val Phe Phe Lys Leu Ala Glu Asp
            115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
                180                 185

<210> SEQ ID NO 13
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu His Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Asn Gln His Ala Met Val Phe Phe Glu Leu Val Glu Asp
            115                 120                 125

Asn Ala Gly Phe Phe Ala Ile Thr Ile Tyr Gly Arg Thr Lys Glu Leu
```

```
                130             135             140
Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 14
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Met Val Phe Phe Glu Leu Val Glu Asp
            115                 120                 125

Asn Ala Gly Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 15
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
```

```
                50                  55                  60
Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln His Ala Val Val Phe Gln Leu Val Glu Asp
                115                 120                 125

Asn Ala Gly Phe Phe Ala Ile Thr Ile Tyr Gly Arg Thr Lys Glu Leu
                130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
                180                 185

<210> SEQ ID NO 16
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Leu Gly Leu Ala Gly Asn Arg Ile Leu Arg Asp Asp Gln His Pro
                 35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln His Ala Met Val Phe Phe Lys Leu Ala Glu Asp
                115                 120                 125

Asn Ala Glu Phe Phe Ala Ile Thr Ile Tyr Gly Arg Thr Lys Glu Leu
                130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
                180                 185

<210> SEQ ID NO 17
<211> LENGTH: 186
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 17

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Phe
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125

Asn Ala Glu Phe Phe Ala Val Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185
```

<210> SEQ ID NO 18
<211> LENGTH: 186
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 18

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Gln His Pro
        35                  40                  45

Met Asp Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140
```

-continued

```
Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 19
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Arg His Pro
            35                  40                  45

Met Asn Met Tyr Ala Thr Ile Tyr Glu Leu Lys Glu Asp Lys Ser Tyr
        50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 20
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
        50                  55                  60
```

```
Asp Val Thr Ser Val Ile Phe Pro His Lys Lys Cys Glu Tyr Thr Thr
 65                  70                  75                  80

Ala Thr Phe Val Pro Gly Ser Gln Pro Gly Glu Phe Thr Leu Gly Asn
                 85                  90                  95

Ile Lys Ser Tyr Gly Gly Lys Thr Ser Tyr Leu Val Arg Val Val Ser
                100                 105                 110

Thr Asn Tyr Asn Gln His Ala Thr Val Phe Phe Lys Leu Ala Gly Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe
            180                 185

<210> SEQ ID NO 21
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 22
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 22

```
Gln Asp Ser Thr Ser Asp Leu Ile Pro Ala Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Ser Asp
             85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 23
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Asp Ser Thr Ser Asp Leu Ile Pro Ala Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Ser Asp
             85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

```
                    165                 170                 175

Asp Gly

<210> SEQ ID NO 24
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Asp Ser Thr Ser Asp Leu Ile Pro Ala Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Leu Ser His Lys Lys Cys Glu Tyr Thr Ile
 65                  70                  75                  80

Ala Thr Phe Val Pro Gly Ser Arg Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 25
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Asp Ser Thr Ser Asp Leu Ile Pro Ala Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asp Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95
```

```
Ile Lys Ser Tyr Gly Asp Lys Thr Ser Tyr Leu Val Arg Val Val Ser
            100                 105                 110

Thr Asp Tyr Ser Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 26
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Leu Ser His Lys Lys Cys Glu Tyr Thr Val
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 27
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

Val Val Gly Leu Ala Gly Asn Arg Ile Leu Arg Asp Asp Gln His Pro
        35                  40                  45

Met Asn Met Tyr Ala Thr Val Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln Tyr Ala Val Val Phe Phe Lys Leu Ala Glu Asp
         115                 120                 125

Asn Ala Glu Phe Phe Ala Ile Thr Ile Tyr Gly Arg Thr Lys Glu Leu
     130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 28
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
         115                 120                 125

Asp Ala Glu Phe Phe Ala Ile Thr Ile Tyr Gly Arg Thr Lys Glu Leu
     130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
<211> LENGTH: 237

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys Pro Ala Ser Leu
            180                 185                 190

Ala Glu Ala Lys Val Leu Ala Asn Arg Glu Leu Asp Lys Tyr Gly Val
        195                 200                 205

Ser Asp Tyr Tyr Lys Asn Leu Ile Asn Asn Ala Lys Thr Val Glu Gly
    210                 215                 220

Val Lys Ala Leu Ile Asp Glu Ile Leu Ala Ala Leu Pro
225                 230                 235

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctacttcctg aagacctgaa cacc                                         24

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttagaattg cctcagctct tgg                                          23

```
<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggttttactc tgctccctga ggac                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcttttagag actgaagtat gctc                                              24

<210> SEQ ID NO 34
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Val Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 35
<211> LENGTH: 178
<212> TYPE: PRT
<213> ORGANISM: Artificial Sequence
<220> FEATURE:
<223> OTHER INFORMATION: Description of Artificial Sequence: Synthetic
```

```
    polypeptide

<400> SEQUENCE: 35

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Tyr Ile Trp Arg Asn Asp Arg Tyr Pro
        35                  40                  45

Met Gln Met Tyr Ala Thr Ile Tyr Glu Leu Lys Glu Asp Lys Ser Tyr
50                  55                  60

Asn Val Thr Ser Val Ile Phe Asp Thr Lys Lys Cys Glu Tyr Pro Ile
65                  70                  75                  80

Ala Thr Phe Val Pro Gly Ser Gln Pro Gly Glu Phe Thr Leu Gly Asn
                85                  90                  95

Ile Lys Ser Tyr Arg Met Asp Thr Ser Tyr Leu Val Arg Val Val Ser
            100                 105                 110

Thr Asn Tyr Asn Gln His Ala Met Val Phe Phe Lys Gln Val Asn His
        115                 120                 125

Asn Thr Glu His Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 36
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Met Val Phe Phe Lys Leu Ala Glu Asp
        115                 120                 125

Asn Ala Glu Phe Phe Ala Val Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
            165                 170                 175

Asp Gly

<210> SEQ ID NO 37
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Asp Ser Thr Ser Asp Leu Ile Pro Ala Pro Pro Leu Ser Lys Val
 1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 38
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Asp Ser Thr Ser Asp Leu Ile Pro Ala Pro Pro Leu Ser Lys Val
 1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn

```
                    85                  90                  95
Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 39
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu His Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln His Ala Met Val Phe Phe Glu Leu Val Glu Asp
            115                 120                 125

Asn Ala Gly Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Met Val Phe Phe Glu Leu Val Glu Asp
                115                 120                 125

Asn Ala Gly Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 41
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Val Val Phe Phe Gln Leu Val Glu Asp
                115                 120                 125

Asn Ala Gly Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 42
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Leu Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Met Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 43
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Phe Pro His Lys Lys Cys Glu Tyr Thr Phe
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln His Ala Thr Val Phe Phe Lys Leu Ala Glu Asp
        115                 120                 125
```

Asn Ala Glu Phe Phe Ala Val Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asp Met Tyr Ala Thr Ile Tyr Glu Leu Lys Glu Asp Lys Ser Tyr
        50                  55                  60

Asn Val Thr Ser Val Ile Phe Pro His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asn Tyr Asn Gln His Ala Thr Val Phe Phe Lys Leu Ala Glu Asp
            115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 45
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Arg His Pro
            35                  40                  45

Met Asn Met Tyr Ala Thr Ile Tyr Glu Leu Lys Glu Asp Lys Ser Tyr

```
                50                  55                  60
Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
                100                 105                 110

Thr Asn Tyr Asn Gln His Ala Thr Val Phe Phe Lys Leu Ala Glu Asp
                115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
 50                  55                  60

Asp Val Thr Ser Val Ile Phe Pro His Lys Lys Cys Glu Tyr Thr Thr
 65                  70                  75                  80

Ala Thr Phe Val Pro Gly Ser Gln Pro Gly Glu Phe Thr Leu Gly Asn
                 85                  90                  95

Ile Lys Ser Tyr Gly Gly Lys Thr Ser Tyr Leu Val Arg Val Val Ser
                100                 105                 110

Thr Asn Tyr Asn Gln His Ala Thr Val Phe Phe Lys Leu Ala Gly Asp
                115                 120                 125

Asn Ala Glu Phe Phe Ala Ile Thr Ile Tyr Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 47
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Leu Ser His Lys Lys Cys Glu Tyr Thr Val
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 48
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asp Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Ser Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 49
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
     50                  55                  60

Asn Val Thr Ser Val Ile Phe Pro His Lys Lys Cys Glu Tyr Thr Ile
 65                  70                  75                  80

Ala Thr Phe Val Pro Gly Ser Gln Pro Gly Glu Phe Thr Leu Ser Asp
            85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 50
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
         35                  40                  45

Met Asn Met Tyr Ala Thr Val Tyr Glu Leu Lys Glu Asp Lys Ser Tyr
     50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
            85                  90                  95

```
Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 51
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Leu Ser His Lys Lys Cys Glu Tyr Thr Ile
65                  70                  75                  80

Ala Thr Phe Val Pro Gly Ser Arg Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asn Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 52
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
```

-continued

```
                 20                  25                  30
Val Val Gly Leu Ala Gly Asn Arg Ile Leu Arg Asp Asp Gln His Pro
             35                  40                  45
Met Asn Met Tyr Ala Thr Ile Tyr Glu Leu Lys Glu Asp Lys Ser Tyr
         50                  55                  60
Asn Val Thr Ser Val Ile Ser Ser His Lys Lys Cys Glu Tyr Thr Ile
 65                  70                  75                  80
Ala Thr Phe Val Pro Gly Ser Gln Pro Gly Glu Phe Thr Leu Gly Asn
                 85                  90                  95
Ile Lys Ser Tyr Gly Asp Lys Thr Ser Tyr Leu Val Arg Val Val Ser
            100                 105                 110
Thr Asn Tyr Asn Gln Tyr Ala Val Val Phe Phe Lys Leu Ala Glu Asp
            115                 120                 125
Asn Ala Glu Phe Phe Ala Ile Thr Ile Tyr Gly Arg Thr Lys Glu Leu
        130                 135                 140
Ala Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

```
<210> SEQ ID NO 53
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

```
Gln Asp Ser Thr Ser Asp Leu Ile Pro Ala Pro Pro Leu Ser Lys Val
  1               5                  10                  15
Pro Leu Gln Gln Asn Phe Gln Asp Asn Gln Phe His Gly Lys Trp Tyr
             20                  25                  30
Val Val Gly Leu Ala Gly Asn Arg Ile Leu Arg Asp Asp Gln His Pro
         35                  40                  45
Met Asn Met Tyr Ala Thr Ile Tyr Glu Leu Lys Glu Asp Lys Ser Tyr
     50                  55                  60
Asn Val Thr Ser Val Ile Phe Pro His Lys Lys Cys Glu Tyr Thr Ile
 65                  70                  75                  80
Ala Thr Phe Val Pro Gly Ser Gln Pro Gly Glu Phe Thr Leu Gly Asn
                 85                  90                  95
Ile Lys Ser Tyr Gly Asp Lys Thr Ser Tyr Leu Val Arg Val Val Ser
            100                 105                 110
Thr Asp Tyr Asn Gln Tyr Ala Val Val Phe Phe Lys Leu Ala Glu Asp
            115                 120                 125
Asp Ala Glu Phe Phe Ala Ile Thr Ile Tyr Gly Arg Thr Lys Glu Leu
        130                 135                 140
Ala Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

```
<210> SEQ ID NO 54
```

```
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 55
<211> LENGTH: 629
<212> TYPE: DNA
<213> ORGANISM: Artificial Sequence
<220> FEATURE:
<223> OTHER INFORMATION: Description of Artificial Sequence: Synthetic
      construct <400> SEQUENCE: 55
tctagataac gagggcaaaa aatgaaaaag acagctatcg cgattgcagt ggctctggct      60
ggcttcgcta ccgtagcgca ggcccaggac tccacctcag acctgatccc agccccacct     120
ctgagcaagg tccctctgca gcagaacttc caggacaacc aattccatgg aagtggtat     180
gtggtaggtc tcgcagggaa tgcaattctc agagaagaca agacccgca aagatgtat      240
gccaccatct atgagctgaa agaagacaag agctacaatg tcacctccgt cctgtttagg     300
aaaaagaagt gtgactactg gatcgcgact tttgttccag gttcccagcc aggcgagttc     360
acgctgggca acattaagag ttaccctgga ttaacgagtt acctcgtccg agtggtgagc     420
accaactaca accagcatgc tatggtgttc ttcaaggcag tttctcaaaa cagggagtac     480
ttcgcgatta ccatctacgg gagaaccaag gagctggctt cggaactaaa ggagaacttc     540
atccgcttct ctaaatctct gggcctccct gaaaaccaca tcgtcttccc tgtcccaatc     600
gaccagtgta tcgacggcta ataagcttg                                       629

<210> SEQ ID NO 56
```

<211> LENGTH: 630
<212> TYPE: DNA
<213> ORGANISM: Artificial Sequence
<220> FEATURE:
<223> OTHER INFORMATION: Description of Artificial Sequence: Synthetic construct

<400> SEQUENCE: 56

| | |
|---|---|
| tctagataac gagggcaaaa aatgaaaaag acagctatcg cgattgcagt ggctctggct | 60 |
| ggcttcgcta ccgtagcgca ggcccaggac tccacctcag acctgatccc agccccacct | 120 |
| ctgagcaagg tccctctgca gcagaacttc caggacaacc aattccatgg gaagtggtat | 180 |
| gtggtaggtc tcgcagggaa ccggattctg agagatgacc agcatccgat gaatatgtat | 240 |
| gccaccatct atgagctgaa agaagacaag agctacaatg tcacctccgt catttcttcg | 300 |
| cataagaagt gtgagtacac gatcgcgact tttgttccag gttcccagcc aggcgagttc | 360 |
| acgctgggca acattaagag ttacggggat aagacgagtt acctcgtccg agtggtgagc | 420 |
| accgactaca accagtatgc tgtggtgttc tttaagcttg ctgaggataa cgcggagttt | 480 |
| ttcgcaatta ccatctacgg gagaaccaag gagctggctt cggaactaaa ggagaacttc | 540 |
| atccgcttct ctaaatctct gggcctccct gaaaaccaca tcgtcttccc tgtcccaatc | 600 |
| gaccagtgta tcgacggcta ataagcttga | 630 |

<210> SEQ ID NO 57
<211> LENGTH: 1026
<212> TYPE: DNA
<213> ORGANISM: Artificial Sequence
<220> FEATURE:
<223> OTHER INFORMATION: Description of Artificial Sequence: Synthetic construct

<400> SEQUENCE: 57

| | |
|---|---|
| tctagataac gagggcaaaa aatgaaaaag acagctatcg cgattgcagt ggctctggct | 60 |
| ggcttcgcta ccgtagcgca ggcccaggac tccacctcag acctgatccc agccccacct | 120 |
| ctgagcaagg tccctctgca gcagaacttc caggacaacc aattccatgg gaagtggtat | 180 |
| gtggtaggtc tcgcagggaa tgcaattctc agagaagaca aagaccccgca aaagatgtat | 240 |
| gccaccatct atgagctgaa agaagacaag agctacaatg tcacctccgt cctgtttagg | 300 |
| aaaaagaagt gtgactactg gatcgcgact tttgttccag gttcccagcc aggcgagttc | 360 |
| acgctgggca acattaagag ttaccctgga ttaacgagtt acctcgtccg agtggtgagc | 420 |
| accaactaca accagcatgc tatggtgttc ttcaaggcag tttctcaaaa cagggagtac | 480 |
| ttcgcgatta ccatctacgg gagaaccaag gagctggctt cggaactaaa ggagaacttc | 540 |
| atccgcttct ctaaatctct gggcctccct gaaaaccaca tcgtcttccc tgtcccaatc | 600 |
| gaccagtgta tcgacggcag cacgaccaag accagcggcc cgcgtgctgc cccggaagtc | 660 |
| tatgcgtttg cgacgccgga gtggccgggg agccgggaca agcgcaccct cgcctgcctg | 720 |
| atccagaact tcatgcctga ggacatctcg gtgcagtggc tgcacaacga ggtgcagctc | 780 |
| ccggacgccc ggcacagcac gacgcagccc cgcaagacca agggctccgg cttcttcgtc | 840 |
| ttcagccgcc tggaggtgac cagggccgaa tgggagcaga agatgagttt catctgccgt | 900 |
| gcagtccatg aggcagcgag cccctcacag accgtccagc gagcggtgtc tgtaaatccc | 960 |
| gagtcatcga ggagcggtgg ctgcagcgct tggtcccacc cgcagttcga aaataataa | 1020 |
| gcttga | 1026 |

<210> SEQ ID NO 58
<211> LENGTH: 1026
<212> TYPE: DNA
<213> ORGANISM: Artificial Sequence
<220> FEATURE:
<223> OTHER INFORMATION: Description of Artificial Sequence: Synthetic construct

<400> SEQUENCE: 58

| | | | | | |
|---|---|---|---|---|---|
| tctagataac | gagggcaaaa | aatgaaaaag | acagctatcg | cgattgcagt | ggctctggct | 60 |
| ggcttcgcta | ccgtagcgca | ggcccaggac | tccacctcag | acctgatccc | agccccacct | 120 |
| ctgagcaagg | tccctctgca | gcagaacttc | caggacaacc | aattccatgg | gaagtggtat | 180 |
| gtggtaggtc | tcgcagggaa | ccggattctg | agagatgacc | agcatccgat | gaatatgtat | 240 |
| gccaccatct | atgagctgaa | agaagacaag | agctacaatg | tcacctccgt | catttcttcg | 300 |
| cataagaagt | gtgagtacac | gatcgcgact | tttgttccag | gttcccagcc | aggcgagttc | 360 |
| acgctgggca | acattaagag | ttacggggat | aagacgagtt | acctcgtccg | agtggtgagc | 420 |
| accgactaca | accagtatgc | tgtggtgttc | tttaagcttg | ctgaggataa | cgcggagttt | 480 |
| ttcgcaatta | ccatctacgg | gagaaccaag | gagctggctt | cggaactaaa | ggagaacttc | 540 |
| atccgcttct | ctaaatctct | gggcctccct | gaaaaccaca | tcgtcttccc | tgtcccaatc | 600 |
| gaccagtgta | tcgacggcag | cacgaccaag | accagcggcc | cgcgtgctgc | cccggaagtc | 660 |
| tatgcgtttg | cgacgccgga | gtggccgggg | agccgggaca | agcgcaccct | cgcctgcctg | 720 |
| atccagaact | tcatgcctga | ggacatctcg | gtgcagtggc | tgcacaacga | ggtgcagctc | 780 |
| ccggacgccc | ggcacagcac | gacgcagccc | cgcaagacca | agggctccgg | cttcttcgtc | 840 |
| ttcagccgcc | tggaggtgac | cagggccgaa | tgggagcaga | agatgagtt | catctgccgt | 900 |
| gcagtccatg | aggcagcgag | cccctcacag | accgtccagc | gagcggtgtc | tgtaaatccc | 960 |
| gagtcatcga | ggagcggtgg | ctgcagcgct | tggtcccacc | cgcagttcga | aaataataa | 1020 |
| gcttga | | | | | | 1026 |

<210> SEQ ID NO 59
<211> LENGTH: 826
<212> TYPE: DNA
<213> ORGANISM: Artificial Sequence
<220> FEATURE:
<223> OTHER INFORMATION: Description of Artificial Sequence: Synthetic construct

<400> SEQUENCE: 59

| | | | | | |
|---|---|---|---|---|---|
| tctagataac | gagggcaaaa | aatgaaaaag | acagctatcg | cgattgcagt | ggctctggct | 60 |
| ggcttcgcta | ccgtagcgca | ggcccaggac | tccacctcag | acctgatccc | agccccacct | 120 |
| ctgagcaagg | tccctctgca | gcagaacttc | caggacaacc | aattccatgg | gaagtggtat | 180 |
| gtggtaggtc | tcgcagggaa | ccggattctg | agagatgacc | agcatccgat | gaatatgtat | 240 |
| gccaccatct | atgagctgaa | agaagacaag | agctacaatg | tcacctccgt | catttcttcg | 300 |
| cataagaagt | gtgagtacac | gatcgcgact | tttgttccag | gttcccagcc | aggcgagttc | 360 |
| acgctgggca | acattaagag | ttacggggat | aagacgagtt | acctcgtccg | agtggtgagc | 420 |
| accgactaca | accagtatgc | tgtggtgttc | tttaagcttg | ctgaggataa | cgcggagttt | 480 |
| ttcgcaatta | ccatctacgg | gagaaccaag | gagctggctt | cggaactaaa | ggagaacttc | 540 |
| atccgcttct | ctaaatctct | gggcctccct | gaaaaccaca | tcgtcttccc | tgtcccaatc | 600 |
| gaccagtgta | tcgacggcag | cggaggtgcc | gtcgacgcta | actctctggc | tgaagctaaa | 660 |

```
gttctggcta accgtgaact ggacaaatac ggtgtttccg actactacaa aaacctcatc      720
aacaacgcta aaccgttga aggtgttaaa gctctgatcg acgaaattct cgcagcactg      780
ccgagcgctt ggtctcaccc gcagttcgaa aaataataag cttgac                    826
```

<210> SEQ ID NO 60
<211> LENGTH: 826
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 60

```
tctagataac gagggcaaaa aatgaaaaag acagctatcg cgattgcagt ggctctggct      60
ggcttcgcta ccgtagcgca ggcccaggac tccacctcag acctgatccc agccccacct    120
ctgagcaagg tccctctgca gcagaacttc caggacaacc aattccatgg gaagtggtat    180
gtggtaggtc tcgcagggaa tgcaattctc agagaagaca agacccgca aaagatgtat     240 gccaccatct atgagctgaa agaagacaag agctacaatg tcacctccgt cctgtttagg    300 aaaagaagt gtgactactg gatcaggact tttgttccag gttcccagcc aggcgagttc     360
acgctgggca acattaagag ttaccctgga ttaacgagtt acctcgtccg agtggtgagc    420
accaactaca accagcatgc tatggtgttc ttcaagaaag tttctcaaaa cagggagtac    480
ttcaagatta ccatctacgg gagaaccaag gagctggctt cggaactaaa ggagaacttc    540
atccgcttct ctaaatctct gggcctccct gaaaaccaca tcgtcttccc tgtcccaatc    600
gaccagtgta tcgacggcag cggaggtgcc gtcgacgcta actctctggc tgaagctaaa    660
gttctggcta accgtgaact ggacaaatac ggtgtttccg actactacaa aaacctcatc    720
aacaacgcta aaccgttga aggtgttaaa gctctgatcg acgaaattct cgcagcactg    780
ccgagcgctt ggtctcaccc gcagttcgaa aaataataag cttgac                    826
```

<210> SEQ ID NO 61
<211> LENGTH: 675
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 61

```
tctagataac gagggcaaaa aatgaaaaag acagctatcg cgattgcagt ggctctggct      60
ggcttcgcta ccgtagcgca ggcccaggac tccacctcag acctgatccc agccccacct    120
ctgagcaagg tccctctgca gcagaacttc caggacaacc aattccatgg gaagtggtat    180
gtggtaggtc tcgcagggaa ccggattctg agagatgacc agcatccgat gaatatgtat    240
gccaccatct atgagctgaa agaagacaag agctacaatg tcacctccgt catttcttcg    300
cataagaagt gtgagtacac gatcgcgact tttgttccag gttgccagcc aggcgagttc    360
acgctgggca acattaagag ttacggggat aagacgagtt acctcgtccg agtggtgagc    420
accgactaca accagtatgc tgtggtgttc tttaagcttg ctgaggataa cgcggagttt    480
ttcgcaatta ccatctacgg gagaaccaag gagctggctt cggaactaaa ggagaacttc    540
atccgcttct ctaaatctct gggcctccct gaaaaccaca tcgtcttccc tgtcccaatc    600
gaccagtgta tcgacggcag cgcttggtcc cacccgcagt tcgaaaaata ataagcttga    660
cctgtgaagt gaaaa                                                     675
```

-continued

<210> SEQ ID NO 62
<211> LENGTH: 675
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 62

```
tctagataac gagggcaaaa aatgaaaaag acagctatcg cgattgcagt ggctctggct    60
ggcttcgcta ccgtagcgca ggcccaggac tccacctcag acctgatccc agccccacct   120
ctgagcaagg tccctctgca gcagaacttc caggacaacc aattccatgg gaagtggtat   180
gtggtaggtc tcgcagggaa tgcaattctc agagaagaca agacccgca aaagatgtat    240
gccaccatct atgagctgaa agaagacaag agctacaatg tcacctccgt cctgtttagg   300
aaaaagaagt gtgactactg gatcaggact tttgttccag gttcccagcc aggcgagttc   360
acgctgggca acattaagag ttaccctgga ttaacgagtt acctcgtccg agtggtgagc   420
accaactaca accagcatgc tatggtgttc ttcaagaaag tttctcaaaa cagggagtac   480
ttcaagatta ccatctacgg agaaccaag gagctggctt cggaactaaa ggagaacttc    540
atccgcttct ctaaatctct gggcctccct gaaaaccaca tcgtcttccc tgtcccaatc   600
gaccagtgta tcgacggcag cgcttggtcc cacccgcagt cgaaaaata ataagcttga    660
cctgtgaagt gaaaa                                                     675
```

<210> SEQ ID NO 63
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
     50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Cys Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

<210> SEQ ID NO 64
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 64

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Cys Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 65
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 65

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
```

```
                100                 105                 110
Thr Asp Tyr Asn Gln Tyr Ala Val Val Phe Lys Leu Ala Glu Asp
        115                 120                 125

Asn Ala Glu Phe Phe Ala Ile Thr Ile Tyr Gly Arg Cys Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 66
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
     50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
                100                 105                 110

Thr Asp Tyr Cys Gln Tyr Ala Val Val Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 67
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                20                  25                  30
```

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Cys Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 68
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Cys Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 69
<211> LENGTH: 178
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 69

Gln Asp Ser Thr Ser Asp Leu Ile Pro Ala Pro Pro Leu Cys Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 70
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Arg Ile Leu Arg Asp Asp Gln His Pro
         35                  40                  45

Met Asn Met Tyr Ala Thr Ile Tyr Glu Leu Lys Glu Asp Lys Ser Tyr
 50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                 85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
130                 135                 140
```

```
Ala Ser Glu Leu Lys Glu Asn Phe Ile Arg Phe Ser Lys Cys Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 71
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Glu Asp Lys Ser Tyr
        50                  55                  60

Asn Val Thr Ser Val Ile Ser Ser His Lys Lys Cys Glu Tyr Thr Ile
65                  70                  75                  80

Ala Thr Phe Val Pro Gly Ser Cys Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 72
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Arg Ile Leu Arg Asp Asp Gln His Pro
            35                  40                  45

Met Asn Met Tyr Ala Thr Ile Tyr Glu Leu Lys Cys Asp Lys Ser Tyr
        50                  55                  60

Asn Val Thr Ser Val Ile Ser Ser His Lys Lys Cys Glu Tyr Thr Ile
```

```
              65                  70                  75                  80
Ala Thr Phe Val Pro Gly Ser Gln Pro Gly Glu Phe Thr Leu Gly Asn
                    85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 73
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Asp Ser Thr Ser Asp Leu Ile Pro Ala Pro Pro Leu Ser Lys Val
  1               5                  10                  15

Pro Leu Gln Gln Cys Phe Gln Asp Asn Gln Phe His Gly Lys Trp Tyr
                 20                  25                  30

Val Val Gly Leu Ala Gly Asn Arg Ile Leu Arg Asp Asp Gln His Pro
             35                  40                  45

Met Asn Met Tyr Ala Thr Ile Tyr Glu Leu Lys Glu Asp Lys Ser Tyr
         50                  55                  60

Asn Val Thr Ser Val Ile Ser Ser His Lys Lys Cys Glu Tyr Thr Ile
 65                  70                  75                  80

Ala Thr Phe Val Pro Gly Ser Gln Pro Gly Glu Phe Thr Leu Gly Asn
                    85                  90                  95

Ile Lys Ser Tyr Gly Asp Lys Thr Ser Tyr Leu Val Arg Val Val Ser
                100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 74
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Leu Ala Gly Asn Ala Ile Leu Arg Glu Asp Lys Asp Pro
         35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Ser Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctacttcctg aagacctgaa cacc                                              24

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gttagaattg cctcagctct tgg                                               23

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggttttactc tgctccctga ggac                                              24

<210> SEQ ID NO 78
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 78
gcttttagag actgaagtat gctc                                              24

<210> SEQ ID NO 79
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79
```

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Ala Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Ala Val Ser Gln
        115                 120                 125

Asn Arg Glu Tyr Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80
```

Leu Met Tyr Pro Pro Tyr Tyr
1               5

```
<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 1 to 5
      'Gly-Gly-Gly-Ser' repeating units.
```

```
<400> SEQUENCE: 81

Gly Gly Gly Ser Gly Gly Gly Ser Gly Gly Gly Ser Gly Gly Gly Ser
1               5                   10                  15

Gly Gly Gly Ser
            20

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 82

His His His His His His
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Ile Ile Asn Phe Glu Lys Leu
1               5
```